United States Patent
Andrianjara et al.

(10) Patent No.: US 6,849,637 B2
(45) Date of Patent: Feb. 1, 2005

(54) TRIAZOLO COMPOUNDS AS MMP INHIBITORS

(75) Inventors: Charles Andrianjara, Fresnes (FR); Francine Breuzard, Quincy Sous Senart (FR); Bernard Gaudilliere, Nanterre (FR); Henri Jacobelli, Paray Vieille Poste (FR)

(73) Assignee: Warner-Lambert Company, Morris Plains, NJ (US)

( * ) Notice: Subject to any disclaimer, the term of this patent is extended or adjusted under 35 U.S.C. 154(b) by 39 days.

(21) Appl. No.: 10/075,654

(22) Filed: Feb. 14, 2002

(65) Prior Publication Data

US 2002/0151558 A1 Oct. 17, 2002

Related U.S. Application Data

(60) Provisional application No. 60/268,757, filed on Feb. 14, 2001.

(51) Int. Cl.[7] .................... C07D 487/04; A61K 31/519
(52) U.S. Cl. ...................... 514/267; 544/250; 544/251
(58) Field of Search ............................... 544/250, 251; 514/267

(56) References Cited

U.S. PATENT DOCUMENTS

| | | | |
|---|---|---|---|
| 4,455,311 A | 6/1984 | Kienzle | |
| 5,948,780 A | 9/1999 | Peterson, Jr. et al. | 514/255 |
| 6,008,243 A | 12/1999 | Bender et al. | 514/422 |
| 2002/0193377 A1 | 12/2002 | Andrianjara et al. | |
| 2003/0078276 A1 | 4/2003 | Andrianjara et al. | |
| 2003/0130278 A1 | 7/2003 | Gaudilliere et al. | |
| 2003/0144274 A1 | 7/2003 | Bunker et al. | |
| 2003/0216402 A1 | 11/2003 | Gaudilliere et al. | |
| 2003/0220355 A1 | 11/2003 | Gaudilliere et al. | |
| 2004/0006077 A1 | 1/2004 | Gaudilliere et al. | |
| 2004/0063673 A1 | 4/2004 | Johnson | |

FOREIGN PATENT DOCUMENTS

| | | |
|---|---|---|
| EP | 0 076 199 | 4/1983 |
| EP | 0 217 748 | 4/1987 |
| EP | 0935963 | 8/1999 |
| EP | 1138680 | 10/2001 |
| WO | WO 00/09485 | 2/2000 |
| WO | WO 00/66584 | 4/2000 |
| WO | WO 01/12611 | 2/2001 |
| WO | WO 01/63244 A1 | 8/2001 |
| WO | WO 02/34726 | 5/2002 |
| WO | WO 02/34753 | 5/2002 |
| WO | WO02/064080 A2 | 8/2002 |
| WO | WO 02/064080 | 8/2002 |
| WO | WO02/064080 A3 | 8/2002 |
| WO | WO 02/064572 | 8/2002 |
| WO | WO02/064572 A1 | 8/2002 |
| WO | WO02/064595 A1 | 8/2002 |
| WO | WO03/032999 A1 | 4/2003 |
| WO | WO03/033478 A1 | 4/2003 |
| WO | WO03/076417 A2 | 9/2003 |
| WO | WO03/076417 A3 | 9/2003 |
| WO | WO04/000322 A1 | 12/2003 |

OTHER PUBLICATIONS

Beers et al., Crohn's Disease; Ulcerative Colitis; Psoriasis, The Merck Manual of Diagnosis and Therapy, Seventeenth Edition (online), 1999.*
Casanova et al., PubMed Abstract (Rev. Neurol. 28(9):909–15) May 1999.*
Bremner et al., Therapy of Crohn's Disease in childhoo, Exp. Opin. Pharmacother. 3(70:809–825, 2002.*
Robinson, Medical Therapy of Inflammatory Bowel Disease for the 21st century, Eur. J. Surg. Suppl. 582:90–98, 1998.*

(List continued on next page.)

*Primary Examiner*—Deepak Rao
(74) *Attorney, Agent, or Firm*—Pfizer, Inc.; Charles W. Ashbrook; Claude F. Purchase, Jr.

(57) ABSTRACT

A compound selected from those of formula (I):

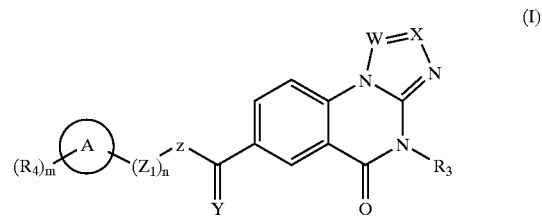

in which:
W represents N or C—$R_1$; in which $R_1$ is as defined in the description,
X represents N or C—$R_2$ in which $R_2$ is as defined in the description,
Y represents a group selected from oxygen, sulfur, —NH, and —Nalkyl,
Z represents a group selected from oxygen, sulphur, —$NR_8$ in which $R_8$ is as defined in the description, and optionally carbon depending the definition of Y,
n is an integer from 0 to 8 inclusive,
$Z_1$ represents a group —$CR_9R_{10}$ wherein $R_9$ and $R_{10}$, are as defined in the description, which group contains optionally multiple bonds or heteroatomes,
A represents a cyclic group,
m is an integer from 0 to 7 inclusive,
the group(s) $R_4$ is (are) as defined in the description,
$R_3$ represents a group selected from hydrogen, alkyl, alkenyl, alkynyl, and the group of formula:

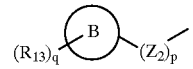

in which p, $Z_2$, B, q, and $R_{13}$ are as defined in the description,
optionally, its racemic forms, isomers thereof, N-oxydes thereof, and its the pharmaceutically acceptable salts thereof, and medicinal products containing the same are useful as specific inhibitors of type-13 matrix mettaloprotease.

39 Claims, No Drawings

OTHER PUBLICATIONS

Singh et al., Immune Therapy in Inflammatory Bowel Disease and models of colitis, British Journal of Surgery, 88, pp. 1558–1569, 2001.*

Simone, Oncology: Introduction, Cecil Textbook of Medicine, 20th Edition, vol. 1, pp. 1004–1010, 1996.*

Morris et al., PubMed Abstract (Invasion Metastasis, 17(6):281–96), 1997.*

Rasmussen et al., Matrix Metalloproteinase Inhibition as a Novel Anticancer Strategy, Pharmacol. Ther., vol. 75, No. 1, pp. 69–75, 1997.*

Chambers et al., Changing Views of the Role of Matrix Metalloproteinases in Metastasis, Journal of National Cancer Institute, vol. 89, No. 17, Sep. 1997.*

(List continued on next page.)

Lovejoy et al., "Crystal structures of MMP–1 and –13 reveal the structural basis for selectivity of collagenase inhibitors", Nature Structural Biology, 1999, vol. 6, No. 3, pp. 217–221.

Moy et al., "High–resolution Solution Structure of the Catalytic Fragment of Human Collagenase–3 (MMP–13) Complexed with a Hydroxamic Acid Inhibitor", J. Mol. Biol., 2000, vol. 302, 671–689.

Mitchell et al., "Cloning Expression, and Type II Collagenolytic Activity of Matrix Metalloproteinase–13 from Human Osteoarthritic Cartilage", J. Clin. Invest., 1996, vol. 97, No. 3, pp. 761–768.

Neuhold et al., "Postnatal expression in hyaline cartilage of constitutively active human collagenase–3 (MMP–13) reduces osteoarthritis in mice", J. Clin. Invest., 2001, vol. 107, No. 1, pp. 35–44.

Dahlberg et al., "Selective Enhancement of CollagenaseMediated Cleavage of Resident Type II Collagen in Cultured Osteoarthritis Cartilage and Arrest with a Synthetic Inhibitor that Spares Collagenase 1 (Matrix Metalloproteinase 1)", Arthrit. & Rheum., 2000, vol. 43, No. 3, pp. 673–682.

Billinghurst et al., "Comparison of the Degradation of Type II Collagen and Proteoglycan in Nasal and Articular Cartilages Induced by Interleukin–1 and the Selection Inhibition of Type II Collagen Cleavage by Collagenase", Arthrit. & Rheum., 2000, vol. 43, No. 3, pp. 664–672.

Billinghurst et al., "Enhanced Cleavage of Type II Collagen by Collagenases in Osteoarthritic Articular Cartilage", J. Clin. Invest., 1997, vol. 99, No. 7, pp. 1534–1545.

Hirota et al., "Novel Synthesis of Pyrido[3,4–d]pyrimidines, Pyrido[2,3–d]pyrimidines, and Quinazolines via Palladium–Catalyzed Oxidative Coupling", Heterocycles, 1994, vol. 37, No. 1, pp. 563–570.

U.S. Appl. No. 10/634,473, filed Aug. 5, 2003, Bunker et al.

U.S. Appl. No. 10/634,289, filed Aug. 5, 2003, Bunker et al.

U.S. Appl. No. 10/634,180, filed Aug. 5, 2003, Bunker et al.

U.S. Appl. No. 10/634,712, filed Aug. 5, 2003, Hicks et al.

U.S. Appl. No. 10/634,181, filed Aug. 5, 2003, Li.

U.S. Appl. No. 10/634,489, filed Aug. 5, 2003, Roark.

U.S. Appl. No. 10/634,420, filed Aug. 5, 2003, Roark.

U.S. Appl. No. 10/634,716, filed Aug. 5, 2003, Nahra et al.

U.S. Appl. No. 10/634,288, filed Aug. 5, 2003, O'Brien.

U.S. Appl. No. 10/634,182, filed Aug. 5, 2003, Li.

U.S. Appl. No. 10/734,718, filed Aug. 5, 2003, Ortwine.

Montana, John, et al, "The design of selective non–substrate–based matrix metalloproteinase inhibitors", Current Opinion in Drug Discovery & Development, 2000; 3(4), pp 353–361.

Clark, Ian, et al, "Matrix metalloproteinase inhibitors in the treatment of arthritis", Current Opinions in Anti–inflammatory & Immunomodulatory Investigational Drugs, 2000; 2(1), pp 16–25.

Chen, James, et al, "Structure–Based Design of a Novel, Potent, and Selective Inhibitor for MMP–13 Utilizing NMR Spectroscopy and Computer–Aided Molecular Design", J. Am. Chem. Soc., 2000, 122; pp 9648–9654.

* cited by examiner

TRIAZOLO COMPOUNDS AS MMP INHIBITORS

CROSS-REFERENCE TO RELATED APPLICATIONS

This application claims benefit of priority from U.S. Provisional Patent Application No. 60/268,757, filed Feb. 14, 2001.

FIELD OF THE INVENTION

The present invention relates to novel cyclized quinazolines which are useful for preparing medicinal products for treating complaints involving a therapy with a matrix metalloprotease-13 (MMP-13) inhibitor. These medicinal products are useful in particular for treating certain inflammatory conditions such as rheumatoid arthritis or osteoarthritis, as well as certain proliferative conditions such as cancers.

TECHNOLOGICAL BACKGROUND OF THE INVENTION

Matrix metalloproteases (MMPs) are enzymes which are involved in the renewal of extracellular matrix tissue, such as cartilage, tendons and joints. MMPs bring about the destruction of the extracellular matrix tissue, which is compensated for, in a non-pathological physiological state, by its simultaneous regeneration.

Under normal physiological conditions, the activity of these extremely aggressive peptidases is controlled by specialized proteins which inhibit MMPs, such as the tissue-x inhibitors of metalloprotease (TIMPs).

In pathological situations, an irreversible degradation of articular cartilage takes place, as is the case in rheumatic diseases such as rheumatoid arthritis or osteoarthritis. In these pathologies, the cartilage degradation process predominates, leading to a destruction of the tissue and resulting in a loss of function.

At least twenty different matrix metalloproteases have been identified to date and are subdivided into four groups, the collagenases, the gelatinases, the stromelysins and the membrane-type MMPs (MT-MMPs), respectively.

Matrix metalloprotease-13 (MMP-13) is a collagenase-type MMP which constitutes the predominant collagenase observed during osteoarthritis, in the course of which pathology the chondrocyte directs the destruction of cartilage.

Local equilibrium of the activities of MMPs and TIMPs is critical for the renewal of the extracellular matrix. Modifications of this equilibrium which result in an excess of active MMPs, relative to their inhibitor, induce a pathological destruction of cartilage, which is observed in particular in rheumatoid arthritis and in osteoarthritis.

There is a need in the prior art for novel MMP inhibitors, more particularly for MMP-13 inhibitors, in order to prevent and/or correct the imbalance in the renewal of extracellular matrix tissue, as well as to prevent or treat conditions such as rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases (COPDs), age-related macular degeneration (ARMD) and cancer.

MMP-inhibitor compounds are known. Most of these MMP inhibitors are not selective for only one MMP, such as, for example, those which have been described by Montana and Baxter (2000) or by Clark et al. (2000).

There is a need in the prior art for novel inhibitors that are active on matrix metalloprotease-13 in order to enrich the therapeutic arsenal that can be used for treating pathologies associated with the destruction of the extracellular matrix and with cancer.

SUMMARY OF THE INVENTION

The invention relates to cyclized quinazolines of formula (I)

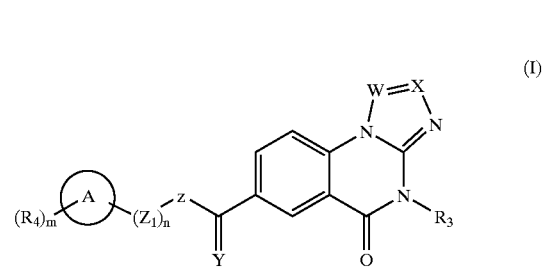

in which:
W represents N or C—$R_1$; in which $R_1$ is selected from:
  hydrogen atom,
  $OR_5$, $SR_5$ in which $R_5$ is selected from hydrogen, $(C_1-C_6)$ alkyl and aryl$(C_1-C_6)$alkyl,
  $(C_1-C_6)$alkyl, cycloalkyl of 3 to 8 carbon atoms optionally interrupted with one hetero atom selected from oxygen, sulfur and nitrogen, aryl, heteroaryl and aryl$(C_1-C_6)$alkyl, these groups being optionally substituted by $(CH_2)$p-OH or $(CH_2)$p-$NH_2$, in which p is an integer from 0 to 4 inclusive,
X represents N or C—$R_2$ in which $R_2$ is selected from:
  hydrogen atom,
  $NR_6R_7$, $OR_6$, $SR_6$ in which $R_6$ and $R_7$, identical or different, are selected from hydrogen, $(C_1-C_6)$alkyl and aryl$(C_1-C_6)$alkyl,
  $(C_1-C_6)$alkyl, cycloalkyl of 3 to 8 carbon atoms optionally interrupted with one hetero atom selected from oxygen, sulfur and nitrogen, aryl, heteroaryl and aryl$(C_1-C_6)$alkyl, these groups being optionally substituted by $(CH_2)$p-OH or $(CH_2)$p-$NH_2$, in which p is an integer from 0 to 4 inclusive,
Y represents a group selected from oxygen, sulfur, —NH, and —N$(C_1-C_6)$alkyl,
Z represents a group selected from:
  oxygen, sulphur,
  and —$NR_8$ in which $R_8$ represents a group selected from hydrogen, $(C_1-C_6)$alkyl, aryl$(C_1-C_6)$alkyl, cycloalkyl, aryl, and heteroaryl, and
  when Y is oxygen, sulphur, or —N$(C_1-C_6)$alkyl, Z optionally represents a carbon atom which is optionally substituted by a group selected from $(C_1-C_6)$alkyl, aryl, aryl$(C_1-C_6)$alkyl, aromatic heterocycle, non-aromatic heterocycle, and cycloalkyl,
n is an integer from 0 to 8 inclusive,
$Z_1$ represents a group —$CR_9R_{10}$ wherein $R_9$ and $R_{10}$, identical or different, represent a group selected from hydrogen, $(C_1-C_6)$alkyl, halo$(C_1-C_6)$alkyl, halogen, $NR_5R_{11}$, $OR_5$, $SR_5$ and C(=O)$OR_5$ in which $R_5$ and $R_{11}$, identical or different, represents hydrogen atom or $(C_1-C_6)$alkyl, and
  when n is greater than or equal to 2, the hydrocarbon chain $Z_1$ optionally contains one or more multiple bonds,
  and/or one of the carbon atoms in the hydrocarbon chain $Z_1$ may be replaced with an oxygen atom, a sulphur atom which is optionally substituted by one or two oxygen atoms, or a nitrogen atom which is optionally substituted by $(C_1-C_6)$alkyl, A represents a group selected from:
aromatic or non-aromatic, 5- or 6-membered monocycle comprising from 0 to 4 heteroatoms selected from nitrogen, oxygen and sulphur, and
bicycle, composed of two aromatic or non-aromatic, 5- or 6-membered rings, which may be identical or different, comprising from 0 to 4 heteroatoms selected from nitrogen, oxygen and sulphur, m is an integer from 0 to 7 inclusive, the group(s) $R_4$, which may be identical or different, is (are) selected from $(C_1-C_6)$alkyl, halogen, —CN, —NO$_2$, —SCF$_3$, —CF$_3$, —OCF$_3$, —NR$_5$R$_{11}$, —OR$_5$, —SR$_5$, —SOR$_5$, —SO$_2$R$_5$, —(CH$_2$)$_k$SO$_2$NR$_5$R$_{11}$, —X$_1$(CH$_2$)$_k$C(=O)OR$_5$, —(CH$_2$)$_k$C(=O)OR$_5$, —X$_1$(CH$_2$)$_k$C(=O)NR$_5$R$_{11}$, —(CH$_2$)$_k$C(=O)NR$_5$R$_{11}$, and —X$_2$—R$_{12}$ in which:

$X_1$ represents a group selected from oxygen, sulphur optionally substituted by one or two oxygen atoms, and nitrogen substituted by hydrogen or $(C_1-C_6)$alkyl, k is an integer from 0 to 3 inclusive, $R_5$ and $R_{11}$, which may be identical or different, are selected from hydrogen and $(C_1-C_6)$alkyl, $X_2$ represents a group selected from single bond, —CH$_2$—, oxygen atom, sulphur atom optionally substituted by one or two oxygen atoms, and nitrogen atom substituted by hydrogen atom or $(C_1-C_6)$alkyl group, $R_{12}$ represents an aromatic or non-aromatic, heterocyclic or non-heterocyclic, 5- or 6-membered ring which is optionally substituted by one or more groups, which may be identical or different, selected from $(C_1-C_6)$alkyl, halogen, hydroxyl, and amino, and when the ring is heterocyclic, it comprises from 1 to 4 heteroatoms selected from nitrogen, oxygen and sulphur, $R_3$ represents a group selected from:
hydrogen,
$(C_1-C_6)$alkyl, $(C_2-C_6)$alkenyl, $(C_2-C_6)$alkynyl, these groups being optionally substituted by one or more groups, which may be identical or different, selected from amino, cyano, halo$(C_1-C_6)$alkyl, cycloalkyl, —C(=O)NR$_5$R$_{11}$, —C(=O)OR$_5$, —OR$_5$, and —SR$_5$, in which $R_5$ and $R_{11}$, which may be identical or different, are as defined hereinbefore,
and the group of formula:

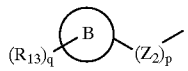

in which p is an integer from 0 to 8 inclusive, $Z_2$ represents —CR$_{14}$R$_{15}$ wherein $R_{14}$ and $R_{15}$, identical or different, represent a group selected from hydrogen, $(C_1-C_6)$alkyl, phenyl, halo$(C_1-C_6)$alkyl, halogen, amino, —OR$_5$, —NR$_5$R$_{11}$, —SR$_5$ and —C(=O)OR$_5$ in which $R_5$ and $R_{11}$, identical or different, are as defined hereinbefore, and
when p is greater than or equal to 2, the hydrocarbon chain $Z_2$ optionally contains one or more multiple bonds,
and/or one of the carbon atoms in the hydrocarbon chain $Z_2$ may be replaced with an oxygen atom, a sulphur atom which is optionally substituted by one or two oxygen atoms, or a nitrogen atom which is optionally substituted by $(C_1-C_6)$alkyl, B represents a group selected from:
aromatic or non-aromatic 5- or 6-membered monocycle comprising from 0 to 4 heteroatoms selected from nitrogen, oxygen and sulphur, and
bicycle, composed of two aromatic or non-aromatic, 5- or 6-membered rings, which may be identical or different, comprising from 0 to 4 heteroatoms selected from nitrogen, oxygen and sulphur, q is an integer from 0 to 7 inclusive, the group(s) $R_{13}$, which may be identical or different, is (are) selected from $(C_1-C_6)$alkyl, halogen, —CN, —NO$_2$, —CF$_3$, —OCF$_3$, $(C_1-C_6)$acyl, —(CH$_2$)$_k$NR$_{16}$R$_{17}$, —X$_3$—(CH$_2$)$_k$NR$_{16}$R$_{17}$—N(R$_{16}$)C(=O)R$_{17}$, —N(R$_{16}$)C(=O)OR$_{17}$, —N(R$_{16}$)SO$_2$R$_{17}$, —N(SO$_2$R$_{16}$)$_2$, —OR$_{16}$, —S(O)$_k$R$_{16}$, —(CH$_2$)$_{k1}$SO$_2$NR$_{16}$R$_{17}$, —X$_3$(CH$_2$)$_k$C(=O)OR$_{16}$, —(CH$_2$)$_k$C(=O)OR$_{16}$, —X$_3$(CH$_2$)$_k$C(=O)NR$_{16}$R$_{17}$, —(CH$_2$)$_k$C(=O)NR$_{16}$R$_{17}$, —C(=O)O—R$_{19}$—NR$_{16}$NR$_{17}$ and —X$_4$—R$_{18}$, in which:

$X_3$ represents a group selected from oxygen, sulphur optionally substituted by one or two oxygen atoms, and nitrogen substituted by a hydrogen atom or a $(C_1-C_6)$alkyl group, k is an integer from 0 to 3 inclusive, $k_1$ is an integer from 0 to 2 inclusive, $R_{16}$ and $R_{17}$, which may be identical or different, are selected from hydrogen and $(C_1-C_6)$alkyl, $X_4$ represents a group selected from single bond, —CH$_2$—, oxygen atom, sulphur atom optionally substituted by one or two oxygen atoms, and nitrogen atom substituted by hydrogen atom or $(C_1-C_6)$alkyl group, $R_{18}$ represents an aromatic or non-aromatic, heterocyclic or non-heterocyclic, 5- or 6-membered ring, which is optionally substituted by one or more groups, which may be identical or different, selected from $(C_1-C_6)$alkyl, halogen, hydroxyl, $(C_1-C_6)$alkoxy, oxo, cyano, tetrazole, —NR$_5$R$_{11}$, and —C(=O)OR$_5$ wherein $R_5$ and $R_{11}$ are as defined hereinbefore, and, when the ring is heterocyclic, it comprises from 1 to 4 heteroatoms selected from nitrogen, oxygen and sulphur, $R_{19}$ represents a $(C_1-C_6)$alkylene group, optionally, the racemic forms, isomers thereof, N-oxydes thereof, and the pharmaceutically acceptable salts thereof.

The compounds of the present invention are useful as inhibitors, in particular as selective inhibitors, of the enzyme matrix metalloprotease-13 (MMP-13).

The invention also relates to a process for manufacturing the compound of formula (I) in which W, X, $R_3$, $R_4$, n, m, $Z_1$ and A are as defined above, Y is O and Z is O, the said process being characterized in that it comprises the reaction of the compound of formula (7a):

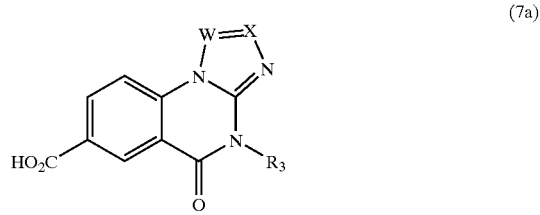

(7a)

in which W, X, and $R_3$ are as defined in the compound of formula (I), with the compound of general formula (7g), in the presence of a base:

(7g)

in which hal is a halogen atom such as chlorine or bromine, and in which $R_4$, n, m, $Z_1$ and A are as defined in the compound of formula (I),
to give the compound of general formula (7c), which is a particular case of the compounds of formula (I):

(7c)

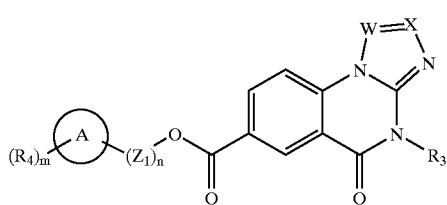

in which W, X, $R_3$, $R_4$, n, m, $Z_1$ and A are as defined hereinbefore.

A subject of the present invention is also a process for manufacturing a compound of formula (I) in which W, X, $R_3$, $R_4$, n, m, $Z_1$ and A are as defined above, Y is O and Z is $-NR_8$, the said process being characterized in that it comprises the reaction of the compound of formula (7a):

(7a)

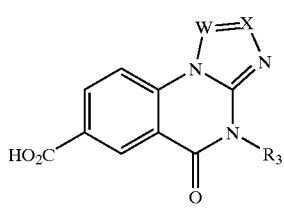

in which W, X, and $R_3$ are as defined in the compound of formula (I), with the compound of general formula (7i):

(7i)

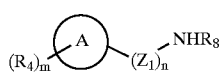

in which $R_4$, $R_8$, n, m, $Z_1$ and A are as defined in the compound of formula (I),
by activating the acid function with an activator such as O-[(ethoxycarbonyl)cyanomethyleneamino]-N,N,N',N'-tetramethyluronium tetrafluoroborate (TOTU), in the presence of diisopropylethylamine (DIPEA) in a solvent such as dimethylformamide (DMF), to give the compound of general formula (7d), which is a particular case of the compounds of formula (I):

(7d)

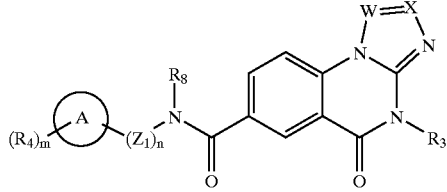

in which W, X, $R_3$, $R_4$, $R_8$, n, m, $Z_1$ and A are as defined hereinbefore.

A subject of the present invention is also a process for manufacturing a compound of formula (I) in which W, X, $R_3$, $R_4$, n, m, $Z_1$ and A are as defined above, Y is O and Z is S, the said process being characterized in that it comprises the reaction of the compound of formula (7a):

(7a)

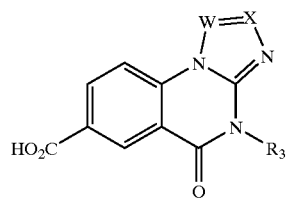

in which W, X, and $R_3$ are as defined in the compound of formula (I)
with the compound of general formula (7j)

(7j)

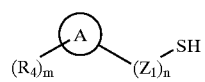

in which $R_4$, n, m, $Z_1$ and A are as defined in the compound of formula (I),
by activating the acid function with an activator such as TOTU, in the presence of DIPEA in a solvent such as DMF, to give the compound of general formula (7e), which is a particular case of the compounds of formula (I):

(7e)

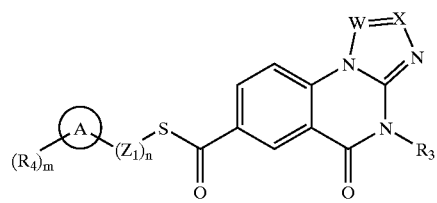

in which W, X, $R_3$, $R_4$, n, m, $Z_1$ and A are as defined hereinbefore.

The invention also relates to a process for manufacturing the compound of formula (I) in which W, X, $R_3$, $R_4$, n, m, $Z_1$ and A are as defined above, Y is O and Z is O, the said process being characterized in that it comprises the reaction of the compound of formula (7b):

(7b)

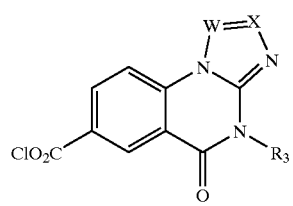

in which W, X, and $R_3$ are as defined in the compound of formula (I),
with the compound of formula (7h):

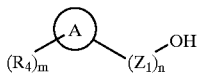
(7h)

in which $R_4$, n, m, $Z_1$ and A are as defined in the compound of formula (I),
in the presence of a base such as triethylamine (TEA), to give the compound of general formula (7c), which is a particular case of the compounds of formula (I):

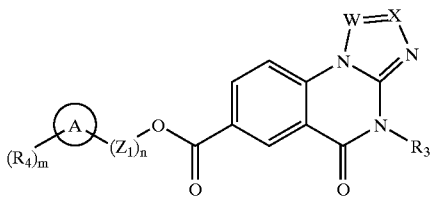
(7c)

in which W, X, $R_3$, $R_4$, n, m, $Z_1$ and A are as defined hereinbefore.

The invention also relates to a process for manufacturing the compound of formula (I) in which W, X, $R_3$, $R_4$, n, m, $Z_1$ and A are as defined above, Y is O and Z is —$NR_8$, the said process being characterized in that it comprises the reaction of the compound of formula (7b):

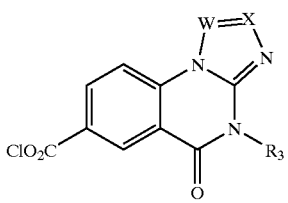
(7b)

in which W, X, and $R_3$ are as defined in the compound of formula (I),
with the compound of formula (7i):

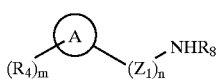
(7i)

in which $R_4$, $R_8$, n, m, $Z_1$ and A are as defined in the compound of formula (I), in the presence of a base such as TEA, to give the compound of general formula (7d), which is a particular case of the compounds of formula (I):

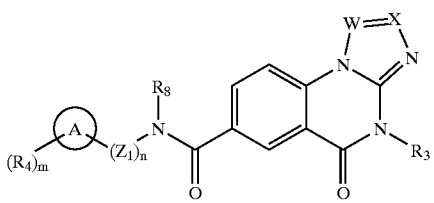
(7d)

in which W, X, $R_3$, $R_4$, $R_8$, n, m, $Z_1$ and A are as defined hereinbefore.

The invention also relates to a process for manufacturing the compound of formula (I) in which W, X, $R_3$, $R_4$, n, m,
$Z_1$ and A are as defined above, Y is O and Z is S, the said process being characterized in that it comprises the reaction of the compound of formula (7b):

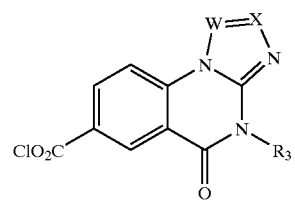
(7b)

in which W, X, and $R_3$ are as defined in the compound of formula (I), with the compound of general formula (7j):

(7j)

in which $R_4$, n, m, $Z_1$ and A are as defined in the compound of formula (I), to give the compound of general formula (7e), which is a particular case of the compounds of formula (I):

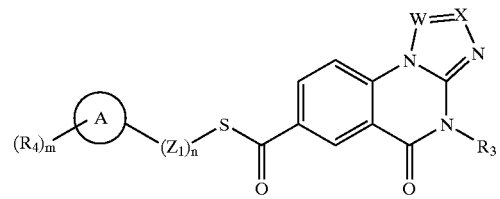
(7e)

in which W, X, $R_3$, $R_4$, n, m, $Z_1$ and A are as defined hereinbefore.

The invention also relates to a process for manufacturing the compound of formula (I) in which W, X, $R_3$, $R_4$, n, m, $Z_1$ and A are as defined above, Y is O and Z is —CHRa, in which Ra represents a group selected from hydrogen, ($C_1$–$C_6$)alkyl, aryl, aryl($C_1$–$C_6$)alkyl, aromatic heterocycle, non-aromatic heterocycle, and cycloalkyl, the said process being characterized in that it comprises the reaction of the compound of formula (7b):

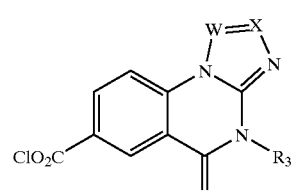
(7b)

in which W, X, and $R_3$ are as defined in the compound of formula (I), with the compound of general formula (7k):

(7k)

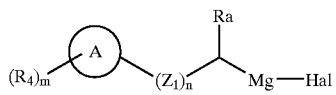

in which Ra represents a group selected from hydrogen, $(C_1-C_6)$alkyl, aryl, aryl$(C_1-C_6)$alkyl, aromatic heterocycle, non-aromatic heterocycle, and cycloalkyl, Hal represents a halogen atom, and $R_4$, n, m, $Z_1$ and A are as defined in the compound of formula (I),
to give the compound of general formula (7f), which is a particular case of the compounds of formula (I):

(7f)

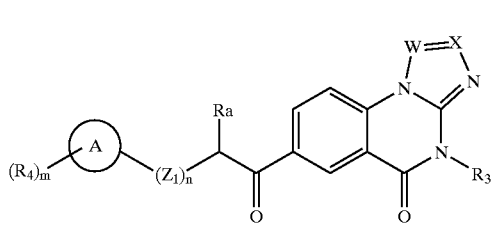

in which W, X, $R_3$, $R_4$, Ra, n, m, $Z_1$ and A are as defined hereinbefore.

The invention also relates to a process for manufacturing the compound of formula (I) in which W, X, $R_3$, $R_4$, n, m, Z, $Z_1$ and A are as defined in the summary of the invention and Y is S, the said process being characterized in that it comprises the reaction of the compound (8a), which represents all the compounds of formulae (7c), (7d), (7e), and (7f):

(8a)

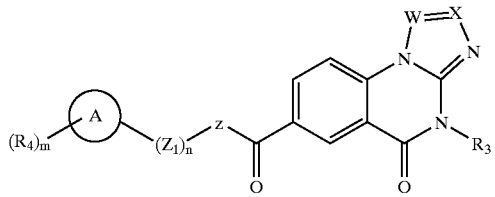

in which W, X, $R_3$, $R_4$, n, m, Z, $Z_1$ and A are as defined in the compound of formula (I), with Lawesson's reagent or $P_2S_5$, to give the compound of general formula (8b), which is a particular case of the compounds of formula (I):

(8b)

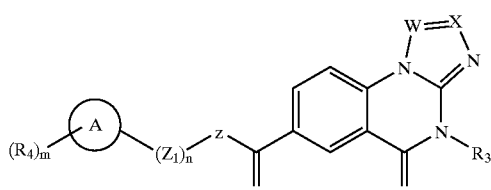

in which W, X, $R_3$, $R_4$, n, m, Z, $Z_1$ and A are as defined hereinbefore.

The invention also relates to a process for manufacturing the compound of formula (I) in which W, X, $R_3$, $R_4$, n, m, $Z_1$ and A are as defined above, Y is NH and Z is O, the said process being characterized in that it comprises the reaction of compound (9a):

(9a)

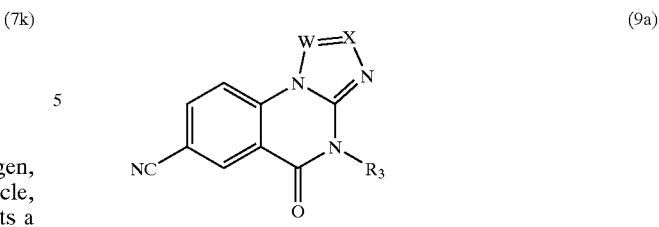

in which W, X, and $R_3$ are as defined in the compound of formula (I), with the compound of general formula (7h):

(7h)

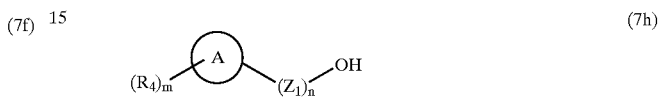

in which $R_4$, n, m, $Z_1$ and A are as defined in the compound of formula (I),
to give the compound of general formula (9b), which is a particular case of the compounds of formula (I):

(9b)

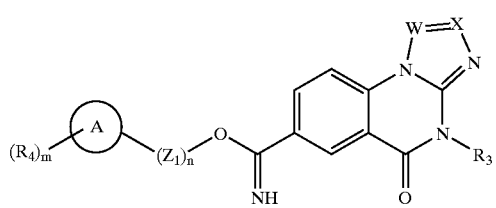

in which W, X, $R_3$, $R_4$, n, m, $Z_1$ and A are as defined hereinbefore.

The invention also relates to a process for manufacturing the compound of formula (I) in which W, X, $R_3$, $R_4$, n, m, $Z_1$ and A are as defined in the summary of the invention, Z is —$NR_8$ and Y is NH, the said process being characterized in that it comprises the reaction of compound (9a):

(9a)

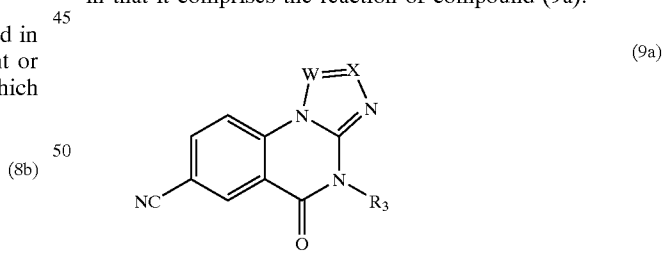

in which W, X, and $R_3$ are as defined in the compound of formula (I), with the compound of general formula (7i):

(7i)

in which $R_4$, n, m, $Z_1$ and A are as defined in the compound of formula (I), to give the compound of general formula (9c), which is a particular case of the compounds of formula (I):

(9c)

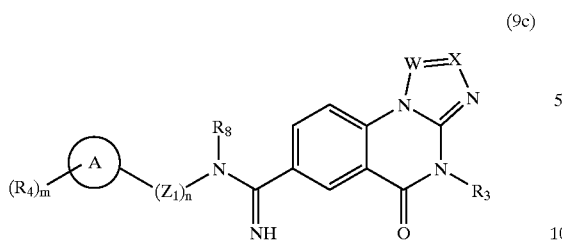

in which W, X, $R_3$, $R_4$, $R_8$, n, m, $Z_1$ and A are as defined hereinbefore.

The invention also relates to a process for manufacturing the compound of formula (I) in which W, X, $R_3$, $R_4$, n, m, $Z_1$ and A are as defined in the summary of the invention, Z is S and Y is NH, the said process being characterized in that it comprises the reaction of compound (9a):

(9a)

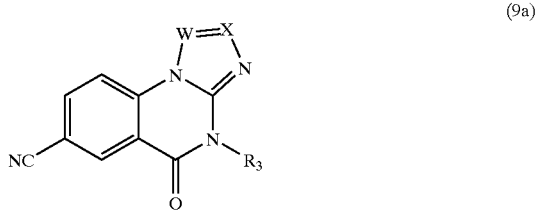

in which W, X, and $R_3$ are as defined in the compound of formula (I)
with the compound of general formula (7j):

(7j)

in which $R_4$, n, m, $Z_1$ and A are as defined in the compound of formula (I),
to give the compound of general formula (9d) which is a particular case of the compounds of formula (I):

(9d)

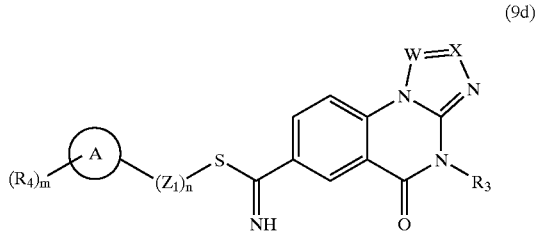

in which W, X, $R_3$, $R_4$, n, m, $Z_1$ and A are as defined hereinbefore.

The invention also relates to a process for manufacturing the compound of formula (I) in which W, X, $R_3$, $R_4$, n, m, $Z_1$ and A are as defined in the summary of the invention, Z is —CHRa in which Ra represents a group selected from hydrogen, $(C_1-C_6)$alkyl, aryl, aryl$(C_1-C_6)$alkyl, aromatic heterocycle, non-aromatic heterocycle, and cycloalkyl, and Y is N—Rb in which Rb is a $(C_1-C_6)$alkyl, the said process being characterized in that it comprises the reaction of compound (7f):

(7f)

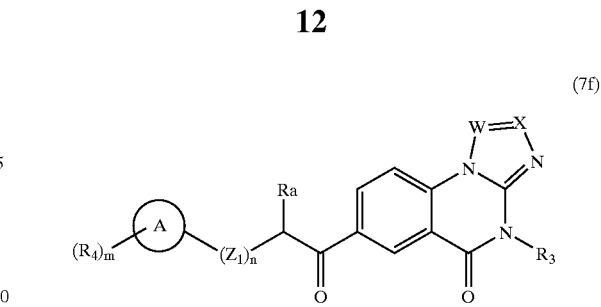

in which W, X, $R_3$, $R_4$, n, m, $Z_1$ and A are as defined in the compound of formula (I), and in which Ra is as defined hereinbefore,
with Rb—$NH_2$, in which Rb represents a $(C_1-C_6)$alkyl group, in a presence of a dehydrating agent, to give the compound of general formula (10a), which is a particular case of the compounds of formula (I):

(10a)

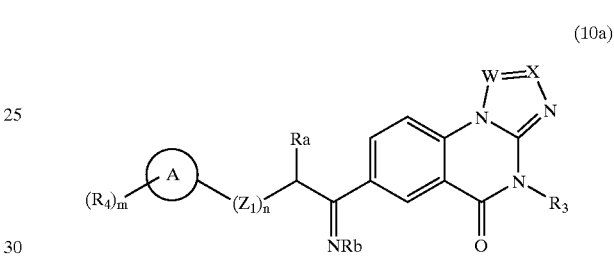

in which W, X, $R_3$, $R_4$, n, m, $Z_1$, Ra, Rb and A are as defined hereinbefore.

The invention also relates to a pharmaceutical composition comprising a compound of formula (I) and a pharmaceutically acceptable excipient.

The invention also relates to the use of a compound of formula (I) for the preparation of a medicinal product intended for treating a disease or complaint involving therapy by inhibition of matrix metalloproteases, and more particularly of MMP-13, such as rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases (COPDs), age-related macular degeneration (ARMD) and cancer.

The invention also relates to a method for treating a disease or complaint involving a therapy by inhibition of matrix metalloproteases, and more particularly of MMP-13, the said method comprising the administration of an effective concentration of a compound of formula (I) to a patient.

DETAILED DESCRIPTION OF THE INVENTION

The Applicant has identified according to the invention novel compounds that are matrix metalloprotease inhibitors, and more specifically novel compounds that are MMP-13 inhibitors.

The subject of the invention is thus cyclized quinazolines of formula (I):

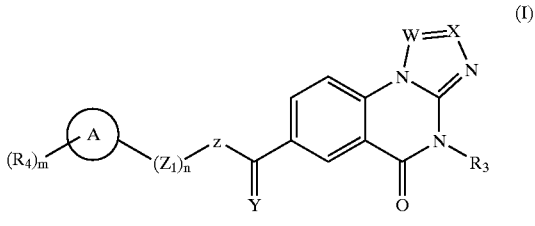

(I)

in which W, X, Y, Z, R₃, R₄, n, m, Z₁ and A are as defined in the summary of the invention, optionally the racemic forms, isomers thereof, N-oxydes thereof, as well as the pharmaceutically acceptable salts thereof.

The invention relates particularly to the compounds of general formula (I) in which:

W is C—R$_1$ and X is N or C—R$_2$ in which R$_1$ and R$_2$, identical or different, are selected from hydrogen and methyl, Y is O, Z represents an oxygen atom or —NH group, n is an integer from 0 to 4 inclusive, Z$_1$ represents a group —CR$_9$R$_{10}$ wherein R$_9$ and R$_{10}$, identical or different, represent a group selected from hydrogen, (C$_1$–C$_6$)alkyl, halo(C$_1$–C$_6$)alkyl, halogen, —NR$_5$R$_{11}$, —OR$_5$, —SR$_5$ and —C(=O)OR$_5$ in which R$_5$ and R$_{11}$, identical or different, represent hydrogen atom or (C$_1$–C$_6$)alkyl, and when n is greater than or equal to 2, the hydrocarbon chain Z$_1$ optionally contains one double bonds, and/or one of the carbon atoms in the hydrocarbon chain Z$_1$ may be replaced with an oxygen atom, a sulphur atom which is optionally substituted by one or two oxygen atoms, or a nitrogen atom which is optionally substituted by (C$_1$–C$_6$)alkyl, R$_3$, R$_4$ and A are as defined in the compound of formula (I).

The invention also relates to the compounds of general formula (I) in which R$_3$ represents the group of formula:

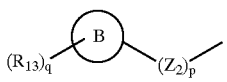

in which p is an integer from 0 to 4 inclusive,

Z$_2$ represents —CR$_{14}$R$_{15}$ wherein R$_{14}$ and R$_{15}$, identical or different, represent a group selected from hydrogen and methyl, and when p is greater than or equal to 2, the hydrocarbon chain Z$_2$ optionally contains one double bond, B represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, q is an integer from 0 to 7 inclusive, the group(s) R$_{13}$, which may be identical or different, is (are) selected from (C$_1$–C$_6$)alkyl, halogen, —CN, —CF$_3$, —NR$_{16}$R$_{17}$, —OR$_{16}$, —SO$_2$R$_{16}$, —(CH$_2$)$_k$SO$_2$NR$_{16}$R$_{17}$, —O(CH$_2$)$_k$C(=O)OR$_{16}$, —(CH$_2$)$_k$C(=O)OR$_{16}$, —O(CH$_2$)$_k$C(=O)NR$_{16}$R$_{17}$, —C(=O)O—R$_{19}$—NR$_{16}$NR$_{17}$ and —(CH$_2$)$_k$C(=O)NR$_{16}$R$_{17}$, in which k is an integer from 0 to 3 inclusive, R$_{16}$ and R$_{17}$, which may be identical or different, are selected from hydrogen and (C$_1$–C$_6$)alkyl, and R$_{19}$ represents a (C$_1$–C$_6$)alkylene group, W, X, Y, Z, Z$_1$, n, m, A and R$_4$ are as defined in the compound of formula (I).

The invention also relates to the compounds of general formula (I) in which:

n is an integer from 0 to 4 inclusive,

Z$_1$ represents a group —CR$_9$R$_{10}$ wherein R$_9$ and R$_{10}$ represent each hydrogen atom, and when n is greater than or equal to 2, the hydrocarbon chain Z$_1$ optionally contains one double bond, and/or one of the carbon atoms in the hydrocarbon chain Z$_1$ may be replaced with an oxygen atom, a sulphur atom which is optionally substituted by one or two oxygen atoms, or a nitrogen atom which is optionally substituted by (C$_1$–C$_6$)alkyl, A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, m is an integer from 0 to 7 inclusive, the group(s) R$_4$, which may be identical or different, is (are) selected from (C$_1$–C$_6$)alkyl, halogen, —CN, —CF$_3$, —NR$_5$R$_{11}$, —OR$_5$, and —C(=O)OR$_5$ in which R$_5$ and R$_{11}$, which may be identical or different, are selected from hydrogen and (C$_1$–C$_6$)alkyl, W, X, Y, Z and R$_3$ are as defined in the compound of formula (I).

The invention relates more particularly to a cyclized quinazoline of general formula (I) in which:

W is C—R$_1$ and X is N or C—R$_2$ in which R$_1$ and R$_2$, identical or different, are selected from hydrogen and methyl, Y is O, Z represents an oxygen atom or —NH group, n is an integer from 0 to 4 inclusive, Z$_1$ represents a group —CR$_9$R$_{10}$ wherein R$_9$ and R$_{10}$, identical or different, represent a group selected from hydrogen and methyl, and when n is greater than or equal to 2, the hydrocarbon chain Z$_1$ optionally contains one or more multiple bonds, and/or one of the carbon atoms in the hydrocarbon chain Z$_1$ may be replaced with an oxygen atom, a sulphur atom which is optionally substituted by one or two oxygen atoms, or a nitrogen atom which is optionally substituted by (C$_1$–C$_6$)alkyl, A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, m is an integer from 0 to 7 inclusive, the group(s) R$_4$, which may be identical or different, is (are) selected from (C$_1$–C$_6$)alkyl, halogen, —CN, —CF$_3$, —NR$_5$R$_{11}$, —OR$_5$, —SO$_2$R$_5$, —(CH$_2$)$_k$SO$_2$NR$_5$R$_{11}$, —X$_1$(CH$_2$)$_k$C(=O)OR$_5$, —(CH$_2$)$_k$C(=O)OR$_5$, —X$_1$(CH$_2$)$_k$C(=O)NR$_5$R$_{11}$, —(CH$_2$)$_k$C(=O)NR$_5$R$_{11}$, and —X$_2$—R$_{12}$ in which:

X$_1$ represents a group selected from oxygen, sulphur and —NH, k is an integer from 0 to 3 inclusive, R$_5$ and R$_{11}$, which may be identical or different, are selected from hydrogen and (C$_1$–C$_6$)alkyl, X$_2$ represents a group selected from single bond, —CH$_2$—, oxygen atom, and sulphur atom optionally substituted by one or two oxygen atoms, R$_{12}$ represents an aromatic or non-aromatic, heterocyclic or non-heterocyclic, 5- or 6-membered ring which is optionally substituted by one or more groups, which may be identical or different, selected from (C$_1$–C$_6$) alkyl, halogen, hydroxyl and amino, and when the ring is heterocyclic, it comprises from 1 to 4 heteroatoms selected from nitrogen, oxygen and sulphur, $R_3$ represents the group of formula:

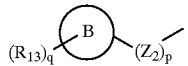

in which p is an integer from 0 to 6 inclusive, $Z_2$ represents —$CR_{14}R_{15}$ wherein $R_{14}$ and $R_{15}$, identical or different, represent a group selected from hydrogen, ($C_1$–$C_6$)alkyl, phenyl, halo($C_1$–$C_6$)alkyl, halogen, amino, $OR_5$, $SR_5$ and —$C(=O)OR_5$ in which $R_5$ is as defined in the compound of formula (I), and when p is greater than or equal to 2, the hydrocarbon chain $Z_2$ optionally contains one or more multiple bonds, and/or one of the carbon atoms in the hydrocarbon chain $Z_2$ may be replaced with an oxygen atom, a sulphur atom which is optionally substituted by one or two oxygen atoms, or a nitrogen atom which is optionally substituted by ($C_1$–$C_6$)alkyl, B represents a group selected from:
aromatic or non-aromatic 5- or 6-membered monocycle comprising from 0 to 4 heteroatoms selected from nitrogen, oxygen and sulphur, and
bicycle, composed of two aromatic or non-aromatic, 5- or 6-membered rings, which may be identical or different, comprising from 0 to 4 heteroatoms selected from nitrogen, oxygen and sulphur, q is an integer from 0 to 7 inclusive, the group(s) $R_{13}$, which may be identical or different, is (are) selected from ($C_1$–$C_6$)alkyl, halogen, —CN, —$CF_3$, —$NR_{16}R_{17}$, —$OR_{16}$, —$SO_2R_{16}$, —$(CH_2)_kSO_2NR_{16}R_{17}$, —$X_3(CH_2)_kC(=O)OR_{16}$, —$(CH_2)_kC(=O)OR_{16}$, —$X_3(CH_2)_kC(=O)NR_{16}R_{17}$, —$(CH_2)_kC(=O)NR_{16}R_{17}$, —$C(=O)O$—$R_{19}$—$NR_{16}NR_{17}$ and —$X_4$—$R_{19}$, in which:

$X_3$ represents a group selected from oxygen atom, sulphur atom and —NH group, k is an integer from 0 to 3 inclusive, $R_{16}$ and $R_{17}$, which may be identical or different, are selected from hydrogen and ($C_1$–$C_6$)alkyl, $X_4$ represents a group selected from single bond, —$CH_2$—, oxygen atom, and sulphur atom optionally substituted by one or two oxygen atoms, $R_{18}$ represents an aromatic or non-aromatic, heterocyclic or non-heterocyclic, 5- or 6-membered ring, which is optionally substituted by one or more groups, which may be identical or different, selected from ($C_1$–$C_6$)alkyl, halogen, hydroxyl, and amino, and when the ring is heterocyclic, it comprises from 1 to 4 heteroatoms selected from nitrogen, oxygen and sulphur, $R_{19}$ represents a ($C_1$–$C_6$)alkylene group.

The invention also relates to the compounds of general formula (I) in which:

W is C—$R_1$ and X is N or C—$R_2$ in which $R_1$ and $R_2$, identical or different, are selected from hydrogen and methyl, Y is O, Z represents an oxygen atom or a —NH group, n is an integer from 0 to 4 inclusive, $Z_1$ represents a group —$CR_9R_{10}$ wherein $R_9$ and $R_{10}$, identical or different, represent a group selected from hydrogen and methyl, and when n is greater than or equal to 2, the hydrocarbon chain $Z_1$ optionally contains one double bond, and/or one of the carbon atoms in the hydrocarbon chain $Z_1$ may be replaced with an oxygen atom, a sulphur atom which is optionally substituted by one or two oxygen atoms, or a nitrogen atom which is optionally substituted by ($C_1$–$C_6$)alkyl, A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, m is an integer from 0 to 7 inclusive, the group(s) $R_4$, which may be identical or different, is (are) selected from ($C_1$–$C_6$)alkyl, halogen, —CN, —$CF_3$, —$NR_5R_{11}$, —$OR_5$, and —$C(=O)OR_5$, in which $R_5$ and $R_{11}$, which may be identical or different, are selected from hydrogen and ($C_1$–$C_6$)alkyl, $R_3$ represents the group of formula:

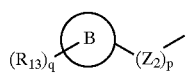

in which p is an integer from 0 to 4 inclusive, $Z_2$ represents —$CR_{14}R_{15}$ wherein $R_{14}$ and $R_{15}$, identical or different, represent a group selected from hydrogen and methyl, and when p is greater than or equal to 2, the hydrocarbon chain $Z_2$ optionally contains one double bond, and/or one of the carbon atoms in the hydrocarbon chain $Z_2$ may be replaced with an oxygen atom, a sulphur atom which is optionally substituted by one or two oxygen atoms, or a nitrogen atom which is optionally substituted by ($C_1$–$C_6$)alkyl, B represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, q is an integer from 0 to 7 inclusive, the group(s) $R_{13}$, which may be identical or different, is (are) selected from ($C_1$–$C_6$)alkyl, halogen, —CN, —$CF_3$, —$NR_{16}R_{17}$, —$OR_{16}$, —$SO_2R_{16}$, —$(CH_2)_kSO_2NR_{16}R_{17}$, —$X_3(CH_2)_kC(=O)OR_{16}$, —$(CH_2)_kC(=O)OR_{16}$, —$X_3(CH_2)_kC(=O)NR_{16}R_{17}$, —$(CH_2)_kC(=O)NR_{16}R_{17}$, —$C(=O)O$—$R_{19}$—$NR_{16}NR_{17}$ and —$X_4$—$R_{18}$, in which:

$X_3$ represents a group selected from oxygen atom, sulphur atom and —NH group, k is an integer from 0 to 3 inclusive, $R_{16}$ and $R_{17}$, which may be identical or different, are selected from hydrogen and ($C_1$–$C_6$)alkyl, $X_4$ represents a group selected from single bond, —$CH_2$—, oxygen atom, and sulphur atom optionally substituted by one or two oxygen atoms, $R_{18}$ represents an aromatic or non-aromatic, heterocyclic or non-heterocyclic, 5- or 6-membered ring, which is optionally substituted by one or more groups, which may be identical or different, selected from ($C_1$–$C_6$)alkyl, halogen, hydroxyl, and amino, and when the ring is heterocyclic, it comprises from 1 to 4 heteroatoms selected from nitrogen, oxygen and sulphur, $R_{19}$ represents a ($C_1$–$C_6$)alkylene group.

The invention also relates to a cyclized quinazoline of general formula (I) in which:

W is C—$R_1$ and X is N or C—$R_2$ in which $R_1$ and $R_2$, identical or different, are selected from hydrogen and methyl, Y is O,
Z represents an oxygen atom or a —NH group,
n is an integer from 0 to 4 inclusive,
$Z_1$ represents a methylen group, and
when n is greater than or equal to 2, the hydrocarbon chain $Z_1$ optionally contains one double bond,
and/or one of the carbon atoms in the hydrocarbon chain $Z_1$ may be replaced with an oxygen atom, a sulphur atom which is optionally substituted by one or two oxygen atoms, or a nitrogen atom which is optionally substituted by $(C_1-C_6)$alkyl,
A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl,
m is an integer from 0 to 7 inclusive,
the group(s) $R_4$, which may be identical or different, is (are) selected from $(C_1-C_6)$alkyl, halogen, —CN, —$CF_3$, —$NR_5R_{11}$, —$OR_5$, and —C(=O)$OR_5$, in which $R_5$ and $R_{11}$, which may be identical or different, are selected from hydrogen and $(C_1-C_6)$alkyl,
$R_3$ represents the group of formula:

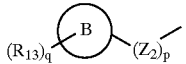

in which p is an integer from 0 to 4 inclusive,
$Z_2$ represents —$CR_{14}R_{15}$ wherein $R_{14}$ and $R_{15}$, independently of each other, represent a group selected from hydrogen and methyl, and when p is greater than or equal to 2, the hydrocarbon chain $Z_2$ optionally contains one double bond,
B represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl,
q is an integer from 0 to 7 inclusive,
the group(s) $R_{13}$, which may be identical or different, is (are) selected from $(C_1-C_6)$alkyl, halogen, —CN, —$CF_3$, —$NR_{16}R_{17}$, —$OR_{16}$, —$SO_2R_{16}$, —$(CH_2)_kSO_2NR_{16}R_{17}$, —$O(CH_2)_kC(=O)OR_{16}$, —$(CH_2)_kC(=O)OR_{16}$, —$O(CH_2)_kC(=O)NR_{16}R_{17}$, —$(CH_2)_kC(=O)NR_{16}R_{17}$, and —C(=O)O—$R_{19}$—$NR_{16}NR_{17}$ in which:
k is an integer from 0 to 3 inclusive,
$R_{16}$ and $R_{17}$, which may be identical or different, are selected from hydrogen and $(C_1-C_6)$alkyl,
$R_{19}$ represents a $(C_1-C_6)$alkylene group.

The invention also relates to a cyclized quinazoline of general formula (I) wherein n is equal to one.
The invention also relates to a cyclized quinazoline of general formula (I) wherein $Z_1$ represents a group —$CR_9R_{10}$ in which $R_9$ and $R_{10}$ represent each a hydrogen atom.
The invention also relates to a cyclized quinazoline of general formula (I) wherein A represents a 5- to 6-membered aromatic monocycle or a 3,4-methylenedioxyphenyl group optionally substituted by one or more groups $R_4$ as defined in the compound of formula (I).
The invention also relates to a cyclized quinazoline of general formula (I) wherein A represents a phenyl group optionally substituted by one group $R_4$ as defined in the compound of the formula (I).
The invention also relates to a cyclized quinazoline of general formula (I) wherein A represents a phenyl group, m is equal to one, and $R_4$ represents a methoxy group or a fluoro group.

The invention also relates to a cyclized quinazoline of general formula (I) wherein A represents a 4-pyridinyl group and if is equal to zero.
The invention also relates to a cyclized quinazoline of general formula (I) wherein Z represents a —NH group and Y represents an oxygen atom, optionally, its racemic forms, isomers thereof, N-oxydes thereof, and its the pharmaceutically acceptable salts thereof.
The invention also relates to a cyclized quinazoline of general formula (I) wherein W represents a —CH group and X represents a nitrogen atom.
The invention also relates to a cyclized quinazoline of general formula (I) wherein $R_3$ represent a group of formula:

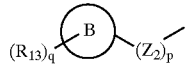

in which p is equal to one, $Z_2$ represents a methylene group, B represents a phenyl group, q is comprise between 0 to 1 inclusive, $R_{13}$ represents a group selected from —CN, —$(CH_2)_k$—C(=O)$OR_{16}$, —$(CH_2)_k$—C(=O)$NR_{16}R_{17}$, and —C(=O)O—$R_{19}$—$NR_{16}NR_{17}$ in which k, $R_{16}$, $R_{17}$, and $R_{19}$ are as defined in the compound of formula (I).

Among the groups defined above, the following substituents are particularly preferred:
halogen: F, Cl, Br and I, preferably F, Br and Cl,
$(C_1-C_6)$alkyl: linear or branched containing from 1 to 6 and preferably from 1 to 3 carbon atoms,
halo$(C_1-C_6)$alkyl: alkyl substituted with one or more halogen atoms, and preferably trihalogenomethyl,
$(C_1-C_6)$alkoxy: linear or branched containing from 1 to 6 and preferably from 1 to 3 carbon atoms,
$(C_2-C_6)$alkenyl: containing from 2 to 6 and preferably 2 or 4 carbon atoms, more particularly allyl,
$(C_2-C_6)$alkynyl: containing from 2 to 6 and preferably 2 or 4 carbon atoms, more particularly propargyl,
aryl: monocycle or bicycle containing from 5 to 10 and preferably 5 to 6 carbon atoms,
heteroaryl: aryl, as defined hereinbefore, in which one to four carbon atoms are remplaced by one to four heteroatoms selected from nitrogen, oxygen and sulphur. Examples of such groups containing a heteroatom are, inter alia, furyl, thienyl and pyridyl.
heterocycle: this term comprises the heteroaryl defined above, the heteroaryl partially hydrogenated and cycloalkyl in which one to four carbon atoms are remplaced by one to four heteroatoms selected from O, S and N.
aryl$(C_1-C_6)$alkyl in which the alkyl contains from 1 to 6 and preferably from 1 to 4 carbon atoms and the aryl contains from 5 to 10 and preferably 5 or 6 carbon atoms,
cycloalkyl: monocycle or bicycle containing from 3 to 10 and preferably from 3 to 6 carbon atoms,
cycloalkyl$(C_1-C_6)$alkyl in which the alkyl contains from 1 to 6 and preferably from 1 to 3 carbon atoms and the cycloalkyl contains from 3 to 10 carbon atoms,
a multiple bond represent a double bond or a triple bond between two carbon atoms.

Among the compounds that are preferred according to the present invention are the following compounds:
benzyl 4-benzyl-5-oxo-4H-[1,2,4]triazolo[4,3-a]quinazol-7-ylcarboxylate,
4-pyridylmethyl 4-benzyl-5-oxo-4H-[1,2,4]triazolo[4,3-a]quinazol-7-ylcarboxylate, N-(3,4-methylenedioxybenzyl)-4-benzyl-5-oxo-4H-[1,2,4]triazolo[4,3-a]quinazol-7-ylcarboxamide,
N-(4-pyridylmethyl)4-benzyl-5-oxo-4H-[1,2,4]triazolo[4,3-a]quinazol-7-ylcarboxamide,
N-(3,4-methylenedioxybenzyl)-4-benzyl-5-oxo-4H-imidazo[1,2-a]quinazol-7-ylcarboxamide,
N-(4-pyridylmethyl)-4-benzyl-5-oxo-4H-imidazo[1,2-a]quinazol-7-ylcarboxamide,
N-(4-methoxybenzyl)-4-benzyl-5-oxo-4,5-dihydro[1,2,4]triazolo[4,3-a]quinazoline-7-carboxamide,
N-[3-(4-pyridylsulphanyl)propyl]-4-benzyl-5-oxo-4,5-dihydro[1,2,4]triazolo-[4,3-a]quinazoline-7-carboxamide,
N-(3,4-Methylenedioxybenzyl)-4-(4-cyanobenzyl)-5-oxo-4H-[1,2,4]triazolo[4,3-a]quinazol-7-ylcarboxamide
Methyl 4-{7-[(1,3-benzodioxol-5-ylmethyl)-carbamoyl]-5-oxo-5H-[1,2,4]triazolo[4,3-a]quinazol-4-ylmethyl}benzoate
Methyl 4-{7-[(4-methoxybenzyl)-carbamoyl]-5-oxo-5H-[1,2,4]triazolo[4,3-a]quinazol-4-ylmethyl}benzoate
Methyl 4-{7-[(pyridin-4-ylmethyl)-carbamoyl]-5-oxo-5H-[1,2,4]triazolo[4,3-a]quinazol-4-ylmethyl}benzoate
(2-Dimethylamino-ethyl) 4-[7-(4-fluoro-benzylcarbamoyl)-5-oxo-5H-[1,2,4]triazolo[4,3-a]quinazol-4-ylmethyl]benzoate
4-(4-Dimethylcarbamoyl-benzyl)-5-oxo-4,5-dihydro-[1,2,4]triazolo[4,3-a]quinazoline-7-carboxylic acid 4-methoxy-benzylamide
N-(pyridin-4-ylmethyl)-4-(4-cyanobenzyl)-5-oxo-4H-[1,2,4]triazolo[4,3-a]quinazol-7-ylcarboxamide
Methyl (4-{7-[(1,3-benzodioxol-5-ylmethyl)-carbamoyl]-5-oxo-5H-[1,2,4]triazolo[4,3-a]quinazolin-4-ylmethyl}-phenyl)-acetate
Methyl (4-{7-[(4-methoxy)-benzylcarbamoyl]-5-oxo-5H-[1,2,4]triazolo[4,3-a]quinazolin-4-ylmethyl}-phenyl)-acetate
Methyl (4-{7-[(pyridin-4-yl)-methylcarbamoyl]-5-oxo-5H-[1,2,4]triazolo[4,3-a]quinazolin-4-ylmethyl}-phenyl)-acetate
N-(pyridin-4-ylmethyl)4-[3-(pyridin-4-yl)-2-propen-1-yl]-5-oxo-4H-[1,2,4]triazolo[4,3-a]quinazol-7-ylcarboxamide
4-[2-(4–Chloro-phenoxy)-ethyl]-5-oxo-4,5-dihydro-[1,2,4]triazolo[4,3-a]quinazoline-7-carboxylic acid 4-methoxy-benzylamide
4-{7-[(4-methoxybenzyl)-carbamoyl]-5-oxo-5H-[1,2,4]triazolo[4,3-a]quinazol-4-ylmethyl}benzoic acid
4-{7-[(1,3-benzodioxol-5-ylmethyl)-carbamoyl]-5-oxo-5H-[1,2,4]triazolo[4,3-a]quinazol-4-ylmethyl}benzoic acid
4-{7-[(pyridin-4-ylmethyl)-carbamoyl]-5-oxo-5H-[1,2,4]triazolo[4,3-a]quinazol-4-ylmethyl}benzoic acid
4-{7-[(4-fluoro)-benzylcarbamoyl]-5-oxo-5H-[1,2,4]triazolo[4,3-a]quinazol-4-ylmethyl}benzoic acid
(4-{7-[(4-methoxy)-benzylcarbamoyl]-5-oxo-5H-[1,2,4]triazolo[4,3-a]quinazolin-4-ylmethyl}-phenyl)-acetic acid
(4-{7-[(1,3-benzodioxol-5-ylmethyl)-carbamoyl]-5-oxo-5H-[1,2,4]triazolo[4,3-a]quinazolin-4-ylmethyl}-phenyl)-acetic acid, and
(4-{7-[(pyridin-4-yl)-methylcarbamoyl]-5-oxo-5H-[1,2,4]triazolo[4,3-a]quinazolin-4-ylmethyl}-phenyl)-acetic acid.

Among the compounds mentioned above, the following compounds are particularly preferred:
benzyl 4-benzyl-5-oxo-4H-[1,2,4]triazolo[4,3-a]quinazol-7-ylcarboxylate,
4-pyridylmethyl 4-benzyl-5-oxo-4H-[1,2,4]triazolo[4,3-a]quinazol-7-ylcarboxylate,
N-(3,4-methylenedioxybenzyl)-4-benzyl-5-oxo-4H-[1,2,4]triazolo[4,3-a]quinazol-7-ylcarboxamide,
N-(4-methoxybenzyl)-4-benzyl-5-oxo-4,5-dihydro[1,2,4]triazolo[4,3-a]quinazoline-7-carboxamide,
N-(3,4-Methylenedioxybenzyl)-4-(4-cyanobenzyl)-5-oxo-4H-[1,2,4]triazolo[4,3-a]quinazol-7-ylcarboxamide
Methyl 4-{7-[(1,3-benzodioxol-5-ylmethyl)-carbamoyl]-5-oxo-5H-[1,2,4]triazolo[4,3-a]quinazol-4-ylmethyl}benzoate
Methyl 4-{7-[(4-methoxybenzyl)-carbamoyl]-5-oxo-5H-[1,2,4]triazolo[4,3-a]quinazol-4-ylmethyl}benzoate
4-(4-Dimethylcarbamoyl-benzyl)-5-oxo-4,5-dihydro-[1,2,4]triazolo[4,3-a]quinazoline-7-carboxylic acid 4-methoxy-benzylamide
Methyl (4-{7-[(1,3-benzodioxol-5-ylmethyl)-carbamoyl]-5-oxo-5H-[1,2,4]triazolo[4,3-a]quinazolin-4-ylmethyl}-phenyl)-acetate
Methyl (4-{7-[(4-methoxy)-benzylcarbamoyl]-5-oxo-5H-[1,2,4]triazolo[4,3-a]quinazolin-4-ylmethyl}-phenyl)-acetate
4-{7-[(4-methoxybenzyl)-carbamoyl]-5-oxo-5H-[1,2,4]triazolo[4,3-a]quinazol-4-ylmethyl}benzoic acid
4-{7-[(1,3-benzodioxol-5-ylmethyl)-carbamoyl]-5-oxo-5H-[1,2,4]triazolo[4,3-a]quinazol-4-ylmethyl}benzoic acid
4-{7-[(pyridin-4-ylmethyl)-carbamoyl]-5-oxo-5H-[1,2,4]triazolo[4,3-a]quinazol-4-ylmethyl}benzoic acid
4-{7-[(4-fluoro)-benzylcarbamoyl]-5-oxo-5H-[1,2,4]triazolo[4,3-a]quinazol-4-ylmethyl}benzoic acid
(4-{7-[(4-methoxy)-benzylcarbamoyl]-5-oxo-5H-[1,2,4]triazolo[4,3-a]quinazolin-4-ylmethyl}-phenyl)-acetic acid
(4-{7-[(1,3-benzodioxol-5-ylmethyl)-carbamoyl]-5-oxo-5H-[1,2,4]triazolo[4,3-a]quinazolin-4-ylmethyl}-phenyl)-acetic acid, and
(4-{7-[(pyridin-4-yl)-methylcarbamoyl]-5-oxo-5H-[1,2,4]triazolo[4,3-a]quinazolin-4-ylmethyl}-phenyl)-acetic acid.

The invention also relates to the pharmaceutically acceptable salts of the compounds of formula (I). A review of the pharmaceutically acceptable salts will be found in J. Pharm. Sci., 1977, vol. 66:1–19. However, the expression "pharmacologically acceptable salts of a compound of formula (I) with a basic function" means the addition salts of the compounds of formula (I) formed from non-toxic mineral or organic acids such as, for example, the salts of hydrobromic acid, hydrochloric acid, sulphuric acid, phosphoric acid, nitric acid, acetic acid, succinic acid, tartaric acid, citric acid, maleic acid, hydroxymaleic acid, benzoic acid, fumaric acid, toluenesulphonic acid, isethionic acid and the like. The various quaternary ammonium salts of the compounds of formula (I) are also included in this category of compounds of the invention. In addition, the expression "pharmacologically acceptable salts of a compound of formula (I) with an acid function" means the usual salts of the compounds of formula (I) formed from non-toxic mineral or organic bases such as, for example, the hydroxides of alkali metals and of alkaline-earth metals (sodium, potassium, magnesium and calcium), amines (dibenzylethylenediamine, trimethylamine, piperidine, pyrrolidine, benzylamine and the like) or quaternary ammonium hydroxides such as tetramethylammonium hydroxide.

As mentioned above, the compounds of formula (I) of the present invention are matrix metalloprotease inhibitors, and particularly inhibitors of the enzyme MMP-13.

In this respect, their use is recommended in the treatment of diseases or complaints involving a therapy by MMP-13 inhibition. By way of example, the use of the compounds of the present invention may be recommended during the treatment of any pathology in which a destruction of the extracellular matrix tissue is involved, and most particularly pathologies such as rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary disease (COPD), age-related macular degeneration (ARMD) and cancer.

Selectivity of the Compounds of Formula (I) for the Enzyme MMP-13

Most of the matrix metalloprotease inhibitors described in the prior art are non-selective inhibitors, capable of simultaneously inhibiting several matrix metalloproteases. For example, compounds such as CGS-27.023A and AG-3340 (Montana and Baxter (2000)) simultaneously inhibit MMP-1, MMP-2, MMP-3, MMP-9 and MMP-13, i.e. these compounds of the prior art simultaneously inhibit MMPs of collagenase, gelatinase and stromelysin type.

It has been shown according to the invention that the compounds of general formula (I) constitute selective MMP-13 inhibitors.

The expression "selective inhibitor" of MMP-13 means a compound of formula (I) whose IC50 value for MMP-13 is at least 5 times lower than the IC50 value measured for a matrix metalloprotease other than MMP-13, and preferably at least 10 times, 15 times, 20 times, 30 times, 40 times, 50 times, 100 times or 1000 times lower than the IC50 value measured for a matrix metalloprotease other than MMP-13.

The expression "matrix metalloprotease other than MMP-13" preferably means an MMP selected from from MMP-1, MMP-2, MMP-3, MMP-7, MMP-9, MMP-12 and MMP-14.

In particular, it has been shown according to the invention that the compounds of general formula (I), and more particularly the family of compounds given as examples in the present description, have an IC50 value for the enzyme MMP-13 which is generally 1000 times less than the value of their IC50 for other matrix metalloproteases, in particular MMP-1, MMP-2, MMP-3, MMP-7, MMP-9, MMP-12 and MMP-14.

The result of this is that the compounds of general formula (I) according to the invention are particularly useful for treating complaints mainly associated with a physiological imbalance between the MMP-13 enzymes and their natural tissue inhibitors.

Pharmaceutical Formulation of the Compounds of the Invention

A subject of the present invention is also a pharmaceutical composition comprising a compound of general formula (I) as defined above and a pharmaceutically acceptable excipient.

The invention also relates to the use of a compound of general formula (I) as defined above for the preparation of a medicinal product intended for treating a disease or complaint involving therapy by inhibition of matrix metalloproteases, and more particularly a disease or complaint involving therapy by inhibition of type-13 matrix metalloprotease (MMP-13).

An MMP-13-inhibitor compound of general formula (I) according to the invention is particularly useful for treating all pathologies brought about by a degradation of the extracellular matrix tissue, and more particularly for treating rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases (COPDs), age-related macular degeneration (ARMD) and cancer.

In an entirely preferred manner, a compound of general formula (I) as defined according to the invention will be used to treat arthritis, osteoarthritis and rheumatoid arthritis.

The compounds of the invention are administered in the form of compositions that are suitable for the nature and gravity of the complaint to be treated. The daily dosage in man is usually between 2 mg and 1 g of product which may be absorbed in one or more dosage intakes. The compositions are prepared by methods that are common to those skilled in the art and generally comprise 0.5% to 60% by weight of active principle (compound of formula I) and 40% to 99.5% by weight of pharmaceutically acceptable vehicle.

The compositions of the present invention are thus prepared in forms that are compatible with the desired route of administration. By way of example, the following pharmaceutical forms may be envisaged, although the list given below is not limiting:

1) Forms for Oral Administration:

Drinkable solutions, suspensions, sachets of powder for drinkable solution, sachets of powder for drinkable suspension, gastro-resistant gel capsules, sustained-release forms, emulsions, HPMR capsules or gel capsules, or lyophilizates to be melted under the tongue.

2) Forms for Parenteral Administration:

Intravenous Route:

Aqueous solutions, water/cosolvent solutions, solutions using one or more solubilizing agents, colloidal suspensions, emulsions, nanoparticulate suspensions which can be used for the injection of sustained-release forms, dispersed forms and liposomes.

Subcutaneous/intramuscular Route:

In addition to the forms which can be used intravenously and which can also be used for the subcutaneous and intramuscular routes, other types of forms such as suspensions, dispersed forms, sustained-release gels and sustained-release implants may also be used.

3) Forms for Topical Administration:

Among the most common topical forms that are distinguished are creams, gels (aqueous phases gelled with polymers), patches, which are dressings to be stuck directly onto the skin and which can be used to treat dermatosis without percutaneous penetration of the active substance, sprays, emulsions and solutions.

4) Forms for Pulmonary Administration

Forms such as solutions for aerosols, powders for inhalers and other suitable forms are distinguished in this category.

5) Forms for Nasal Administration:

This especially relates herein to solutions for drops.

6) Forms for Rectal Administration:

Suppositories and gels will be selected, inter alia.

It is also possible to envisage using forms allowing the administration of ophthalmic solutions or allowing the vaginal administration of the active principle.

Another important category of pharmaceutical form which may be used in the context of the present invention relates to forms for improving the solubility of the active principle. By way of example, it may be envisaged to use aqueous solutions of cyclodextrin, and more particularly forms comprising hydroxypropyl-β-cyclodextrin. A detailed review of this type of pharmaceutical form is presented in the article published under the reference Journal of Pharmaceutical Sciences, 1142–1169, 85, (11), 1996, and incorporated into the present patent application by reference.

The various pharmaceutical forms recommended above are described in detail in the book "Pharmacie galénique" by A. Lehir (published by Masson, 1992 (6th edition)), which is incorporated into the present patent application by reference.

Processes for Synthesizing Intermediate Compounds that are Useful for Manufacturing a Cyclized Quinazoline of Formula (I)

A. First Process

This process makes it possible to achieve the synthesis of intermediate compounds that are useful in the manufacture of the compounds of general formula (I) in which W is C—$R_1$, X is N and $R_1$, $R_3$, $R_4$, Y, Z, $Z_1$, n, m and A are as defined more generally in the present description.

This process is illustrated in Scheme 1 below:

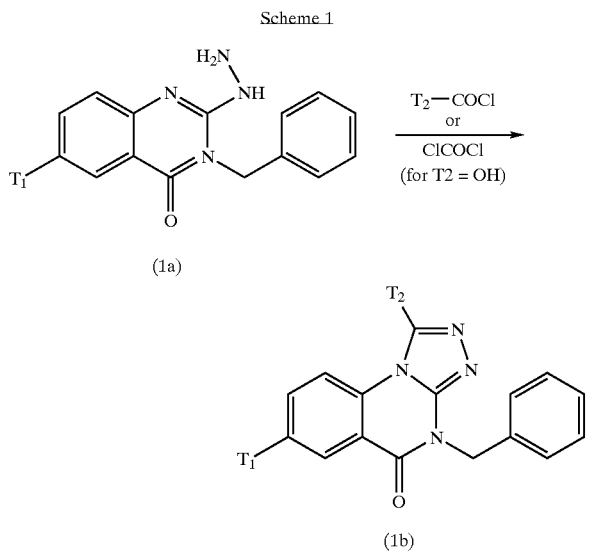

In Scheme 1 above, $T_1$ represents an exchangeable group, for example bromine, or a protecting group such as, for example, COOEt, and $T_2$ represents a group selected from aryl, alkyl and cycloalkyl.

In this process, the 2-hydrazino 3,4-dihydroquinazolin-4-one (1a) is coupled, in a first stage, with an alkylcarboxylic, cycloalkylcarboxylic or arylcarboxylic acid chloride (or optionally a phosgene derivative) to give the corresponding hydrazide intermediate, which is cyclized, in a second stage, into a 1-alkyl, cycloalkyl or aryl (or optionally hydroxyl) triazolo[4,3-a]quinazolin-5-one (1b), by heating in a suitable solvent. It is clearly understood that the acid chloride reagent $T_2$-COCl may be replaced with a reactive derivative of the acid, such as an orthoester.

The process for synthesizing intermediate compounds (1a) is disclosed in the PCT patent application published under No. WO 00/66584.

B. Process 2

This process also constitutes a method for synthesizing intermediates that are useful in the manufacture of compounds of formula (I) in which W is C—$R_1$, X is N and $R_1$, $R_3$, $R_4$, Y, Z, $Z_1$, n, m and A are as defined more generally in the present description.

This process is illustrated in Scheme 2 below:

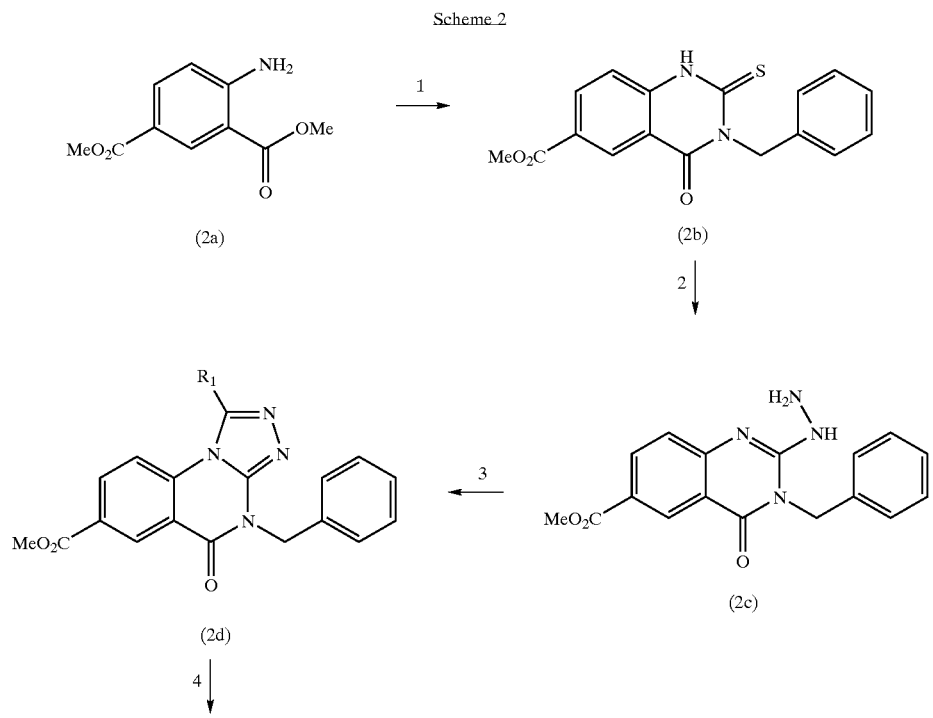

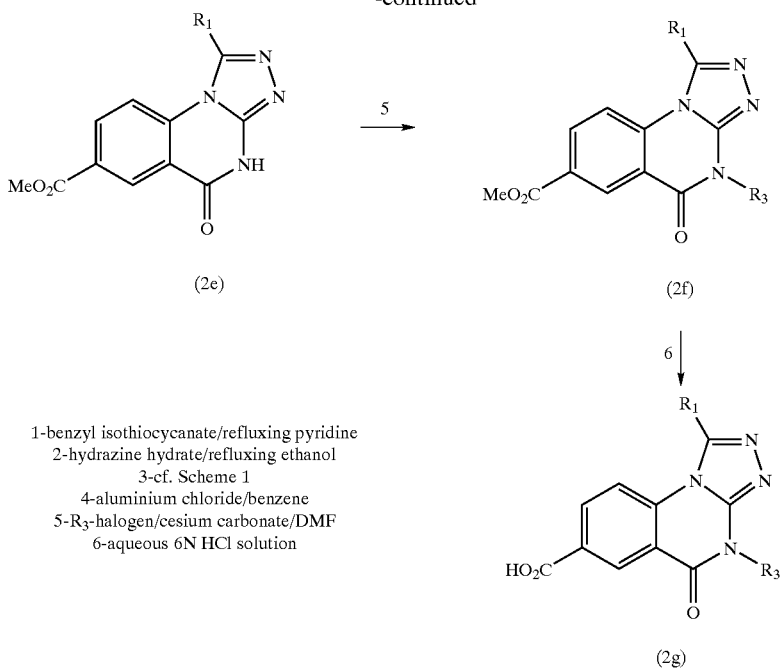

(2e) → (2f) → (2g)

1-benzyl isothiocycanate/refluxing pyridine
2-hydrazine hydrate/refluxing ethanol
3-cf. Scheme 1
4-aluminium chloride/benzene
5-R₃-halogen/cesium carbonate/DMF
6-aqueous 6N HCl solution Methyl 4-aminoisophthalate (2a) is treated with benzyl isothiocyanate, in a solvent such as pyridine or acetic acid, to give 3-benzyl-6-(methoxycarbonyl)-2-thioxo-1,2,3,4-tetrahydroquinazolin-4-one (2b). This compound is heated, in a refluxing alcohol, in the presence of hydrazine hydrate to give the corresponding hydrazine which is in turn cyclized by reaction with a carboxylic acid derivative R1COOH (such as an acid chloride or an orthoester). The 4-benzyl-7-(methoxycarbonyl)-4,5-dihydrotriazolo[4,3-a]quinazolin-5-one (2d) obtained is N4-debenzylated using aluminium chloride in benzene, and the intermediate secondary lactam is then substituted with a halide, in the presence of a base such as cesium carbonate, in a solvent such as dimethylformamide. The N-substituted analogue obtained (2f) is then hydrolysed, preferably in acidic medium, to give the corresponding acid (2g) which may be subsequently subjected to a coupling reaction of peptide type.

The order of the steps in the above process may be modified for the synthesis of certain compounds. For example, when $R_3$ is para-cyanobenzyl, step 5 will be carried out last since the para-cyanobenzyl group would not withstand the conditions of step 6.

C. Process 3

This process allows the preparation of intermediate compounds that are useful for manufacturing compounds of formula (I) in which W is C—$R_1$, X is C—$R_2$ and $R_1$, $R_2$, $R_3$, $R_4$, Y, Z, $Z_1$, n, m and A are as defined more generally in the present description.

This preparation process is illustrated in Scheme 3 below:

Scheme 3

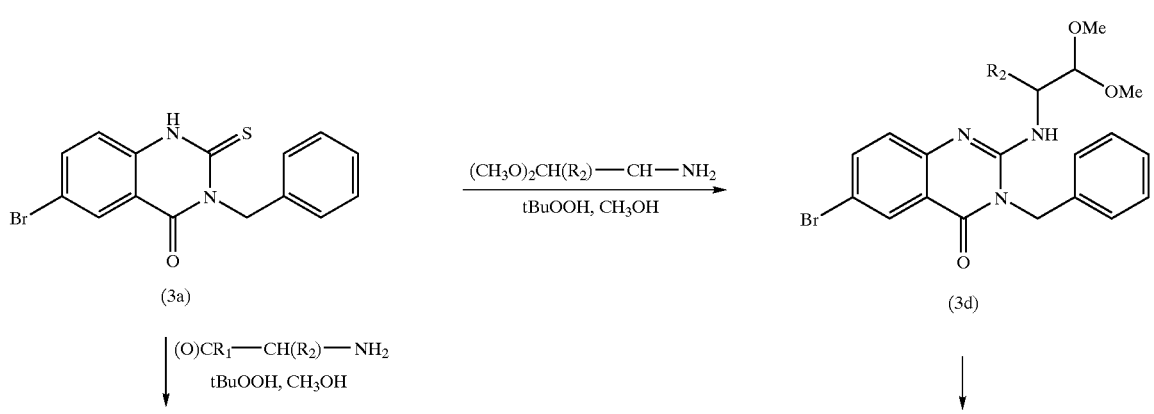

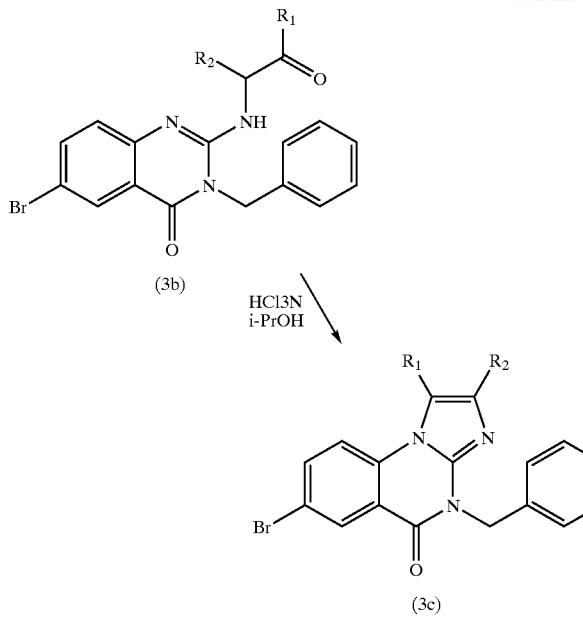

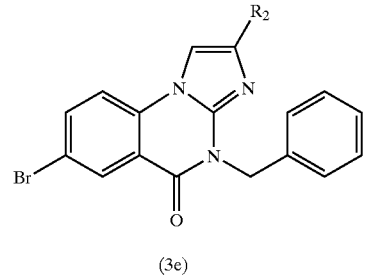

3-Benzyl-6-bromo-2-thioxo-1,2,3,4-tetrahydroquinazolin-4-one (3a) is treated, depending on the case, with a 2-amino acetal or a 2-amino ketone, in an alcoholic solvent such as methanol or ethanol, in the presence of a peroxide for initiating the oxidation of the starting thiol and converting it, depending on the circumstance, into a better exchangeable group. The intermediate amino ketone (3d) or amino acetal (3b) obtained is readily cyclized in the presence of acid, in an alcoholic solvent such as isopropanol, into 4-benzyl-6-bromo-4,5-dihydroimidazolo[1,2-a]quinazolin-5-one (3c) or (3e) depending on the desired degree of substitution. The bromine atom in position 7 may then be subsequently exchanged with a potential carboxylic function (see, for example, Scheme 5).

D. Process 4

This process allows the synthesis of intermediate compounds that are useful for preparing compounds of formula (I) in which W is N, X is C—$R_2$ and $R_2$, $R_3$, $R_4$, Y, Z, $Z_1$, n, m and A are as defined more generally in the present description.

This process is illustrated in Scheme 4 below:

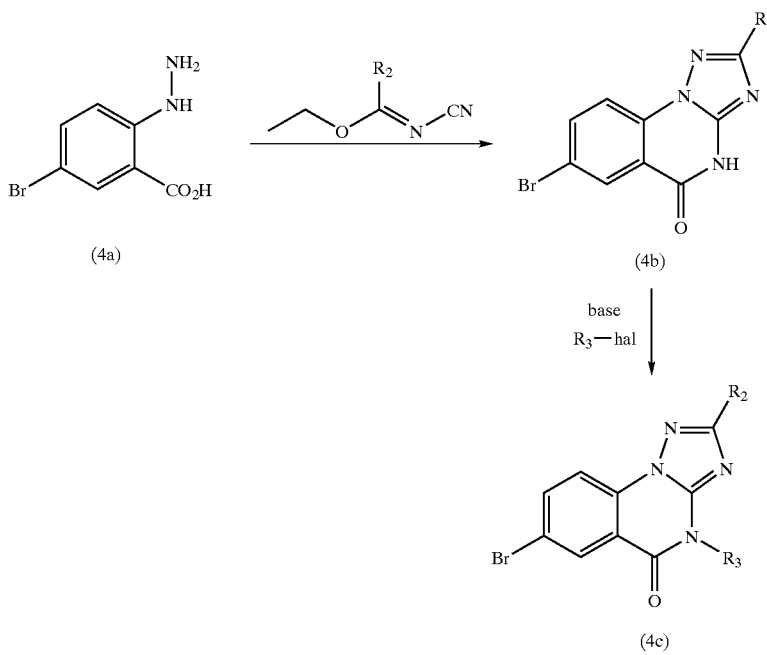

5-Bromo-2-hydrazinobenzoic acid (4a) is treated with an alkyl N-cyanoimidate to give the 4-benzyl-6-bromo-4,5-dihydrotriazolo[2,3-a]quinazolin-5-one (4b) in a single step. This compound is substituted with a halide, in the presence of a base such as cesium carbonate, in a solvent such as dimethylformamide, to give the N4-substituted analogue (4c). The bromine atom in position 7 may then be subsequently exchanged with a potential carboxylic function (see, for example, Scheme 5).

E. Process 5

This process illustrates a preferred embodiment of intermediate steps for synthesizing a compound of formula (I) according to the invention, by which the substituent $R_3$ is introduced into some of the intermediate compounds whose preparation is illustrated by Processes 1 to 4 described above or by Scheme 5 below.

This process for synthesizing intermediate compounds in the manufacture of the compounds of formula (I) according to the invention is illustrated in Scheme 5 below.

Scheme 5

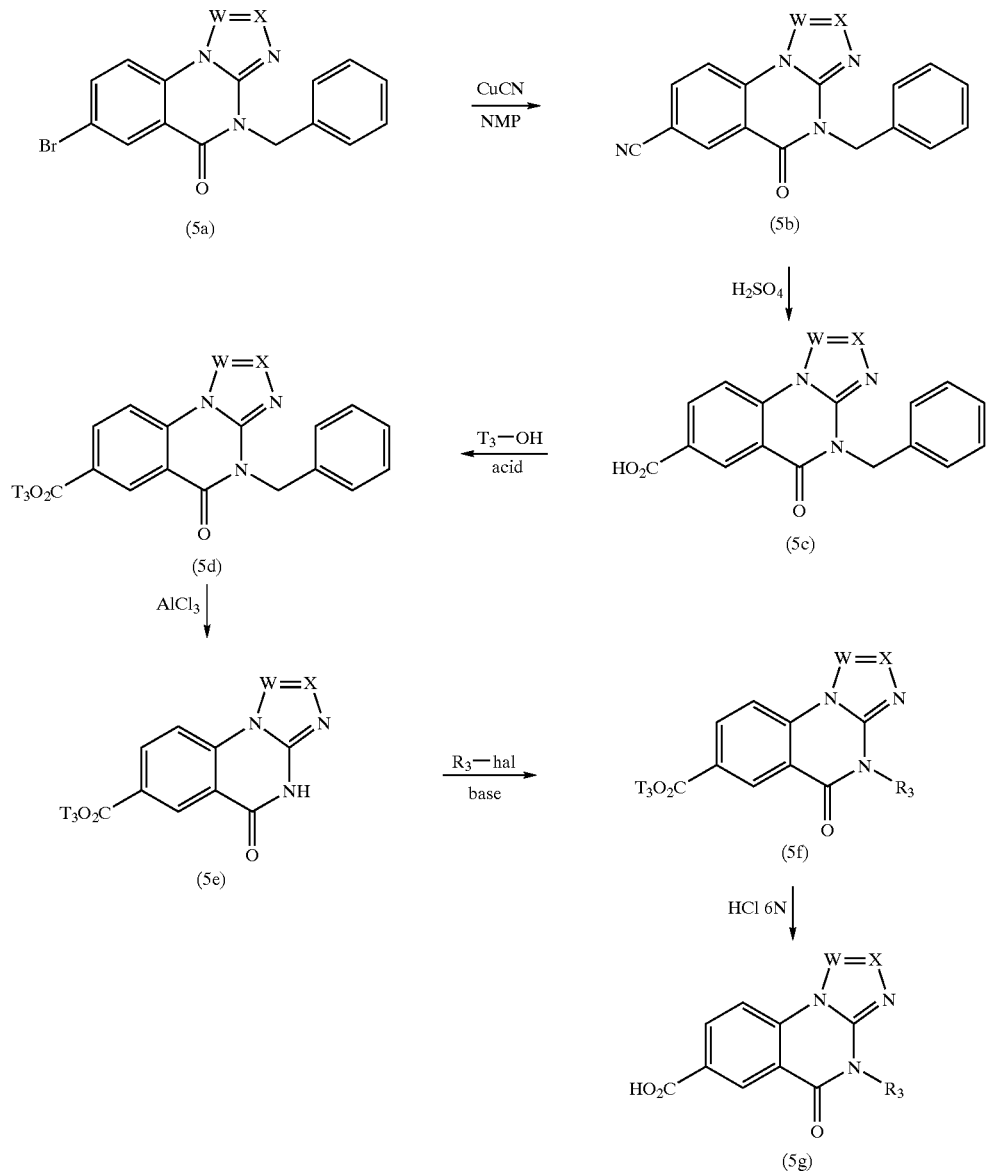

In Scheme 5 above, $T_3$ represents a $(C_1-C_6)$alkyl.

4-Benzyl-7-bromo-4,5-dihydrotriazolo[4,3-a]quinazolin-5-one, triazolo[2,3-a]quinazolin-5-one or imidazo[4,3-a]quinazolin-5-one (5a) is converted into the corresponding 7-cyano derivative (5b) by an exchange reaction with copper cyanide, in a solvent such as N-methylpyrrolidinone. The nitrile function is hydrolysed in acidic medium, for example in the presence of sulphuric acid, and the carboxylic acid (5c) obtained is then esterified to (5d) with an alcohol in acidic medium. This intermediate is then N4-debenzylated with aluminium chloride, in a solvent such as benzene, and substituted with a halide to give compound (5f), in the presence of a base such as sodium hydride or cesium carbonate, in a solvent such as dimethylformamide or N-methylpyrrolidinone.

The ester (5f) is finally hydrolysed, in acidic medium, to a corresponding carboxylic acid (5g).

The first two steps of Scheme 5 above also apply to the intermediates described above into which R3 has already been introduced.

F. Process 6

This process allows the synthesis of intermediate compounds that are useful for manufacturing compounds of formula (I) in which W is N, X is N and $R_3$, $R_4$, Y, Z, $Z_1$, n, m and A are as defined more generally in the present description.

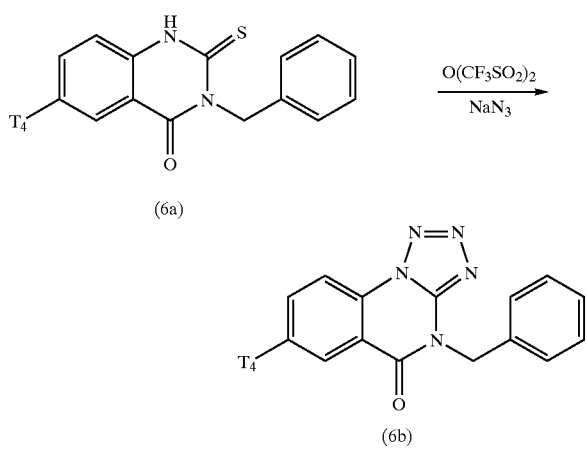

The process for synthesizing intermediate compounds (6a) is disclosed in the PCT patent application published under WO 00/66584.

The group $T_4$ represents a protecting group such as $CO_2Me$ or an exchangeable group such as a halogen.

The quinazolin-4-one (6a) may be converted into the 4,5-dihydrotriazolo[4,5-a]quinazolin-5-one (6b) by the action of triflic anhydride and sodium azide in a solvent such as acetonitrile.

Instead of the reagents indicated, phosphorus pentachloride and trimethylsilyl azide may also be used to carry out this cyclization.

Processes for Synthesizing the Compounds of Formula (I).

A. Process 1

This process allows the synthesis of compounds of formula (I) in which Y is an oxygen and W, X, $R_3$, $R_4$, Z, $Z_1$, n, m and A are as defined more generally in the present description.

This first process for synthesizing compounds of formula (I) is illustrated in Scheme 7 below:

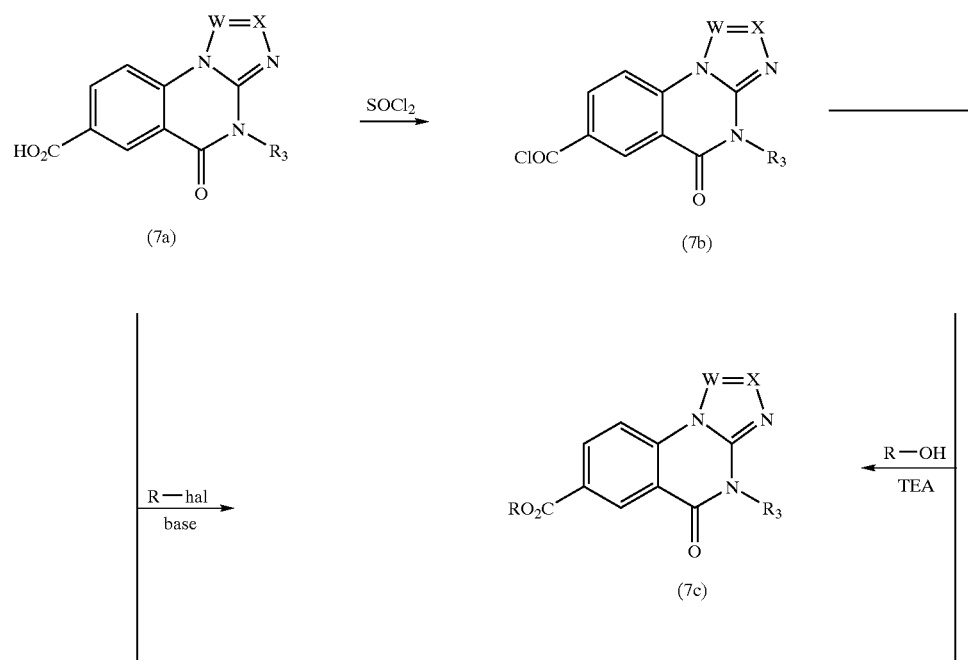

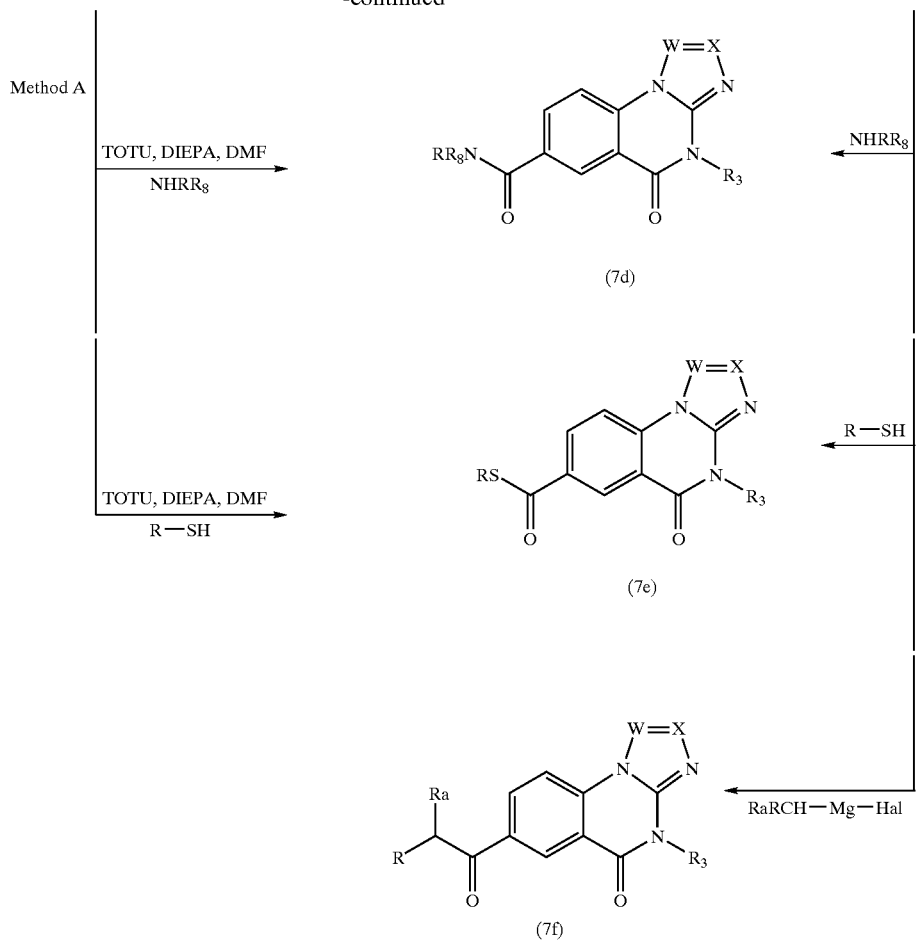

(7d)

(7e)

(7f)

In Scheme 7 above, hal represents a halogen, $R_8$ represents a hydrogen, a $(C_1-C_6)$alkyl, an aryl$(C_1-C_6)$alkyl, a cycloalkyl, an aryl or a heteroaryl, Ra represents a hydrogen, a $(C_1-C_6)$alkyl, an aryl, an aryl$(C_1-C_6)$alkyl, an aromatic or non-aromatic heterocycle or a cycloalkyl, and R represents the group

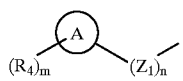

in which A, $R_4$, $Z_1$, m and n are as defined in the compound of general formula (I).

4-Benzyl-7-bromo-4,5-dihydrotriazolo[4,3-a]quinazolin-5-one, triazolo[2,3-a]quinazolin-5-one or imidazo[4,3-a]quinazolin-5-one (5a) bearing an R3 substitution in position 4 (7a) may be converted into the corresponding ester (7c) or amide (7d) by the direct method A, i.e. coupling with a halide in the presence of a base or activation of the acid function, for example with TOTU, in the presence of DIPEA, followed by displacement of the activated function with an amine; the ester (7c), the amide (7d), the thio acid (7e) or the ketone (7f) may also be obtained by an indirect method B: the acid is converted into the acid chloride (7b) by reaction with thionyl chloride and this compound is then reacted either with an alcohol to give the ester (7c), or with an amine to give the amide (7d), or with a thiol to give the thio ester (7e), or with an organomagnesium reagent to give the ketone (7f).

B. Synthetic Process 2

The second preferred process for synthesizing a compound of formula (I) according to the invention allows the manufacture of compounds of formula (I) in which Y is S and WI X, $R_3$, $R_4$, Z, $Z_1$, m, n and A are as defined more generally in the present description.

This process consists essentially in reacting a compound of formula (I) in which Y is O with a suitable reagent, for example Lawesson's reagent.

The said process is illustrated in Scheme 8 below:

Scheme 8

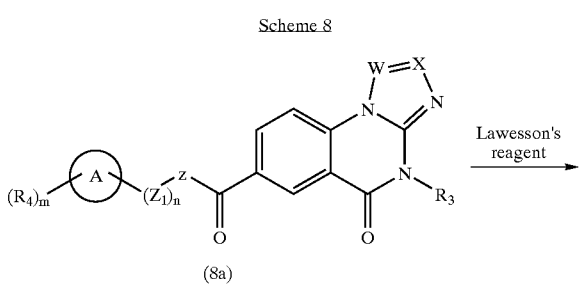

(8a)

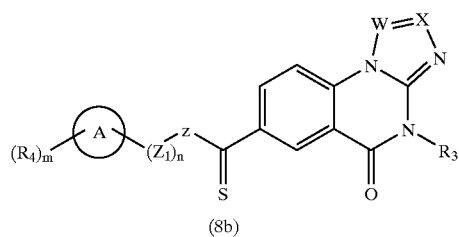

(8b)

4,5-Dihydrotriazolo[4,3-a]quinazolin-5-one, triazolo[2,3-a]quinazolin-5-one or imidazolo[4,3-a]quinazolin-5-one bearing an oxygenated function in position 7 (8a; Z=C, O, N) may be converted into the sulphur-containing analogue (8b) by reaction with a reagent such as $P_2S_5$ or Lawesson's reagent.

C. Synthetic Process 3

According to this third process for synthesizing a compound of formula (I), a compound of formula (I) is prepared in which Y is NH, Z is O, N or S and W, X, $R_3$, $R_4$, $Z_1$, m, n and A are as defined more generally in the present description.

This third process for synthesizing compounds of formula (I) is illustrated in Schemes 9 and 10 below:

In the above scheme, hal represents a halogen atom and $R_8$ represents a hydrogen, a $(C_1-C_6)$alkyl, an aryl$(C_1-C_6)$alkyl, a cycloalkyl, an aryl or a heteroaryl.

4,5-Dihydrotriazolo[4,3-a]quinazolin-5-one, triazolo[2,3-a]quinazolin-5-one or imidazo[4,3-a]quinazolin-5-one bearing a nitrile function in position 7 (9a) may be converted into the corresponding imidate (9b) by addition of an alcohol R—OH to the nitrile function, into the corresponding amidine (9c) by addition of an amine R—NH—$R_8$ to the nitrile function, into the thioimidate by addition of a thiol R—SH to the nitrile function, or into the imine by addition of an organomagnesium reagent.

The compounds obtained after the process described in Scheme 9 may be reacted with a group R—X in which R is a $(C_1-C_6)$alkyl and X is an exchangeable group such as a halogen, in the presence of a base, to give a compound of general formula (I) in which Y is N—R.

Scheme 9

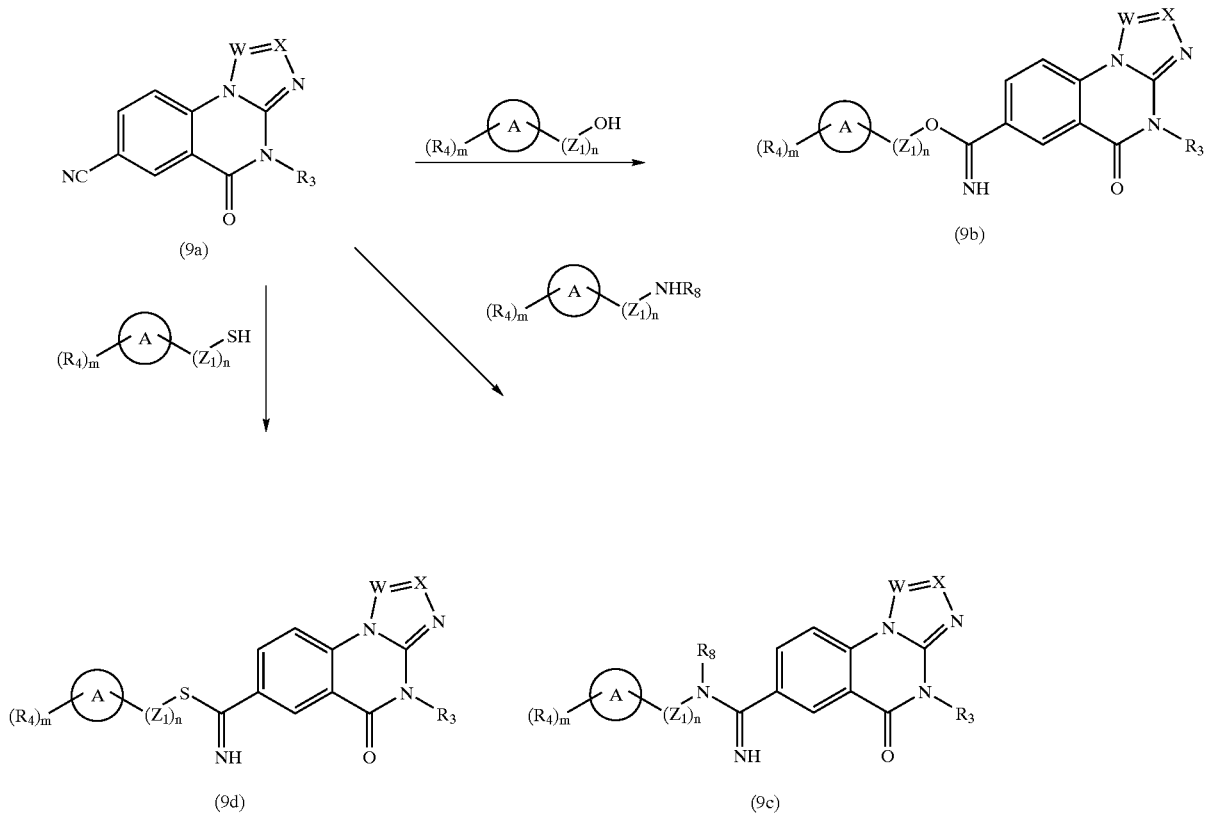

Scheme 10

In the above scheme, R represents a lower alkyl and Ra represents a hydrogen, a lower alkyl, an aryl, an aralkyl, an aromatic or non-aromatic heterocycle or a cycloalkyl.

The present invention is also illustrated, without, however, being limited thereto, by the examples which follow:

EXAMPLES

Example 1

Benzyl 4-benzyl-5-oxo-4H-[1,2,4]triazolo[4,3-a]quinazol-7-ylcarboxylate
Intermediate of General Formula (5b)
1,2,3,4-Tetraydro-4-benzyl-7-cyano-4H-1,2,4]triazolo[4,3-a]quinazolin-5-one.

26.5 g (0.08 mol) of 1,2,3,4-tetrahydro-4-benzyl-7-bromo-4H-[1,2,4]triazolo[4,3-a]quinazolin-5-one (intermediate of general formula (5a)) and 12.15 g (0.14 mol) of copper cyanide are placed in 250 ml of N-methylpyrrolidinone in a reactor fitted with a stirring system and a condenser equipped with a potassium hydroxide guard tube. The mixture obtained is stirred and gradually heated to 220° C. and this temperature is then maintained for 3 hours. After partial cooling, the solvent is evaporated off under vacuum; the residue obtained is partitioned between dilute aqueous ammonia and methylene chloride, and the insoluble material in the two phases is removed by filtration after washing several times with aqueous ammonia and methylene chloride. The organic phase is separated out after settling has taken place, washed with saturated sodium chloride solution, dried over sodium sulphate and then concentrated under vacuum. The residual solid is taken up in 50 ml of ethanol and the insoluble material is spin-filtered and dried under vacuum to give 15.75 g, which is pure by TLC.

The $^1$H NMR spectrum is compatible with the expected structure.
Yield=65%
TLC (CH2Cl2 95/CH3OH 5): Rf=0.75.
Intermediate of General Formula (5c)
1,2,3,4-Tetrahydro-4-benzyl-4H-[1,2,4]triazolo[3-a]5-oxo-quinazolin-7-ylcarboxylic acid.

A solution of 150 ml of concentrated sulphuric acid in 150 ml of water is prepared, in a round-bottomed flask fitted with a stirrer and a condenser, while cooling externally with an ice bath. 7.0 g (0.023 mol) of 1,2,3,4-tetrahydro-4-benzyl-7-cyano-4H-[1,2,4]triazolo[4,3-a]quinazolin-5-one (intermediate of general formula (5b)) are added and the mixture is then refluxed with stirring for 2 h 30 min. After cooling, the mixture is filtered and 500 ml of ice-cold water are added to the acidic solution obtained. The precipitate is filtered off, washed several times with water to neutral pH and dried under vacuum to give 5.1 g of solid.

The $^1$H NMR spectrum is compatible with the expected structure.
Yield=69%.

The synthesis of Example 1 was carried out according to the 2 methods described in Scheme 7:
Method A 0.64 g (0.002 mol) of 1,2,3,4-tetrahydro-4-benzyl-4H-[1,2,4]triazolo[4,3-a]5-oxoquinazolin-7-ylcarboxylic acid are placed in 100 ml of DMF in a reactor equipped with a condenser and a magnetic stirrer. 0.276 g (0.002 mol) of K$_2$CO$_3$ is added and the mixture is stirred at room temperature for 30 minutes.

0.342 g (0.002 mol) of benzyl bromide is then added and the mixture is heated to 100° C. and then stirred at this temperature for 15 hours. After evaporating off the solvent under vacuum, the residue is taken up in a mixture of water and ethyl acetate; the insoluble solid in the 2 phases is filtered off, washed with water and an additional small amount of ethyl acetate and then dried under vacuum to give 0.45 g of crude compound (55% of the theoretical amount).

This product is purified by chromatography on a column of silica, eluting with a CH$_2$Cl$_2$ 99/CH$_3$OH 1 mixture: 0.2 g of compound, which is pure by TLC, is obtained.

A recrystallization from acetonitrile gives colourless crystals with a melting point of:
m.p. (Tottoli)=221° C.
TLC(CH$_2$Cl$_2$ 98/CH$_3$OH 2): Rf=0.4
$^1$H NMR δ (ppm) [DMSO]: 5.4 (s, 2H); 5.45 (s, 2H); 7.3–7.55 (m, 10H); 8.35 (d, 1H); 8.5 (d, 1H); 8.75 (s, 1H); 9.6 (s, 1H).
Elemental analysis (%):
Calculated: C70.23; H4.42; N13.65; O11.69.
Found: C69.81; H4.32; N13.58; O11.92.
Method B 0.24 g (0.00075 mol) of 4-benzyl-4H-[1,2,4]triazolo[4,3-a]-5-onequinazol-7-ylcarboxylic acid is placed in suspension in 15 ml of CHCl$_3$ in a reactor fitted with a stirring system, a condenser and a nitrogen inlet, followed by dropwise addition, with stirring at room temperature, of 0.35 ml (0.0045 mol) of thionyl chloride. The mixture is then heated, with stirring, at the reflux temperature of the reagent for 3 hours. After total evaporation of the excess thionyl chloride under vacuum, a solution of 0.116 ml (0.0011 mol) of benzyl alcohol and 0.17 ml (0.0011 mol) of triethylamine in 15 ml of CHCl$_3$ is added and stirring is then continued at room temperature for 1 hour.

The organic phase is washed with water, separated from the aqueous phase by settling and dried over sodium sulphate. After evaporating off the solvent under vacuum, the crude product obtained is purified by chromatography on a column of silica, eluting with a CH$_2$Cl$_2$ (99)/CH$_3$OH (1) mixture to give 0.1 g of compound, which is pure by TLC (Rf=0.4; eluent: CH$_2$Cl$_2$ 98/CH$_3$OH 2).
Yield: 33%.

Example 2

4-Pyridylmethyl 4-benzyl-5-oxo-4H-[1,2,4]triazolo[4,3-a]quinazol-7-ylcarboxylate The compound of Example 2 is prepared according to the method described in Example 1, using 4-bromomethylpyridine in step A.

Yield=46%.

m.p. (Tottoli)=232° C.

$^1$H NMR δ (ppm) [DMSO]: 5.4 (s, 2H); 5.5 (s, 2H); 7.25–7.4 (m, 3H); 7.45–7.55 (m, 4H); 8.4 (d, 1H); 8.55 (d, 1H); 8.65 (d, 2H); 8.8 (s, 1H); 9.65 (s, 1H).

Example 3

N-(3,4-Methylenedioxybenzyl)-4-benzyl-5-oxo-4H-[1,2,4]triazolo[4,3-a]quinazol-7-ylcarboxamide 0.32 g (0.001 mol) of 4-benzyl-5-oxo-4H-[1,2,4]triazolo[4,3-a]quinazol-7-ylcarboxylic acid is dissolved in 15 ml of dry DMF in a reactor protected from moisture, equipped with a stirring system and a thermometer. 0.124 ml (0.001 mol) of 3,4-methylenedioxybenzylamine and 0.328 g (0.001 mol) of TOTU are then added, the mixture is stirred, the solution obtained is cooled to 0–5° C. and 0.258 mg (0.002 mol) of DIPEA is then added. The solution is stirred under cold conditions for a few minutes and then at room temperature for 15 hours.

After evaporating off the solvent under vacuum, the residue is taken up in methylene chloride and the insoluble material is separated out by filtration, washed with a small additional amount of $CH_2Cl_2$ and then dried under vacuum to give 0.35 g of crude compound (77% of theoretical amount).

0.3 g of this product is recrystallized from dioxane to give 0.15 g of product which is pure by TLC.(Rf=0,35; eluent: $CH_2Cl_2$ (80)/$CH_3OH$ (20)).

m.p. (Tottoli)=273° C. (dec).

$^1$H NMR δ (ppm) [DMSO]: 4.45 (d, 2H); 5.45 (s, 2H); 6.0 (s, 2H); 6.8–7.0 (m, 3H); 7.25–7.4 (m, 3H); 7.5 (m, 2H); 8.3 (d, 1H); 8.4 (d, 1H); 8.8 (s, 1H); 9.35 (t, 1H); 9.6 (s, 1H).

Example 4

N-(4-Pyridylmethyl)-4-benzyl-5-oxo-4H-[1,2,4]triazolo[4,3-a]quinazol-7-ylcarboxamide The compound of Example 4 is prepared in the same way as in Example 3, but using 4-pyridylmethylamine.

Yield=50%.

m.p. (Tottoli)=273° C.

$^1$H NMR δ (ppm) [DMSO]: 4.5 (d, 2H); 5.4 (d, 2H); 7.3–7.4 (m, 5H); 7.5 (m, 2H); 8.35 (d, 1H); 8.45 (d, 1H); 8.5 (d, 2H); 8.8 (s, 1H); 9.5 (t, 1H); 9.6 (s, 1H).

Example 5

N-(3,4-methylenedioxybenzyl)-4-benzyl-5-oxo-4H-imidazo[1,2-a]quinazol-7-ylcarboxamide Intermediate of General Formula (3d)

1,2,3,4-Tetrahydro-3-benzyl-6-bromo-2-[N-(2,2-dimethoxyethyl)imino]-4H-quinazolin-4-one.

6.4 g (0.0184 mol) of 1,2,3,4-tetrahydro-3-benzyl-6-bromo-2-thioxo-4H-quinazolin-4-one, 10.1 ml (0.092 mol) of 2-aminoacetaldehyde dimethyl acetal and 8.3 ml (0.0645 mol) of aqueous 70% t-butyl hydroperoxide are placed in 575 ml of dry methanol in a round-bottomed flask equipped with a stirrer and a condenser fitted with a potassium hydroxide guard tube. The suspension is stirred at room temperature for 24 h. Aqueous potassium metabisulphite solution is added to neutralize any residual excess of peroxides, and the mixture is then concentrated to a small volume. The precipitate is filtered off, washed with water and then with methanol, and dried under vacuum.

2.53 g of a crude solid are obtained, which product is used in its current form for the next step. The $^1$H NMR spectrum is compatible with the expected structure.

Yield=33%.

Intermediate of General Formula (3e)

1,2,3,4-Tetrahydro-4-benzyl-7-bromo-4H-imidazo[1,2-a]quinazolin-5-one.

2.87 g (0.0067 mol) of 1,2,3,4-tetrahydro-3-benzyl-6-bromo-2-[N-(2,2-dimethoxyethyl)imino]-4H-quinazolin-4-one (intermediate of general formula (3d)) are dissolved in a mixture of 20 ml of 3N hydrochloric acid solution and 70 ml of isopropanol in a round-bottomed flask equipped with a stirrer and a condenser. The solution is refluxed for 4 h with stirring. The isopropanol is evaporated off under vacuum and the residue is partitioned between sodium bicarbonate solution and methylene chloride. The organic phase is separated out after settling has taken place, washed with saturated sodium chloride solution, dried over sodium sulphate and then concentrated to dryness to give 2.1 g of crude compound.

The $^1$H NMR spectrum is compatible with the expected structure.

Yield=88%.

Intermediate of General Formula (5b)

1,2,3,4-Tetrahydro-4-benzyl-7-cyano-4H-imidazo[1,2-a]quinazolin-5-one.

2.4 g (0.0068 mol) of 1,2,3,4-tetrahydro-4-benzyl-7-bromo-4H-imidazo[1,2-a]quinazolin-5-one are treated with 1.1 g (0.0123 mol) of copper cyanide in 25 ml of N-methylpyrrolidinone, according to the process for synthesizing the intermediate of general formula (5b). The crude residue obtained is purified by chromatography on silica, eluting with a $CH_2Cl_2$ 98.5/$CH_3OH$ 1.5 mixture. 1.15 g of a coloured solid are obtained.

The $^1$H NMR spectrum is compatible with the expected structure.

Yield=56.5%.

TLC ($CH_2Cl_2$ 98/$CH_3OH$ 2): Rf=0.55.

Intermediate of General Formula (5c)

1,2,3,4-Tetrahydro-4-benzyl-5-oxoimidazo[1,2-a]quinazolin-7-ylcarboxylic acid.

0.63 g (0.0021 mol) of 1,2,3,4-tetrahydro-4-benzyl-7-cyano-4H-imidazo[1,2-a]quinazolin-5-one is treated with 30 ml of a 50/50 mixture of concentrated sulphuric acid and water according to the method for synthesizing the intermediate of general formula (5c). After filtering off the precipitate obtained by dilution, washing and drying, 0.6 g of the expected compound, which is pure by TLC, is obtained.

The $^1$H NMR spectrum is compatible with the expected structure.

Yield=89.5%.

TLC ($CH_2Cl_2$ 90/$CH_3OH$ 10): Rf=0.20.

Synthesis of Example 5

N-(3,4-methylenedioxybenzyl)-4-benzyl-5-oxo-4H-imidazo[1,2-a]quinazol-7-ylcarboxamide 0.3 g (0.00094 mol) of 4-benzyl-5-oxo-4H-imidazo[1,2-a]quinazol-7-ylcarboxylic acid is dissolved in 15 ml of dry dimethylformamide in a reactor equipped with a condenser and a magnetic stirrer. 0.117 ml (0.00094 mol) of 3,4-methylenedioxybenzylamine and 0.308 g (0.00094 mol) of TOTU are then added, the mixture is stirred, the solution obtained is cooled to 0–5° C. and 0.327 ml (0.0019 mol) of DIPEA is then added.

A work-up identical to that of Example 3, followed by chromatography of the crude product on a column of silica, eluting with a $CH_2Cl_2$ 98/$CH_3OH$ 9 mixture gives 0.32 g of compound, which is pure by TLC (75% of the theoretical amount).

Recrystallization from ethanol gives colourless crystals with a melting point of:

m.p. (Tottoli)=189° C.

TLC ($CH_2Cl_2$ 98/$CH_3OH$ 2): Rf=0.5.

$^1$H NMR δ (ppm) [DMSO]: 4.45 (d, 2H); 5.45 (s, 2H); 6.0 (s, 2H); 6.8–6.9 (m, 2H); 6.95 (s, 1H); 7.2 (s, 1H); 7.25–7.35 (m, 3H); 7.4 (m, 2H); 8.15 (m, 2H); 8.35 (d, 1H); 8.8 (s, 1H); 9.3 (t, 1H).

Example 6

N-(4-Pyridylmethyl)-4-benzyl-5-oxo-4H-imidazo[1,2-a]quinazol-7-ylcarboxamide

The compound of Example 6 is prepared in the same way as that of Example 5, but using 4-pyridylmethylamine in the final step.

Yield=86%.

m.p. (Tottoli)=251° C.

TLC ($CH_2Cl_2$ 95/$CH_3OH$ 5): Rf=0.4.

$^1$H NMR δ (ppm) [DMSO]: 4.55 (d, 2H); 5.45 (s, 2H); 7.2 (s, 1H); 7.25–7.4 (m, 5H); 7.5 (m, 2H); 8.2 (m, 2H); 8.4 (d, 1H); 8.55 (d, 2H); 8.85 (s, 1H); 9.5 (t, 1H).

Example 7

N-(4-Methoxybenzyl)-4-benzyl-5-oxo-4,5-dihydro[1,2,4]triazolo[4,3-a]quinazoline-7-carboxamide The compound of Example 7 is prepared in the same way as in Example 3, but using 4-methoxybenzylamine.

m.p. (Tottoli)=255° C.

$^1$H NMR δ (ppm) [DMSO]: 3.75 (s, 3H); 4.45 (d, 2H); 5.4 (s, 2H); 6.9 (d, 2H); 7.2–7.35 (m, 5H); 7.45 (m, 2H); 8.3 (d, 1H); 8.4 (d, 1H); 8.8 (s, 1H); 9.35 (t, 1H); 9.55 (s, 1H).

Example 8

N-[3-(4-Pyridylsulphanyl)propyl]-4-benzyl-5-oxo-4,5-dihydro[1,2,4]triazolo[4,3-a]quinazoline-7-carboxamide The compound of Example 8 is prepared in the same way as in Example 3, but using 3-(4-pyridylsulphanyl)propylamine.

m.p. (Tottoli)=130° C.

$^1$H NMR δ (ppm) [DMSO]: 1.9–2.0 (m, 2H); 3.1–3.2 (m, 2H); 3.4–3.5 (m, 2H); 5.4 (s, 2H); 7.2–7.35 (m, 5H); 7.45 (d, 2H); 8.3 (d, 1H); 8.35–8.4 (m, 3H); 8.75 (d, 1H); 8.9–9.0 (t, 1H); 9.55 (s, 1H).

Example 9

N-(3,4-Methylenedioxybenzyl)-4-(4-cyanobenzyl)-5-oxo-4H-[1,2,4]triazolo[4,3-a]quinazol-7-ylcarboxamide 0.7 g (1.9 mmol) of N-(3,4-methylenedioxybenzyl)-4H-[1,2,4]triazolo[4,3-a]-5-oxo-quinazol-7-yl carboxamide in suspension in 20 ml of dimethylformamide and 0.62 g (1.9 mmol) of cesium carbonate are placed in a reactor fitted with a stirring system. The mixture is stirred 15 minutes at room temperature and 0.372 g (1.9 mmol) of 4-cyanobenzyl bromide is added. The reaction mixture is stirred at 90° C. for 12 hours and concentrated under vacuum. The residu obtained is taken up in a mixture of water and dichloromethane. The organic phase is separated, washed with brine and evaporated under vacuum. A chromatography of the residu over silica gel (dichloromethane/methanol : 95/5) yield 0.55 g (60%) of the desired compound pure on TLC. A recrystallisation from acetonitrile give 0.32 of uncolourless crystals.

m.p. (Tottoli)=215° C.

$^1$H NMR δ (ppm) [DMSO]: 4.4 (d, 2H); 5.45 (s, 2H); 6.0 (s, 2H); 6.8–6.9 (m, 2H); 6.95 (s, 1H); 7.6 (m, 2H); 7.8 (m, 2H); 8.3 (m, 2H); 8.4 (m, 1H); 8.8 (s, 1H); 9.3 (t, 1H); 9.6 (s, 11H).

The following compounds are obtained using a similar process described for the compound of Example 9:

Example 10

Methyl 4-{7-[(1,3-benzodioxol-5-ylmethyl)-carbamoyl]-5-oxo-5H-[1,2,4]triazolo[4,3-a]quinazol-4-ylmethyl}benzoate

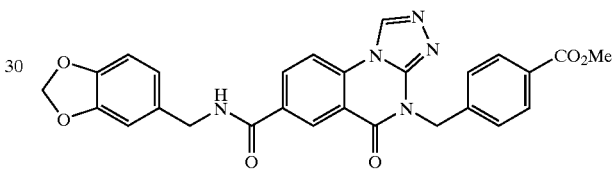

m.p. (Tottoli)=248° C.

$^1$H NMR δ (ppm) [DMSO]: 3.8 (s, 3H); 4.4 (d, 2H); 5.5 (s, 2H); 6.0 (s, 2H); 6.8–6.95 (m, 3H); 7.55 (d, 2H); 7.95 (d, 2H); 8.3 (d, 1H); 8.4 (d, 1H); 8.8 (s, 1H); 9.4 (t, 1H); 9.6 (s, 11H).

Example 11

Methyl 4-{7-[(4-methoxybenzyl)-carbamoyl]-5-oxo-5H-[1,2,4]triazolo[4,3-a]quinazol-4-ylmethyl}benzoate

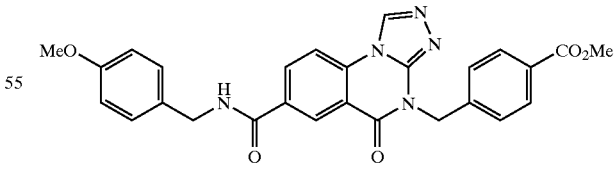

m.p. (Tottoli)=210° C.

$^1$H NMR δ (ppm) [DMSO]: 3.7 (s, 3H); 3.8 (s, 3H); 4.4 (d, 2H); 5.4 (s, 2H); 6.9 (d, 2H); 7.3 (d, 2H); 7.6 (d, 2H); 7.9 (d, 2H); 8.3 (d, 1H); 8.4 (d, 1H); 8.75 (s, 1H); 9.35 (t, 1H); 9.55 (s, 1H).

Example 12

Methyl 4-{7-[(pyridin-4-ylmethyl)-carbamoyl]-5-oxo-5H-[1,2,4]triazolo[4,3-a]quinazol-4-ylmethyl}benzoate

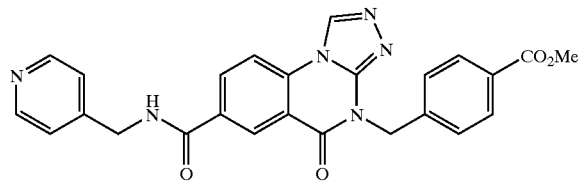

m.p. (Tottoli)=235° C.

$^1$H NMR δ (ppm) [DMSO]: 3.8 (s, 3H); 4.5 (d, 2H); 5.4 (s, 2H); 7.3 (d, 2H); 7.6 (d, 2H); 7.9 (d, 2H); 8.3 (d, 1H); 8.45 (d, 1H); 8.5 (d, 2H); 8.8 (s, 1H); 9.5 (t, 1H); 9.6 (s, 1H).

Example 13

(2-Dimethylamino-ethyl) 4-[7-(4-fluoro-benzylcarbamoyl)-5-oxo-5H-[1,2,4]triazolo[4,3-a]quinazol-4-ylmethyl]benzoate

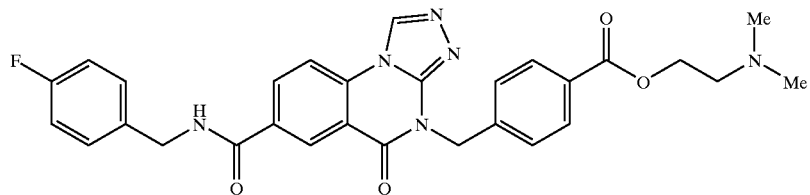

m.p. (Tottoli)=175° C.

$^1$H NMR δ (ppm) [DMSO]: 2.2 (s, 2H); 2.6 (t, 2H); 4.3 (t, 2H); 4.5 (d, 2H); 5.4 (s, 2H); 7.2 (t, 2H);7.4 (m, 2H); 7.6 (d, 2H); 7.9 (d, 2H); 8.3 (d, 1H); 8.4 (d, 1H); 8.7 (s, 1H); 9.4 (t, 1H); 9.6 (s, 1H).

Example 14

4-(4-Dimethylcarbamoyl-benzyl)-5-oxo-4,5-dihydro-[1,2,4]triazolo[4,3-a]quinazoline-7-carboxylic acid 4-methoxy-benzylamide

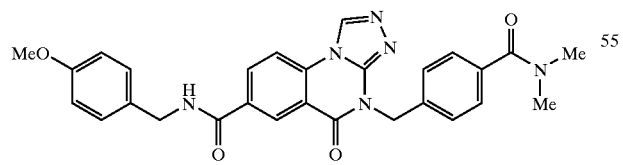

$^1$H NMR δ (ppm) [DMSO]: 2.9 (s, 3H); 2.95 (s, 3H); 3.7 (s, 3H); 4.4 (d, 2H); 5.4 (s, 2H); 6.8 (d, 2H); 7.25 (d, 2H); 7.35 (d, 2H); 7.5 (d, 2H); 8.3 (d, 1H); 8.4 (d, 1H); 8.8 (s, 1H); 9.3 (t, 1H); 9.55 (s, 1H).

Example 15

N-(pyridin-4-ylmethyl)-4-(4-cyanobenzyl)-5-oxo-4H-[1,2,4]triazolo[4,3-a]quinazol-7-ylcarboxamide

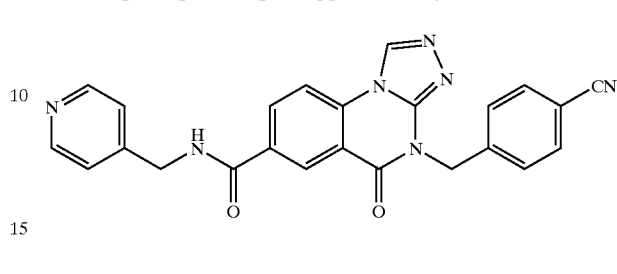

m.p. (Tottoli)=300° C.

$^1$H NMR δ (ppm) [DMSO]: 4.5 (d, 2H); 5.5 (s, 2H); 7.35 (m, 2H); 7.8 (m, 2H); 8.35 (m, 1H); 8.45 (m, 1H); 8.5 (m, 2H); 8.8 (s, 1H); 9.5 (t, 1H); 9.6 (s, 1H).

Example 16

Methyl (4-{7-[(4-methoxy)-benzylcarbamoyl]-5-oxo-5H-[1,2,4]triazolo[4,3-a]quinazolin-4-ylmethyl}-phenyl)-acetate

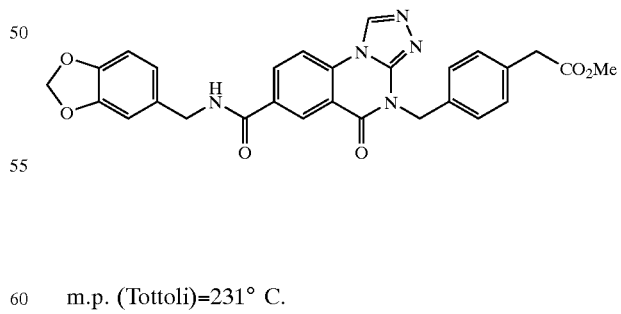

m.p. (Tottoli)=231° C.

$^1$H NMR δ (ppm) [DMSO]: 3.6 (s, 3H); 3.65 (s, 2H); 4.2 (d, 2H); 5.4 (s, 2H); 6.0 (s, 2H); 6.8–6.9 (m, 3H); 7.2 (d, 2H); 7.4 (d, 2H); 8.3 (d, 1H); 8.4 (d, 1H); 8.75 (s, 1H); 9.4 (t, 1H); 9.6 (s, 1H).

Example 17

Methyl (4-{7-[(4-methoxy)-benzylcarbamoyl]-5-oxo-5H-[1,2,4]triazolo[4,3-a]quinazolin-4-ylmethyl}-phenyl)-acetate

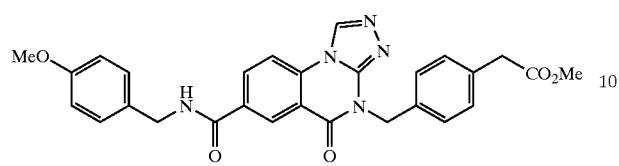

m.p. (Tottoli)=204° C.

$^1$H NMR δ (ppm) [DMSO]: 3.6 (s, 3H); 3.65 (s, 2H); 3.7 (s, 3H); 4.45 (d, 2H); 5.4 (s, 2H); 6.9 (d, 2H); 7.2 (d, 2H); 7.3 (d, 2H); 7.4 (d, 2H); 8.3 (d, 1H); 8.4 (d, 1H); 8.75 (s, 1H); 9.4 (t, 1H); 9.6 (s, 1H).

Example 18

Methyl (4-{7-[(pyridin-4-yl)-methylcarbamoyl]-5-oxo-5H-[1,2,4]triazolo[4,3-a]quinazolin-4-ylmethyl}-phenyl)-acetate

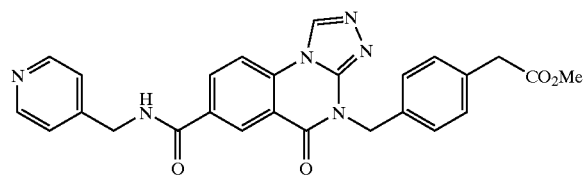

m.p. (Tottoli)=192° C.

$^1$H NMR δ (ppm) [DMSO]: 3.3 (s, 3H); 3.6 (s, 2H); 4.55 (d, 2H); 5.35 (s, 2H); 7.2 (m, 2H); 7.3–7.4 (m, 4H); 8.3 (m, 1H); 8.4 (m, 1H); 8.5 (s, 1H); 9.5 (t, 1H); 9.6 (s, 1H).

Example 19

N-(pyridin-4-ylmethyl) 4-[3-(pyridin-4-yl)-2-propen-1-yl]-5-oxo-4H-[1,2,4]triazolo[4,3-a]quinazol-7-ylcarboxamide

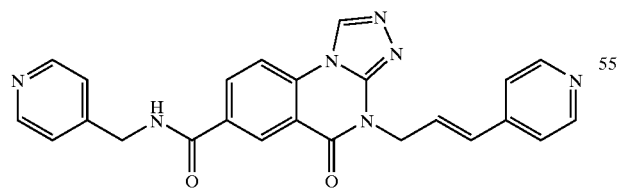

m.p. (Tottoli)=250° C.

$^1$H NMR δ (ppm) [DMSO]: 4.5 (d, 2H); 5 (d, 2H); 6.6–6.8 (m, 2H); 7.3 (m, 2H); 8.3 (m, 1H); 8.4–8.6 (m, 3H); 8.8 (s, 1H); 9.5–9.6 (m, 2H).

Example 20

4-[2-(4–Chloro-phenoxy)-ethyl]-5-oxo-4,5-dihydro-[1,2,4]triazolo[4,3-a]quinazoline-7-carboxylic acid 4-methoxy-benzylamide

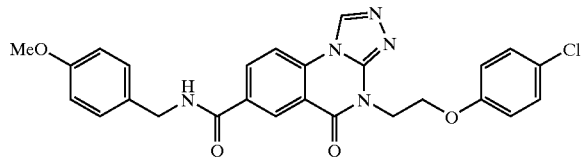

m.p. (Tottoli)=186° C.

$^1$H NMR δ (ppm) [DMSO]: 3.7 (s, 3H); 4.4 (t, 2H); 4.45 (d, 2H); 4.6 (t, 2H); 6.9 (m, 4H); 7.3 (m, 4H); 8.2 (d, 1H); 8.4 (dd, 1H); 8.7 (d, 1H); 9.4 (t, 1H); 9.5 (s, 1H).

Example 21

4-{7-[(4-Methoxybenzyl)-carbamoyl]-5-oxo-5H-[1,2,4]triazolo[4,3-a]quinazol-4-ylmethyl}benzoic acid

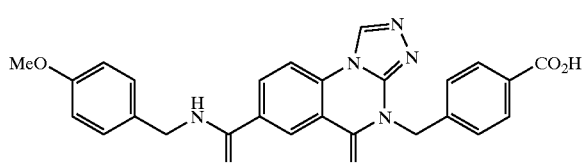

8.8 g (17.7 mmol) of compound obtained in the Example 11 in suspension in 900 ml of a mixture (water/methanol: 50/50) and 2.45 g (17.7 mmol) of potassium carbonate are placed in a reactor fitted with a stirring system. The mixture is heated under reflux for 45 minutes and 2.45 g (17.7 mmol) of potassium carbonate are added. After 30 minutes of stirring under reflux, the reaction mixture is partially concentrated under vacuum and a mixture of ice acetic acid and ice is added to provide a precipitate which is filtered, washed with water until neutral pH, and then with methanol. After dried under vacuum, 6.1 g (yield=61%) of the uncolourless desired product are obtained.

$^1$H NMR δ (ppm) [DMSO]: 3.8 (s, 3H); 4.45 (d, 2H); 5.45 (s, 2H); 6.9 (d, 2H); 7.3 (d, 2H); 7.55 (d, 2H); 8.3 (d, 2H); 8.4 (d, 1H); 8.75 (s, 1H); 9.4 (t, 1H); 9.55 (s, 1H); 12.9 (s, 1H).

The following compounds are obtained using a similar process described for the compound of Example 21:

Example 22

4-{7-[(1,3-Benzodioxol-5-ylmethyl)-carbamoyl]-5-oxo-5H-[1,2,4]triazolo[4,3]quinazol-4-ylmethyl}benzoic acid

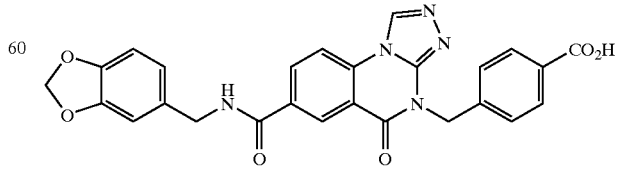

m.p. (Tottoli)=235° C.

¹H NMR δ (ppm) [DMSO]: 4.4 (d, 2H); 5.4 (s, 2H); 6.0 (s, 2H); 6.8 (m, 2H); 6.9 (d, 2H); 7.5 (d, 2H); 7.9 (d, 2H); 8.3 (d, 2H); 8.4 (d, 2H); 8.75 (s, 1H); 9.4 (t, 1H); 9.6 (s, 1H).

Example 23

4-{7-[(Pyridin-4-ylmethyl)-carbamoyl]-5-oxo-5H-[1,2,4]triazolo[4,3-a]quinazol-4-ylmethyl}benzoic acid

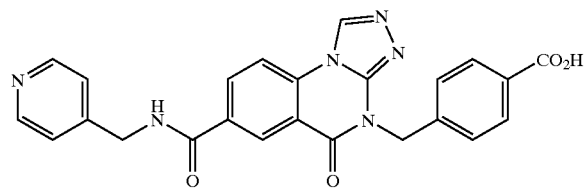

m.p. (Tottoli)=255° C.

¹H NMR δ (ppm) [DMSO]: 4.55 (d, 2H); 5.5 (s, 2H); 7.3 (d, 2H); 7.55 (d, 2H); 7.9 (d, 1H); 8.3 (d, 1H); 8.4 (d, 2H); 8.5 (d, 2H); 8.8 (s, 1H); 9.5 (t, 1H); 9.6 (s, 1H); 13.0 (m, 1H).

Example 24

4-{7-[(4-Fluoro)-benzylcarbamoyl]-5-oxo-5H-[1,2,4]triazolo[4,3-a]quinazol-4-ylmethyl}benzoic acid

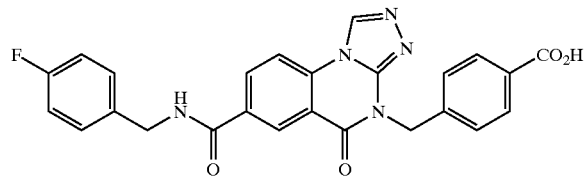

m.p. (Tottoli)=303° C.

¹H NMR δ (ppm) [DMSO]: 4.5 (d, 2H); 5.6 (s, 2H); 7.2 (m, 2H); 7.4 (m, 2H); 7.6 (d, 2H); 7.9 (d, 2H); 8.3 (d, 1H); 8.4 (d, 2H); 8.8 (s, 1H); 9.4 (t, 1H); 9.6 (s, 1H).

Example 25

(4-{7-[(4-Methoxy)-benzylcarbamoyl]-5-oxo-5H-[1,2,4]triazolo[4,3-a]quinazolin-4-ylmethyl}-phenyl)-acetic acid

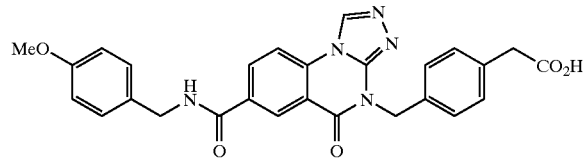

m.p. (Tottoli)=268° C.

¹H NMR δ (ppm) [DMSO]: 3.5 (s, 2H); 3.7 (s, 3H); 4.45 (d, 2H); 5.4 (s, 2H); 6.9 (d, 2H); 7.2 (d, 2H); 7.3 (d, 2H); 7.4 (d, 2H); 8.3 (d, 1H); 8.4 (d, 1H); 8.8 (s, 1H); 9.4 (t, 1H); 9.5 (t, 1H); 12.2 (m, 1H).

Example 26

(4-{7-[(1,3-Benzodioxol-5-ylmethyl)-carbamoyl]-5-oxo-5H-[1,2,4]triazolo[4,3-a]quinazolin-4-ylmethyl}-phenyl)-acetic acid

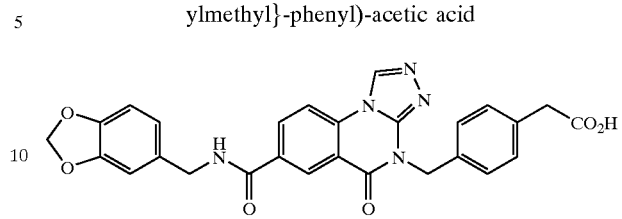

m.p. (Tottoli)=232° C.

¹H NMR δ (ppm) [DMSO]: 3.4 (s, 2H); 4.4 (d, 2H); 5.3 (s, 2H); 6.0 (s, 2H); 6.8–6.9 (m, 3H); 7.2 (d, 2H); 7.3 (d, 2H); 8.3 (d, 1H); 8.4 (d, 1H); 8.7 (s, 1H); 9.3 (t, 1H); 9.5 (s, 1H).

Example 27

(4-{7-[(Pyridin-4-yl)-methylcarbamoyl]-5-oxo-5H-[1,2,4]triazolo[4,3-a]quinazolin-4-ylmethyl}-phenyl)-acetic acid

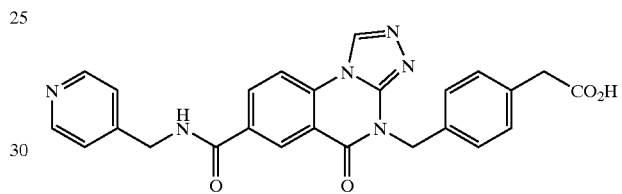

¹H NMR δ (ppm) [DMSO]: 3.5 (s, 3H); 4.5 (d, 2H); 5.4 (s, 2H); 7.2 (d, 2H); 7.3 (d, 5–2H); 7.4 (d, 2H); 8.3 (d, 1H); 8.4 (d, 1H); 8.5 (d, 2H); 8.8 (s, 1H); 9.5 (t, 1H); 9.6 (s, 1H).

Example 28

Evaluation of the In Vitro Activity of the MMP-13-Inhibitor Compounds According to the Invention The inhibitory activity of the compounds of formula (I) according to the invention with respect to matrix metalloprotease-13 was evaluated by testing the ability of the compounds of the invention to inhibit the proteolysis of a peptide substrate with MMP-13.

The peptide substrate used in the test is the following peptide: Ac-Pro-Leu-Gly-thioester-Leu-Leu-Gly-OEt.

The inhibitory activity of a compound of formula (I) according to the invention is expressed as the IC50 value, which is the concentration of inhibitor for which an inhibition of 50% of the activity of the matrix metalloprotease under consideration is observed.

To carry out this test, a reaction medium of 100 µl volume is prepared, containing: 50 mM of HEPES buffer, 10 mM of $CaCl_2$ and 1 mM of 5,5'-dithiobis(2-nitrobenzoic acid) (DTNB), and 100 µM of substrate, the pH being adjusted to 7.0.

Increasing concentrations of the inhibitory compound present in a 2.0% DMSO solution and 2.5 nM of the catalytic domain of human MMP-13 are added to the test samples.

The concentrations of inhibitors present in the test samples range from 100 µM to 0.5 nM.

The measurement of the proteolysis of the substrate peptide is monitored by measuring the absorbence at 405 nm using a spectrophotometric machine for reading microplates, at the laboratory temperature, the measurements being carried out continuously for 10 to 15 minutes.

The IC50 values are calculated from the curve in which the percentage of the catalytic activity relative to the control is represented on the X-axis and the concentration of inhibitor is represented on the Y-axis.

The IC50 values on MMP-13 of the compounds of Examples 1 to 6 are given in Table 1 below.

TABLE 1

| Example | IC50 ($\mu$M) |
|---|---|
| 1 | 0.0034 |
| 2 | 0.0023 |
| 3 | 0.0040 |
| 4 | 0.040 |
| 5 | 0.165 |

The test described above for the inhibition of MMP-13 was also adapted and used to determine the ability of the compounds of formula (I) to inhibit the matrix metalloproteases MMP-1, MMP-2, MMP-3, MMP-7, MMP-9, MMP-12 and MMP-14.

The results obtained show that the cyclized quinazoline compounds according to the invention generally have IC50 values for MMP-13 which are about 100 times lower than the IC50 values for the same compounds with respect to the other matrix metalloproteases tested.

Bibliographic References

MONTANA J. and BAXTER A., Current opinion in drug discovery and development, 3 (4), 353–361, (2000).

CLARK I M et al., Current opinion in anti-inflammatory and immunomodulatory investigational drugs, 2 (1), 16–25, (2000).

What is claimed is:
1. A compound selected from those of formula (I):

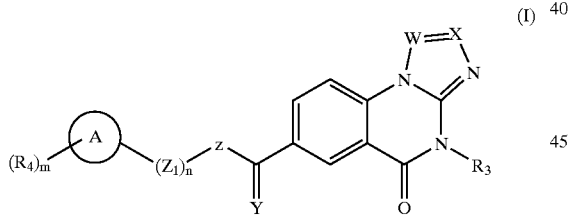

in which:
W represents N or C—$R_1$; in which $R_1$ is selected from:
hydrogen atom,
$OR_5$, $SR_5$ in which $R_5$ is selected from hydrogen, ($C_1$–$C_6$)alkyl and aryl($C_1$–$C_6$)alkyl,
($C_1$–$C_6$)alkyl, cycloalkyl of 3 to 8 carbon atoms optionally interrupted with one hetero atom selected from oxygen, sulfur and nitrogen, aryl, heteroaryl and aryl($C_1$–$C_6$)alkyl, these groups being optionally substituted by ($CH_2$)p-OH or ($CH_2$)p-$NH_2$, in which p is an integer from 0 to 4 inclusive,
X represents N or C—$R_2$ in which $R_2$ is selected from:
hydrogen atom,
$NR_6R_7$, $OR_6$, $SR_6$ in which $R_6$ and $R_7$, identical or different, are selected from hydrogen, ($C_1$–$C_6$)alkyl and aryl($C_1$–$C_6$)alkyl,
($C_1$–$C_6$)alkyl, cycloalkyl of 3 to 8 carbon atoms optionally interrupted with one hetero atom selected from oxygen, sulfur and nitrogen, aryl, heteroaryl and aryl($C_1$–$C_6$)alkyl, these groups being optionally substituted by ($CH_2$)p-OH or ($CH_2$)p-$NH_2$, in which p is an integer from 0 to 4 inclusive, Y represents a group selected from oxygen, sulfur, —NH, and —N($C_1$–$C_6$)alkyl,
Z represents a group selected from:
oxygen, sulphur,
and —$NR_8$ in which $R_8$ represents a group selected from hydrogen, ($C_1$–$C_6$)alkyl, aryl($C_1$–$C_6$)alkyl, cycloalkyl, aryl, and heteroaryl, and
when Y is oxygen, sulphur, or —N($C_1$–$C_6$)alkyl, Z optionally represents a carbon atom which is optionally substituted by a group selected from ($C_1$–$C_6$) alkyl, aryl, aryl($C_1$–$C_6$)alkyl, aromatic heterocycle, non-aromatic heterocycle, and cycloalkyl,
n is an integer from 0 to 8 inclusive,
$Z_1$ represents a group —$CR_9R_{10}$ wherein $R_9$ and $R_{10}$, identical or different, represent a group selected from hydrogen, ($C_1$–$C_6$)alkyl, halo($C_1$–$C_6$)alkyl, halogen, $NR_5R_{11}$, $OR_5$, $SR_5$ and C(=O)$OR_5$ in which $R_5$ and $R_{11}$, identical or different, represents hydrogen atom or ($C_1$–$C_6$)alkyl, and
when n is greater than or equal to 2, the hydrocarbon chain $Z_1$ optionally contains one or more multiple bonds,
and/or one of the carbon atoms in the hydrocarbon chain $Z_1$ may be replaced with an oxygen atom, a sulphur atom which is optionally substituted by one or two oxygen atoms, or a nitrogen atom which is optionally substituted by ($C_1$–$C_6$)alkyl,
A represents a group selected from:
aromatic or non-aromatic, 5- or 6-membered monocycle comprising from 0 to 4 heteroatoms selected from nitrogen, oxygen and sulphur, and
bicycle, composed of two aromatic or non-aromatic, 5- or 6-membered rings, which may be identical or different, comprising from 0 to 4 heteroatoms selected from nitrogen, oxygen and sulphur,
m is an integer from 0 to 7 inclusive,
the group(s) $R_4$, which may be identical or different, is (are) selected from ($C_1$–$C_6$)alkyl, halogen, —CN, —$NO_2$, —$SCF_3$, —$CF_3$, —$OCF_3$, —$NR_5R_{11}$, —$OR_5$, —$SR_5$, —$SOR_5$, —$SO_2R_5$, —($CH_2$)$_k$$SO_2NR_5R_{11}$, —$X_1$($CH_2$)$_k$C(=O)$OR_5$, —($CH_2$)$_k$C(=O)$OR_5$, —$X_1$($CH_2$)$_k$C(=O)$NR_5R_{11}$, —($CH_2$)$_k$C(=O)$NR_5R_{11}$, and —$X_2$—$R_{12}$ in which:
$X_1$ represents a group selected from oxygen, sulphur optionally substituted by one or two oxygen atoms, and nitrogen substituted by hydrogen or ($C_1$–$C_6$) alkyl,
k is an integer from 0 to 3 inclusive,
$R_5$ and $R_{11}$, which may be identical or different, are selected from hydrogen and ($C_1$–$C_6$)alkyl,
$X_2$ represents a group selected from single bond, —$CH_2$—, oxygen atom, sulphur atom optionally substituted by one or two oxygen atoms, and nitrogen atom substituted by hydrogen atom or ($C_1$–$C_6$) alkyl group,
$R_{12}$ represents an aromatic or non-aromatic, heterocyclic or non-heterocyclic, 5- or 6-membered ring which is optionally substituted by one or more groups, which may be identical or different, selected from ($C_1$–$C_6$)alkyl, halogen, hydroxyl and amino, and when the ring is heterocyclic, it comprises from 1 to 4 heteroatoms selected from nitrogen, oxygen and sulphur, $R_3$ represents a group selected from:
hydrogen,
($C_1$–$C_6$)alkyl, ($C_2$–$C_6$)alkenyl, ($C_2$–$C_6$)alkynyl, these groups being optionally substituted by one or more groups, which may be identical or different, selected from amino, cyano, halo($C_1$–$C_6$)alkyl, cycloalkyl, —C(=O)NR$_5$R$_{11}$, —C(=O)OR$_5$, —OR$_5$, and —SR$_5$, in which R$_5$ and R$_{11}$, which may be identical or different, are as defined hereinbefore,
and the group of formula:

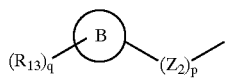

in which p is an integer from 0 to 8 inclusive,
$Z_2$ represents —CR$_{14}$R$_{15}$ wherein R$_{14}$ and R$_{15}$, identical or different, represent a group selected from hydrogen, ($C_1$–$C_6$)alkyl, phenyl, halo($C_1$–$C_6$)alkyl, halogen, amino, —OR$_5$, —NR$_5$R$_{11}$, —SR$_5$ and —C(=O)OR$_5$ in which R$_5$ and R$_{11}$, identical or different, are as defined hereinbefore, and
when p is greater than or equal to 2, the hydrocarbon chain $Z_2$ optionally contains one or more multiple bonds,
and/or one of the carbon atoms in the hydrocarbon chain $Z_2$ may be replaced with an oxygen atom, a sulphur atom which is optionally substituted by one or two oxygen atoms, or a nitrogen atom which is optionally substituted by ($C_1$–$C_6$)alkyl,
B represents a group selected from:
aromatic or non-aromatic 5- or 6-membered monocycle comprising from 0 to 4 heteroatoms selected from nitrogen, oxygen and sulphur, and
bicycle, composed of two aromatic or non-aromatic, 5- or 6-membered rings, which may be identical or different, comprising from 0 to 4 heteroatoms selected from nitrogen, oxygen and sulphur,
q is an integer from 0 to 7 inclusive,
the group(s) R$_{13}$, which may be identical or different, is (are) selected from ($C_1$–$C_6$)alkyl, halogen, —CN, —NO$_2$, —CF$_3$, —OCF$_3$, ($C_1$–$C_6$)acyl, —(CH$_2$)$_k$NR$_{16}$R$_{17}$, —X$_3$—(CH$_2$)$_k$NR$_{16}$R$_{17}$, —N(R$_{16}$)C(=O)R$_{17}$, —N(R$_{16}$)C(=O)OR$_{17}$, —N(R$_{16}$)SO$_2$R$_{17}$, —N(SO$_2$R$_{16}$)$_2$, —OR$_{16}$, —S(O)$_{k1}$R$_{16}$, —(CH$_2$)$_k$SO$_2$NR$_{16}$R$_{17}$, —X$_3$(CH$_2$)$_k$C(=O)OR$_{16}$, —(CH$_2$)$_k$C(=O)OR$_{16}$, —X$_3$(CH$_2$)$_k$C(=O)NR$_{16}$R$_{17}$, —(CH$_2$)$_k$C(=O)NR$_{16}$R$_{17}$, —C(=O)O—R$_{19}$—NR$_{16}$NR$_{17}$ and —X$_4$—R$_{18}$, in which:
X$_3$ represents a group selected from oxygen, sulphur optionally substituted by one or two oxygen atoms, and nitrogen substituted by a hydrogen atom or a ($C_1$–$C_6$)alkyl group,
k is an integer from 0 to 3 inclusive,
k$_1$ is an integer from 0 to 2 inclusive,
R$_{16}$ and R$_{17}$, which may be identical or different, are selected from hydrogen and ($C_1$–$C_6$)alkyl,
X$_4$ represents a group selected from single bond, —CH$_2$—, oxygen atom, sulphur atom optionally substituted by one or two oxygen atoms, and nitrogen atom substituted by hydrogen atom or ($C_1$–$C_6$)alkyl group, R$_{18}$ represents an aromatic or non-aromatic, heterocyclic or non-heterocyclic, 5- or 6-membered ring, which is optionally substituted by one or more groups, which may be identical or different, selected from ($C_1$–$C_6$)alkyl, halogen, hydroxyl, ($C_1$–$C_6$)alkoxy, oxo, cyano, tetrazole, —NR$_5$R$_{11}$, and —C(=O)OR$_5$ wherein R$_5$ and R$_{11}$ are as defined hereinbefore, and, when the ring is heterocyclic, it comprises from 1 to 4 heteroatoms selected from nitrogen, oxygen and sulphur,
R$_{19}$ represents a ($C_1$–$C_6$)alkylene group,
optionally, a racemic form, isomers thereof, N-oxydes thereof, or a pharmaceutically acceptable salts thereof,
it being understood that:
aryl represents a monocycle or bicycle containing from 5 to 10 and preferably 5 to 6 carbon atoms,
heteroaryl represents aryl, as defined hereinbefore, in which one to four carbon atoms are replaced by one to four heteroatoms selected from nitrogen, oxygen and sulphur,
cycloalkyl represents monocycle or bicycle containing from 3 to 10 and preferably from 3 to 6 carbon atoms,
heterocycle represents heteroaryl as defined above, heteroaryl partially hydrogenated and cycloalkyl as defined above in which one to four carbon atoms are replaced by one to four heteroatoms selected from oxygen, sulphur and nitrogen,
aryl($C_1$–$C_6$)alkyl represents a group in which alkyl contains from 1 to 6 carbon atoms and aryl contains from 5 to 10 carbon atoms,
cycloalkyl($C_1$–$C_6$)alkyl represents a group in which alkyl contains from 1 to 6 carbon atoms and cycloalkyl contains from 3 to 10 carbon atoms.

2. A compound according to claim 1 characterized in that:
W is C—R$_1$ and X is N or C—R$_2$ in which R$_1$ and R$_2$, identical or different, are selected from hydrogen and methyl,
Y is O,
Z represents an oxygen atom or —NH group,
n is an integer from 0 to 4 inclusive,
$Z_1$ represents a group —CR$_9$R$_{10}$ wherein R$_9$ and R$_{10}$, identical or different, represent a group selected from hydrogen, ($C_1$–$C_6$)alkyl, halo($C_1$–$C_6$)alkyl, halogen, —NR$_5$R$_{11}$—OR$_5$, —SR$_5$ and —C(=O)OR$_5$ in which R$_5$ and R$_{11}$, identical or different, represent hydrogen atom or ($C_1$–$C_6$)alkyl, and
when n is greater than or equal to 2, the hydrocarbon chain $Z_1$ optionally contains one double bonds,
and/or one of the carbon atoms in the hydrocarbon chain $Z_1$ may be replaced with an oxygen atom, a sulphur atom which is optionally substituted by one or two oxygen atoms, or a nitrogen atom which is optionally substituted by ($C_1$–$C_6$)alkyl,
R$_3$, R$_4$ and A are as defined in the compound of formula (I),
optionally, a racemic form, isomers thereof, N-oxydes thereof, or a pharmaceutically acceptable salts thereof.

3. A compound according to claim 1 characterized in that:
R$_3$ represents the group of formula:

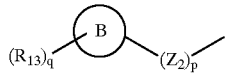

in which p is an integer from 0 to 4 inclusive,
Z$_2$ represents —CR$_{14}$R$_{15}$ wherein R$_{14}$ and R$_{15}$, identical or different, represent a group selected from hydrogen and methyl, and when p is greater than or equal to 2, the hydrocarbon chain Z$_2$ optionally contains one double bond,
B represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl,
q is an integer from 0 to 7 inclusive,
the group(s) R$_{13}$, which may be identical or different, is (are) selected from (C$_1$–C$_6$)alkyl, halogen, —CN, —CF$_3$, —NR$_{16}$R$_{17}$, —OR$_{16}$, —SO$_2$R$_{16}$, —(CH$_2$)$_k$SO$_2$NR$_{16}$R$_{17}$, —O(CH$_2$)$_k$C(=O)OR$_{16}$, —(CH$_2$)$_k$C(=O)OR$_{16}$, —O(CH$_2$)$_k$C(=O)NR$_{16}$R$_{17}$, —C(=O)O—R$_{19}$—NR$_{16}$NR$_{17}$ and —(CH$_2$)$_k$C(=O)NR$_{16}$R$_{17}$, in which k is an integer from 0 to 3 inclusive, R$_{16}$ and R$_{17}$, which may be identical or different, are selected from hydrogen and (C$_1$–C$_6$)alkyl, and R$_{19}$ represents a (C$_1$–C$_6$)alkylene group,
W, X, Y, Z, Z$_1$, n, m, A and R$_4$ are as defined in the compound of formula (I),
optionally, a racemic form, isomers thereof, N-oxydes thereof, or a pharmaceutically acceptable salts thereof.

4. A compound according to claim 1 characterized in that:
n is an integer from 0 to 4 inclusive,
Z$_1$ represents a group —CR$_9$R$_{10}$ wherein R$_9$ and R$_{10}$ represent each hydrogen atom, and
when n is greater than or equal to 2, the hydrocarbon chain Z$_1$ optionally contains one double bond,
and/or one of the carbon atoms in the hydrocarbon chain Z$_1$ may be replaced with an oxygen atom, a sulphur atom which is optionally substituted by one or two oxygen atoms, or a nitrogen atom which is optionally substituted by (C$_1$–C$_6$)alkyl,
A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl,
m is an integer from 0 to 7 inclusive,
the group(s) R$_4$, which may be identical or different, is (are) selected from (C$_1$–C$_6$)alkyl, halogen, —CN, —CF$_3$, —NR$_5$R$_{11}$, —OR$_5$, and —C(=O)OR$_5$ in which R$_5$ and R$_{11}$, which may be identical or different, are selected from hydrogen and (C$_1$–C$_6$)alkyl,
W, X, Y, Z and R$_3$ are as defined in the compound of formula (I),
optionally, a racemic form, isomers thereof, N-oxydes thereof, or a pharmaceutically acceptable salts thereof.

5. A compound according to claim 1 characterized in that:
W is C—R, and X is N or C—R$_2$ in which R$_1$ and R$_2$, identical or different, are selected from hydrogen and methyl,
Y is O,
Z represents an oxygen atom or —NH group,
n is an integer from 0 to 4 inclusive,
Z$_1$ represents a group —CR$_9$R$_{10}$ wherein R$_9$ and R$_{10}$, identical or different, represent a group selected from hydrogen and methyl, and when n is greater than or equal to 2, the hydrocarbon chain Z$_1$ optionally contains one or more multiple bonds,
and/or one of the carbon atoms in the hydrocarbon chain Z$_1$ may be replaced with an oxygen atom, a sulphur atom which is optionally substituted by one or two oxygen atoms, or a nitrogen atom which is optionally substituted by (C$_1$–C$_6$)alkyl,
A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl,
m is an integer from 0 to 7 inclusive,
the group(s) R$_4$, which may be identical or different, is (are) selected from (C$_1$–C$_6$)alkyl, halogen, —CN, —CF$_3$, —NR$_5$R$_{11}$, —OR$_5$, —SO$_2$R$_5$, —(CH$_2$)$_k$SO$_2$NR$_5$R$_{11}$, —X$_1$(CH$_2$)$_k$C(=O)OR$_5$, —(CH$_2$)$_k$C(=O)OR$_5$, —X$_1$(CH$_2$)$_k$C(=O)NR$_5$R$_{11}$, —(CH$_2$)$_k$C(=O)NR$_5$R$_{11}$, and —X$_2$—R$_{12}$ in which:
X$_1$ represents a group selected from oxygen, sulphur and —NH,
k is an integer from 0 to 3 inclusive,
R$_5$ and R$_{11}$, which may be identical or different, are selected from hydrogen and (C$_1$–C$_6$)alkyl,
X$_2$ represents a group selected from single bond, —CH$_2$—, oxygen atom, and sulphur atom optionally substituted by one or two oxygen atoms,
R$_{12}$ represents an aromatic or non-aromatic, heterocyclic or non-heterocyclic, 5- or 6-membered ring which is optionally substituted by one or more groups, which may be identical or different, selected from (C$_1$–C$_6$)alkyl, halogen, hydroxyl and amino, and when the ring is heterocyclic, it comprises from 1 to 4 heteroatoms selected from nitrogen, oxygen and sulphur;
R$_3$ represents the group of formula:

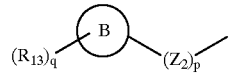

in which p is an integer from 0 to 6 inclusive,
Z$_2$ represents —CR$_{14}$R$_{15}$ wherein R$_{14}$ and R$_{15}$, identical or different, represent a group selected from hydrogen, (C$_1$–C$_6$)alkyl, phenyl, halo(C$_1$–C$_6$)alkyl, halogen, amino, OR$_5$, SR$_5$ and —C(=O)OR$_5$ in which R$_5$ is as defined in the compound of formula (I), and
when p is greater than or equal to 2, the hydrocarbon chain Z$_2$ optionally contains one or more multiple bonds,
and/or one of the carbon atoms in the hydrocarbon chain Z$_2$ may be replaced with an oxygen atom, a sulphur atom which is optionally substituted by one or two oxygen atoms, or a nitrogen atom which is optionally substituted by (C$_1$–C$_6$)alkyl,
B represents a group selected from:
aromatic or non-aromatic 5- or 6-membered monocycle comprising from 0 to 4 heteroatoms selected from nitrogen, oxygen and sulphur, and
bicycle, composed of two aromatic or non-aromatic, 5- or 6-membered rings, which may be identical or different, comprising from 0 to 4 heteroatoms selected from nitrogen, oxygen and sulphur,
q is an integer from 0 to 7 inclusive,
the group(s) R$_{13}$, which may be identical or different, is (are) selected from (C$_1$–C$_6$)alkyl, halogen, —CN, —$CF_3$, —$NR_{16}R_{17}$, —$OR_{16}$, —$SO_2R_{16}$, —$(CH_2)_kSO_2NR_{16}R_{17}$, —$X_3(CH_2)_kC(=O)OR_{16}$, —$(CH_2)_kC(=O)OR_{16}$, —$X_3(CH_2)_kC(=O)NR_{16}R_{17}$, —$(CH_2)_kC(=O)NR_{16}R_{17}$, —$C(=O)O$—$R_{19}$—$NR_{16}NR_{17}$ and —$X_4$—$R_{18}$, in which:

$X_3$ represents a group selected from oxygen atom, sulphur atom and —NH group, k is an integer from 0 to 3 inclusive, $R_{16}$ and $R_{17}$, which may be identical or different, are selected from hydrogen and ($C_1$–$C_6$)alkyl, $X_4$ represents a group selected from single bond, —$CH_2$—, oxygen atom, and sulphur atom optionally substituted by one or two oxygen atoms, $R_{18}$ represents an aromatic or non-aromatic, heterocyclic or non-heterocyclic, 5- or 6-membered ring, which is optionally substituted by one or more groups, which may be identical or different, selected from ($C_1$–$C_6$)alkyl, halogen, hydroxyl, and amino, and when the ring is heterocyclic, it comprises from 1 to 4 heteroatoms selected from nitrogen, oxygen and sulphur, $R_{19}$ represents a ($C_1$–$C_6$)alkylene group, optionally, a racemic form, isomers thereof, N-oxydes thereof, or a pharmaceutically acceptable salts thereof.

6. A compound according to claim 1 characterized in that:

W is C—$R_1$ and X is N or C—$R_2$ in which $R_1$ and $R_2$, identical or different, are selected from hydrogen and methyl, Y is O, Z represents an oxygen atom or a —NH group, n is an integer from 0 to 4 inclusive, $Z_1$ represents a group —$CR_9R_{10}$ wherein $R_9$ and $R_{10}$, identical or different, represent a group selected from hydrogen and methyl, and when n is greater than or equal to 2, the hydrocarbon chain $Z_1$ optionally contains one double bond, and/or one of the carbon atoms in the hydrocarbon chain $Z_1$ may be replaced with an oxygen atom, a sulphur atom which is optionally substituted by one or two oxygen atoms, or a nitrogen atom which is optionally substituted by ($C_1$–$C_6$)alkyl, A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, m is an integer from 0 to 7 inclusive, the group(s) $R_4$, which may be identical or different, is (are) selected from ($C_1$–$C_6$)alkyl, halogen, —CN, —$CF_3$, —$NR_5R_{11}$, —$OR_5$, and —$C(=O)OR_5$, in which $R_5$ and $R_{11}$, which may be identical or different, are selected from hydrogen and ($C_1$–$C_6$)alkyl, $R_3$ represents the group of formula:

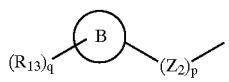

in which p is an integer from 0 to 4 inclusive, $Z_2$ represents —$CR_{14}R_{15}$ wherein $R_{14}$ and $R_{15}$, identical or different, represent a group selected from hydrogen and methyl, and when p is greater than or equal to 2, the hydrocarbon chain $Z_2$ optionally contains one double bond, and/or one of the carbon atoms in the hydrocarbon chain $Z_2$ may be replaced with an oxygen atom, a sulphur atom which is optionally substituted by one or two oxygen atoms, or a nitrogen atom which is optionally substituted by ($C_1$–$C_6$)alkyl, B represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, q is an integer from 0 to 7 inclusive, the group(s) $R_{13}$, which may be identical or different, is (are) selected from ($C_1$–$C_6$)alkyl, halogen, —CN, —$CF_3$, —$NR_{16}R_{17}$, —$OR_{16}$, —$SO_2R_{16}$, —$(CH_2)_kSO_2NR_{16}R_{17}$, —$X_3(CH_2)_kC(=O)OR_{16}$, —$(CH_2)_kC(=O)OR_{16}$, —$X_3(CH_2)_kC(=O)NR_{16}R_{17}$, —$(CH_2)_kC(=O)NR_{16}R_{17}$, —$C(=O)O$—$R_{19}$—$NR_{16}NR_{17}$, and —$X_4$—$R_{18}$, in which:

$X_3$ represents a group selected from oxygen atom, sulphur atom and —NH group, k is an integer from 0 to 3 inclusive, $R_{16}$ and $R_{17}$, which may be identical or different, are selected from hydrogen and ($C_1$–$C_6$)alkyl, $X_4$ represents a group selected from single bond, —$CH_2$—, oxygen atom, and sulphur atom optionally substituted by one or two oxygen atoms, $R_{18}$ represents an aromatic or non-aromatic, heterocyclic or non-heterocyclic, 5- or 6-membered ring, which is optionally substituted by one or more groups, which may be identical or different, selected from ($C_1$–$C_6$)alkyl, halogen, hydroxyl, and amino, and when the ring is heterocyclic, it comprises from 1 to 4 heteroatoms selected from nitrogen, oxygen and sulphur, $R_{19}$ represents a ($C_1$–$C_6$)alkylene group, optionally, a racemic form, isomers thereof, N-oxydes thereof, or a pharmaceutically acceptable salts thereof.

7. A compound according to claim 1 characterized in that:

W is C—$R_1$ and X is N or C—$R_2$ in which $R_1$ and $R_2$, identical or different, are selected from hydrogen and methyl, Y is O, Z represents an oxygen atom or a —NH group, n is an integer from 0 to 4 inclusive, $Z_1$ represents a methylen group, and when n is greater than or equal to 2, the hydrocarbon chain $Z_1$ optionally contains one double bond, and/or one of the carbon atoms in the hydrocarbon chain $Z_1$ may be replaced with an oxygen atom, a sulphur atom which is optionally substituted by one or two oxygen atoms, or a nitrogen atom which is optionally substituted by ($C_1$–$C_6$)alkyl, A represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, m is an integer from 0 to 7 inclusive, the group(s) $R_4$, which may be identical or different, is (are) selected from ($C_1$–$C_6$)alkyl, halogen, —CN, —$CF_3$, —$NR_5R_{11}$, —$OR_5$, and —$C(=O)OR_5$, in which $R_5$ and $R_{11}$, which may be identical or different, are selected from hydrogen and ($C_1$–$C_6$)alkyl, $R_3$ represents the group of formula:

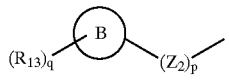

in which p is an integer from 0 to 4 inclusive, $Z_2$ represents —$CR_{14}R_{15}$ wherein $R_{14}$ and $R_{15}$, identical or different, represent a group selected from hydrogen and methyl, and when p is greater than or equal to 2, the hydrocarbon chain $Z_2$ optionally contains one double bond, B represents a group selected from phenyl, pyridyl, thienyl, imidazolyl, furyl, 1,3-benzodioxolyl, benzodioxinyl, benzothienyl, benzofuryl, 2,1,3-benzothiadiazolyl, benzofurazanyl, and indolyl, q is an integer from 0 to 7 inclusive, the group(s) $R_{13}$, which may be identical or different, is (are) selected from ($C_1$–$C_6$)alkyl, halogen, —CN, —$CF_3$, —$NR_{16}R_{17}$, —$OR_{16}$, —$SO_2R_{16}$, —$(CH_2)_kSO_2NR_{16}R_{17}$, —$O(CH_2)_kC(=O)OR_{16}$, —$(CH_2)_kC(=O)OR_{16}$, —$O(CH_2)_kC(=O)NR_{16}R_{17}$, —$(CH_2)_kC(=O)NR_{16}R_{17}$, and —$C(=O)O$—$R_{19}$—$NR_{16}NR_{17}$ in which:

k is an integer from 0 to 3 inclusive, $R_{16}$ and $R_{17}$, which may be identical or different, are selected from hydrogen and ($C_1$–$C_6$)alkyl, $R_{19}$ represents a ($C_1$–$C_6$)alkylene group optionally, a racemic form, isomers thereof, N-oxydes thereof, or a pharmaceutically acceptable salts thereof.

8. A compound according to claim 1 wherein n is equal to one, optionally, a racemic form, isomers thereof, N-oxydes thereof, or a pharmaceutically acceptable salts thereof.

9. A compound according to claim 1 wherein $Z_1$ represents a group —$CR_9R_{10}$ in which $R_9$ and $R_{10}$ represent each a hydrogen atom, optionally, a racemic form, isomers thereof, thereof, or a pharmaceutically acceptable salts thereof.

10. A compound according to claim 1 wherein A represents a 5- to 6- membered aromatic monocycle or a 3,4-methylenedioxyphenyl group optionally substituted by one or more groups $R_4$ as defined in the compound of formula (I), optionally, a racemic form, isomers thereof, N-oxydes thereof, or a pharmaceutically acceptable salts thereof.

11. A compound according to claim 10 wherein A represents a phenyl group optionally substituted by one group $R_4$ as defined in the compound of the formula (I), optionally, a racemic form, isomers thereof, N-oxydes thereof, or a pharmaceutically acceptable salts thereof.

12. A compound according to claim 11 wherein A represents a phenyl group, m is equal to one, and $R_4$ represents a methoxy group or a fluoro group, optionally, a racemic form, isomers thereof, N-oxydes thereof, or a pharmaceutically acceptable salts thereof.

13. A compound according to claim 10 wherein A represents a 4-pyridinyl group and m is equal to zero, optionally, a racemic form, isomers thereof, N-oxydes thereof, or a pharmaceutically acceptable salts thereof.

14. A compound according to claim 1 wherein Z represents a —NH group and Y represents an oxygen atom, optionally, a racemic form, isomers thereof, N-oxydes thereof, or a pharmaceutically acceptable salts thereof.

15. A compound according to claim 1 wherein W represents a —CH group and X represents a nitrogen atom, optionally, a racemic form, isomers thereof, N-oxydes thereof, or a pharmaceutically acceptable salts thereof.

16. A compound according to claim 1 wherein $R_3$ represent a group of formula:

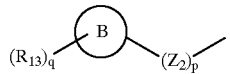

in which p is equal to one, $Z_2$ represents a methylene group, B represents a phenyl group, q is comprise between 0 to 1 inclusive, $R_{13}$ represents a group selected from —CN, —$(CH_2)_k$—$C(=O)OR_{16}$, —$(CH_2)_k$—$C(=O)NR_{16}R_{17}$, and —$C(=O)O$—$R_{19}$—$NR_{16}NR_{17}$ in which k, $R_{16}$, $R_{17}$, and $R_{19}$ are as defined in the compound of formula (I), optionally, a racemic form, isomers thereof, N-oxydes thereof, or a pharmaceutically acceptable salts thereof.

17. A compound according to claim 1 selected from:

benzyl 4-benzyl-5-oxo-4H-[1,2,4]triazolo[4,3-a]quinazol-7-ylcarboxylate, 4-pyridylmethyl 4-benzyl-5-oxo-4H-[1,2,4]triazolo[4,3-a]quinazol-7-ylcarboxylate, N-(3,4-methylenedioxybenzyl)-4-benzyl-5-oxo-4H-[1,2,4]triazolo[4,3-a]quinazol-7-ylcarboxamide, N-(4-pyridylmethyl)-4-benzyl-5-oxo-4H-[1,2,4]triazolo[4,3-a]quinazol-7-ylcarboxamide, N-(3,4-methylenedioxybenzyl)-4-benzyl-5-oxo-4H-imidazo[1,2-a]quinazol-7-ylcarboxamide, N-(4-pyridylmethyl)-4-benzyl-5-oxo-4H-imidazo[1,2-a]quinazol-7-ylcarboxamide, N-(4-methoxybenzyl)-4-benzyl-5-oxo-4,5-dihydro[1,2,4]triazolo[4,3-a]quinazoline-7-carboxamide, N-[3-(4-pyridylsulphanyl)propyl]-4-benzyl-5-oxo-4,5-dihydro[1,2,4]triazolo-[4,3-a]quinazoline-7-carboxamide, N-(3,4-Methylenedioxybenzyl)-4-(4-cyanobenzyl)-5-oxo-4H-[1,2,4]triazolo[4,3-a]quinazol-7-ylcarboxamide Methyl 4-{7-[(1,3-benzodioxol-5-ylmethyl)-carbamoyl]-5-oxo-5H-[1,2,4]triazolo[4,3-a]quinazol-4-ylmethyl}benzoate Methyl 4-{7-[(4-methoxybenzyl)-carbamoyl]-5-oxo-5H-[1,2,4]triazolo[4,3-a]quinazol-4-ylmethyl}benzoate Methyl 4-{7-[(pyridin-4-ylmethyl)-carbamoyl]-5-oxo-5H-[1,2,4]triazolo[4,3-a]quinazol-4-ylmethyl}benzoate (2-Dimethylamino-ethyl) 4-[7-(4-fluoro-benzylcarbamoyl)-5-oxo-5H-[1,2,4]triazolo[4,3-a]quinazol-4-ylmethyl]benzoate 4-(4-Dimethylcarbamoyl-benzyl)-5-oxo-4,5-dihydro-[1,2,4]triazolo[4,3-a]quinazoline-7-carboxylic acid 4-methoxy-benzylamide N-(pyridin-4-ylmethyl)-4-(4-cyanobenzyl)-5-oxo-4H-[1,2,4]triazolo[4,3-a]quinazol-7-ylcarboxamide Methyl (4-{7-[(1,3-benzodioxol-5-ylmethyl)-carbamoyl]-5-oxo-5H-[1,2,4]triazolo[4,3-a]quinazolin-4-ylmethyl}-phenyl)-acetate Methyl (4-{7-[(4-methoxy)-benzylcarbamoyl]-5-oxo-5H-[1,2,4]triazolo[4,3-a]quinazolin-4-ylmethyl}-phenyl)-acetate Methyl (4-{7-[(pyridin-4-yl)-methylcarbamoyl]-5-oxo-5H-[1,2,4]triazolo[4,3-a]quinazolin-4-ylmethyl}-phenyl)-acetate N-(pyridin-4-ylmethyl) 4-[3-(pyridin-4-yl)-2-propen-1-yl]-5-oxo-4H-[1,2,4]triazolo[4,3-a]quinazol-7-ylcarboxamide 4-[2-(4-Chloro-phenoxy)-ethyl]-5-oxo-4,5-dihydro-[1,2,4]triazolo[4,3-a]quinazoline-7-carboxylic acid 4-methoxy-benzylamide 4-{7-[(4-methoxybenzyl)-carbamoyl]-5-oxo-5H-[1,2,4]triazolo[4,3-a]quinazol-4-ylmethyl}benzoic acid 4-{7-[(1,3-benzodioxol-5-ylmethyl)-carbamoyl]-5-oxo-5H-[1,2,4]triazolo[4,3-a]quinazol-4-ylmethyl}benzoic acid 4-{7-[(pyridin-4-ylmethyl)-carbamoyl]-5-oxo-5H-[1,2,4]triazolo[4,3-a]quinazol-4-ylmethyl}benzoic acid 4-{7-[(4-fluoro)-benzylcarbamoyl]-5-oxo-5H-[1,2,4]triazolo[4,3-a]quinazol-4-ylmethyl}benzoic acid (4-{7-[(4-methoxy)-benzylcarbamoyl]-5-oxo-5H-[1,2,4]triazolo[4,3-a]quinazolin-4-ylmethyl}-phenyl)-acetic acid (4-{7-[(1,3-benzodioxol-5-ylmethyl)-carbamoyl]-5-oxo-5H-[1,2,4]triazolo[4,3-a]quinazolin-4-ylmethyl}-phenyl)-acetic acid, and (4-(7-[(pyridin-4-yl)-methylcarbamoyl]-5-oxo-5H-[1,2,4]triazolo[4,3-a]quinazolin-4-ylmethyl}-phenyl)-acetic acid.

18. A compound according to claim 1 selected from:

benzyl 4-benzyl-5-oxo-4H-[1,2,4]triazolo[4,3-a]quinazol-7-ylcarboxylate, 4-pyridylmethyl 4-benzyl-5-oxo-4H-[1,2,4]triazolo[4,3-a]quinazol-7-ylcarboxylate, N-(3,4-methylenedioxybenzyl)-4-benzyl-5-oxo-4H-[1,2,4]triazolo[4,3-a]quinazol-7-ylcarboxamide, N-(4-methoxybenzyl)-4-benzyl-5-oxo-4,5-dihydro[1,2,4]triazolo[4,3-a]quinazoline-7-carboxamide, N-(3,4-Methylenedioxybenzyl)-4-(4-cyanobenzyl)-5-oxo-4H-[1,2,4]triazolo[4,3-a]quinazol-7-ylcarboxamide Methyl 4-{7-[(1,3-benzodioxol-5-ylmethyl)-carbamoyl]-5-oxo-5H-[1,2,4]triazolo[4,3-a]quinazol-4-ylmethyl}benzoate Methyl 4-{7-[(4-methoxybenzyl)-carbamoyl]-5-oxo-5H-[1,2,4]triazolo[4,3-a]quinazol-4-ylmethyl}benzoate 4-(4-Dimethylcarbamoyl-benzyl)-5-oxo-4,5-dihydro-[1,2,4]triazolo[4,3-a]quinazoline-7-carboxylic acid 4-methoxy-benzylamide Methyl (4-{7-[(1,3-benzodioxol-5-ylmethyl)-carbamoyl]-5-oxo-5H-[1,2,4]triazolo[4,3-a]quinazolin-4-ylmethyl}-phenyl)-acetate Methyl (4-{7-[(4-methoxy)-benzylcarbamoyl]-5-oxo-5H-[1,2,4]triazolo[4,3-a]quinazolin-4-ylmethyl}-phenyl)-acetate 4-{7-[(4-methoxybenzyl)-carbamoyl]-5-oxo-5H-[1,2,4]triazolo[4,3-a]quinazol-4-ylmethyl}benzoic acid 4-{7-[(1,3-benzodioxol-5-ylmethyl)-carbamoyl]-5-oxo-5H-[1,2,4]triazolo[4,3-a]quinazol-4-ylmethyl}benzoic acid 4-{7-[(pyridin-4-ylmethyl)-carbamoyl]-5-oxo-5H-[1,2,4]triazolo[4,3-a]quinazol-4-ylmethyl}benzoic acid 4-{7-[(4-fluoro)-benzylcarbamoyl]-5-oxo-5H-[1,2,4]triazolo[4,3-a]quinazol-4-ylmethyl}benzoic acid (4-{7-[(4-methoxy)-benzylcarbamoyl]-5-oxo-5H-[1,2,4]triazolo[4,3-a]quinazolin-4-ylmethyl}-phenyl)-acetic acid (4-{7-[(1,3-benzodioxol-5-ylmethyl)-carbamoyl]-5-oxo-5H-[1,2,4]triazolo[4,3-a]quinazolin-4-ylmethyl}-phenyl)-acetic acid, and (4-{7-[(pyridin-4-yl)-methylcarbamoyl]-5-oxo-5H-[1,2,4]triazolo[4,3-a]quinazolin-4-ylmethyl}-phenyl)-acetic acid.

19. The compound according to claim 1, wherein aryl represents a monocycle or bicycle containing from 5 to 6 carbon atoms.

20. The compound according to claim 1, wherein cycloalkyl represents a monocycle or bicycle containing from 3 to 6 carbon atoms.

21. The compound according to claim 1, wherein aryl $(C_1-C_6)$alkyl represents a group in which alkyl contains from 1 to 4 carbon atoms and aryl contains from 5 to 10 carbon atoms.

22. The compound according to claim 1, wherein aryl $(C_1-C_6)$alkyl represents a group in which alkyl contains from 1 to 6 carbon atoms and aryl contains 5 or 6 carbon atoms.

23. The compound according to claim 1, wherein cycloalkyl$(C_1-C_6)$alkyl represents a group in which alkyl contains from 1 to 3 carbon atoms and cycloalkyl contains from 3 to 10 carbon atoms.

24. Process for manufacturing a compound of general formula (I)

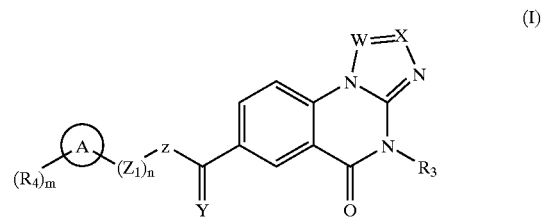

(I)

in which W, X, $R_3$, $R_4$, n, m, $Z_1$ and A are as defined in claim 1, Y is O and Z is O, the said process being characterized in that it comprises the reaction of the compound of formula (7a):

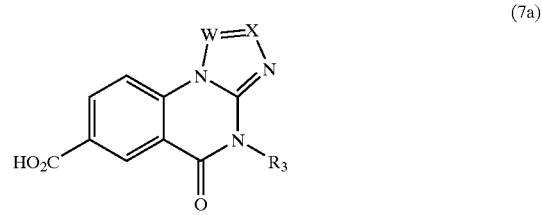

(7a)

in which W, X, and $R_3$ are as defined in the compound of formula (I), with the compound of general formula (7g), in the presence of a base:

(7g)

in which hal is a halogen atom, and in which $R_4$, n, m, $Z_1$ and A are as in the compound of formula (I), to give the compound of general formula (7c), which is a particular case of the compounds of formula (I):

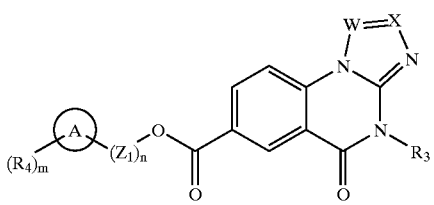

(7c)

in which W, X, $R_3$, $R_4$, n, m, $Z_1$ and A are as defined hereinbefore.

25. Process for manufacturing a compound of general formula (I)

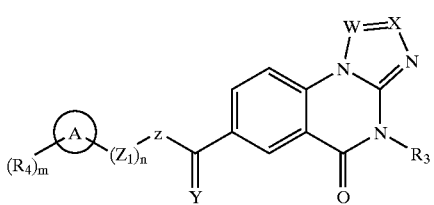

(I)

in which W, X, $R_3$, $R_4$, n, m, $Z_1$ and A are as defined in claim 1, Y is O and Z is —$NR_8$, in which $R_8$ is as defined in claim 1, the said process being characterized in that it comprises the reaction of the compound of formula (7a):

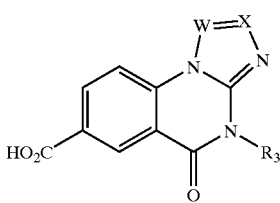

(7a)

in which W, X, and $R_3$ are as defined in the compound of formula (I),
with the compound of general formula (7i):

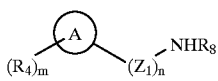

(7i)

in which $R_4$, $R_8$, n, m, $Z_1$ and A are as defined in the compound of formula (I),
by activating the acid function with an activator, in the presence of diisopropylethylamine (DIPEA) and in a solvent, to give the compound of general formula (7d), which is a particular case of the compounds of formula (I):

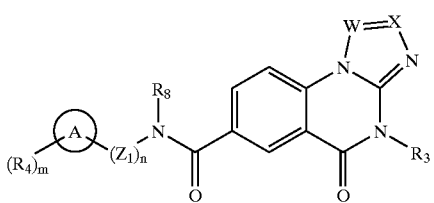

(7d)

in which W, X, $R_3$, $R_4$, $R_8$, n, m, $Z_1$ and A are as defined hereinbefore.

26. Process for manufacturing a compound of general formula (I),

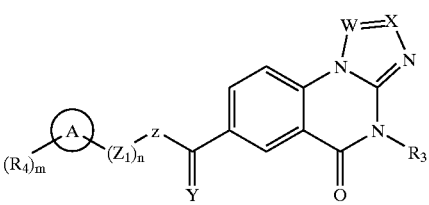

(I)

in which W, X, $R_3$, $R_4$, n, m, $Z_1$ and A are as defined in claim 1, Y is O and Z is S, the said process being characterized in that it comprises the reaction of the compound of formula (7a):

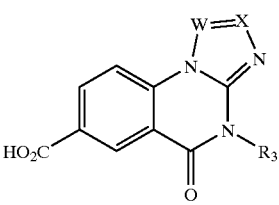

(7a)

in which W, X, and $R_3$ are as defined in the compound of formula (I), with the compound of general formula (7j):

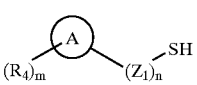

(7j)

in which $R_4$, n, m, $Z_1$ and A are as defined in the compound of formula (I), by activating the acid function with an activator, in the presence of DIPEA in a solvent, to give the compound of general formula (7e), which is a particular case of the compounds of formula (I):

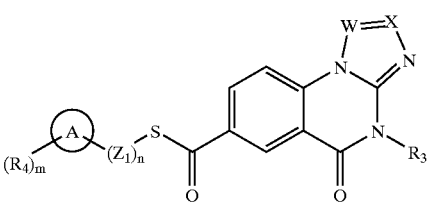

(7e)

in which W, X, $R_3$, $R_4$, n, m, $Z_1$ and A are as defined hereinbefore.

27. Process for manufacturing a compound of general formula (I),

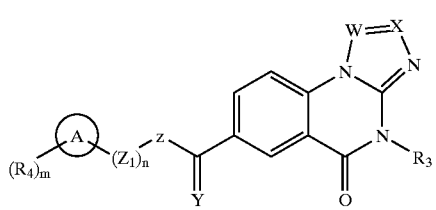

in which W, X, $R_3$, $R_4$, n, m, $Z_1$ and A are as defined in claim 1, Y is O and Z is O, the said process being characterized in that it comprises the reaction of the compound of formula (7b):

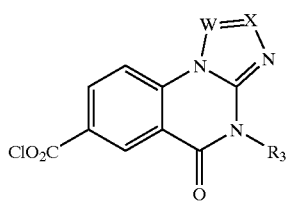

in which W, X, and $R_3$ are as defined in the compound of formula (I),
with the compound of formula (7h):

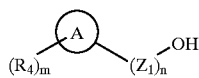

in which $R_4$, n, m, $Z_1$ and A are as defined in the compound of formula (I),
in the presence of a base, to give the compound of general formula (7c), which is a particular case of the compounds of formula (I):

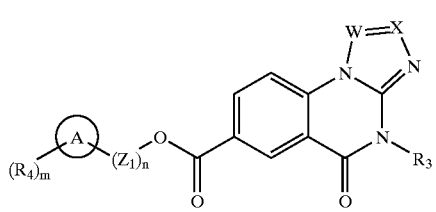

in which W, X, $R_3$, $R_4$, n, m, $Z_1$ and A are as defined hereinbefore.

28. Process for manufacturing a compound of general formula (I),

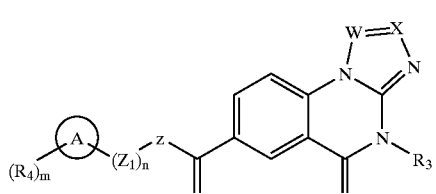

in which W, X, $R_3$, $R_4$, n, m, $Z_1$ and A are as defined in claim 1, Y is O and Z is —$NR_8$, in which $R_8$ is defined in claim 1, the said process being characterized in that it comprises the reaction of the compound of formula (7b):

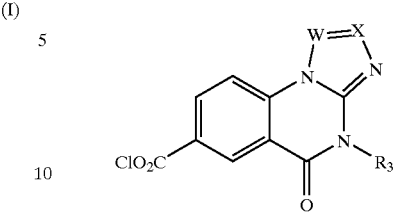

in which W, X, and $R_3$ are as defined in the compound of formula (I),
with the compound of formula (7i):

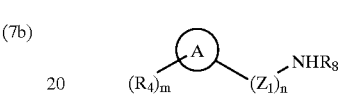

in which $R_4$, $R_8$, n, m, $Z_1$ and A are as defined in the compound of formula (I),
in the presence of a base, to give the compound of general formula (7d), which is a particular case of the compounds of formula (I):

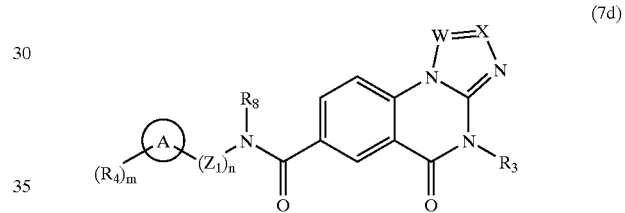

in which W, X, $R_3$, $R_4$, $R_8$, n, m, $Z_1$ and A are as defined hereinbefore.

29. Process for manufacturing a compound of general formula (I),

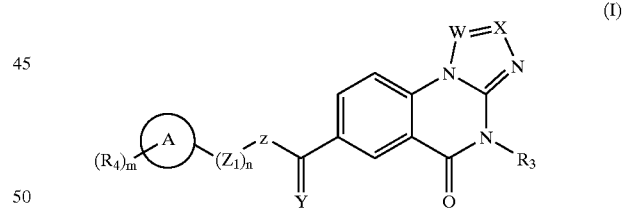

in which W, X, $R_3$, $R_4$, n, m, $Z_1$ and A are as defined above claim 28, Y is O and Z is S, the said process being characterized in that it comprises the reaction of the compound of formula (7b):

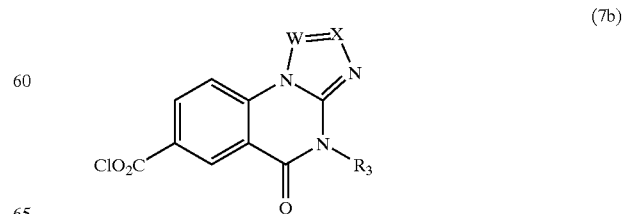

in which W, X, and $R_3$ are as defined in the compound of formula (I),
with the compound of general formula (7j):

(7j)

in which $R_4$, n, m, $Z_1$ and A are as defined in the compound of formula (I),
to give the compound of general formula (7e), which is a particular case of the compounds of formula (I):

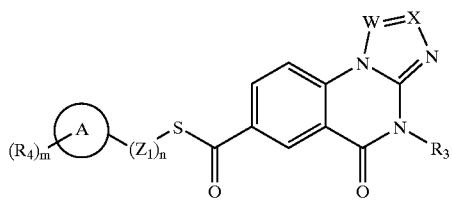

in which W, X, $R_3$, $R_4$, n, m, $Z_1$ and A are as defined hereinbefore.

30. Process for manufacturing a compound of general formula (I),

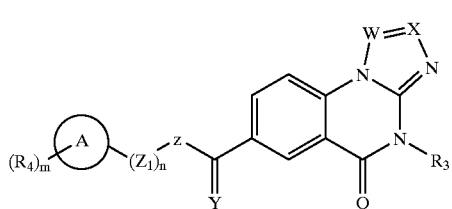
(I)

in which W, X, $R_3$, $R_4$, n, m, $Z_1$ and A are as defined above in claim 23, Y is O and Z is —CHRa, in which Ra represents a group selected from hydrogen, $(C_1-C_6)$alkyl, aryl, aryl$(C_1-C_6)$alkyl, aromatic heterocycle, non-aromatic heterocycle, and cycloalkyl, the said process being characterized in that it comprises the reaction of the compound of formula (7b):

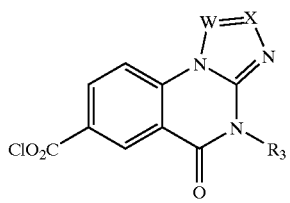
(7b)

in which W, X, and $R_3$ are as defined in the compound of formula (I),
with the compound of general formula (7k):

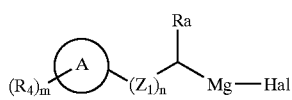
(7k)

in which Ra represents a group selected from hydrogen, $(C_1-C_6)$alkyl, aryl, aryl$(C_1-C_6)$alkyl, aromatic heterocycle, non-aromatic heterocycle, and cycloalkyl, Hal represents a halogen atom, and $R_4$, n, m, $Z_1$ and A are as defined in the compound of formula (I), to give the compound of general formula (7f), which is a particular case of the compounds of formula (I):

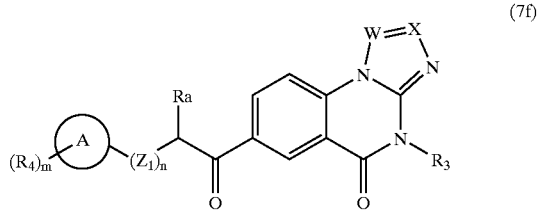
(7f)

in which W, X, $R_3$, $R_4$, Ra, n, m, $Z_1$ and A are as defined hereinbefore.

31. Process for manufacturing a compound of general formula (I),

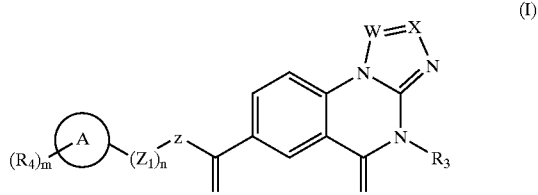
(I)

in which W, X, $R_3$, $R_4$, n, m, Z, $Z_1$ and A are as defined in claim 1, and Y is S, the said process being characterized in that it comprises the reaction of the compound (8a):

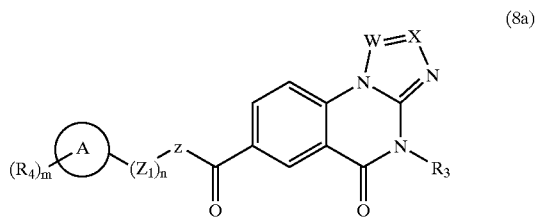
(8a)

in which W, X, $R_3$, $R_4$, n, m, Z, $Z_1$ and A are as defined in the compound of formula (I), with Lawesson's reagent or $P_2S_5$, to give the compound of general formula (8b), which is a particular case of the compounds of formula (I):

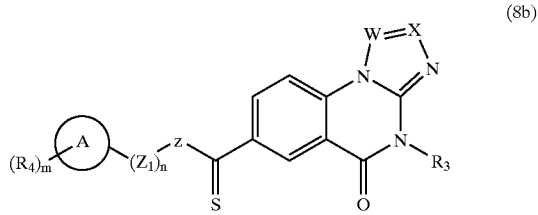
(8b)

in which W, X, $R_3$, $R_4$, n, m, Z, $Z_1$ and A are as defined hereinbefore.

32. Process for manufacturing a compound of general formula (I),

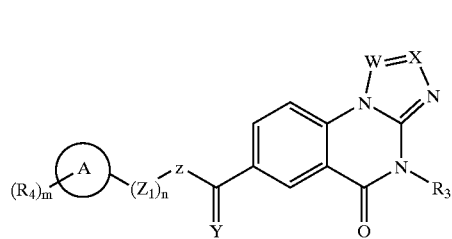
(I)

in which W, X, R$_3$, R$_4$, n, m, Z$_1$ and A are as defined in claim 1, Y is NH and Z is O, the said process being characterized in that it comprises the reaction of compound (9a):

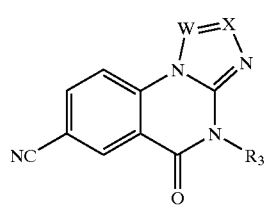
(9a)

in which W, X, and R$_3$ are as defined in the compound of formula (I),
with the compound of general formula (7h):

(7h)

in which R$_4$, n, m, Z$_1$ and A are as defined in the compound of formula (I),
to give the compound of general formula (9b), which is a particular case of the compounds of formula (I):

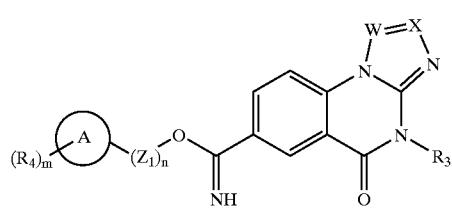
(9b)

in which W, X, R$_3$, R$_4$, n, m, Z$_1$ and A are as defined hereinbefore.

33. Process for manufacturing a compound of general formula (I),

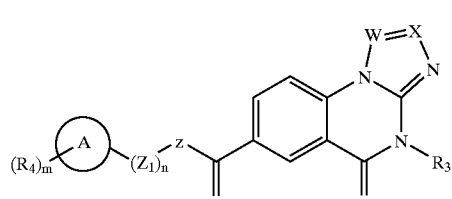
(I)

in which W, X, R$_3$, R$_4$, n, m, Z$_1$ and A are as defined in claim 1, Z is —NR$_8$ and Y is NH,
the said process being characterized in that it comprises the reaction of compound (9a):

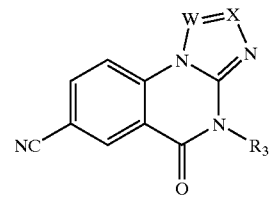
(9a)

in which W, X, and R$_3$ are as defined in the compound of formula (I),
with the compound of general formula (7i):

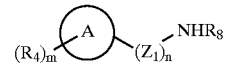
(7i)

in which R$_4$, n, m, Z$_1$ and A are as defined in the compound of formula (I),
to give the compound of general formula (9c), which is a particular case of the compounds of formula (I):

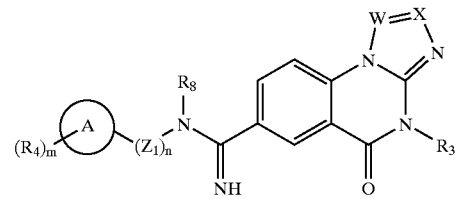
(9c)

in which W, X, R$_3$, R$_4$, R$_8$, n, m, Z$_1$ and A are as defined hereinbefore.

34. Process for manufacturing a compound of general formula (I),

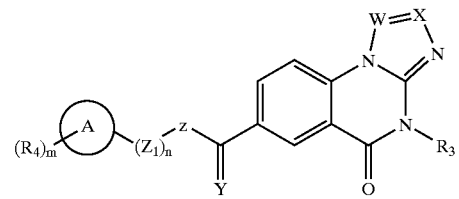
(I)

in which W, X, R$_3$, R$_4$, n, m, Z$_1$ and A are as defined in claim 1, Z is S and Y is NH, the said process being characterized in that it comprises the reaction of compound (9a):

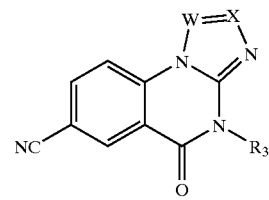
(9a)

in which W, X, and R$_3$ are as defined in the compound of formula (I),
with the compound of general formula (7j):

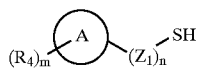
(7j)

in which $R_4$, n, m, $Z_1$ and A are as defined in the compound of formula (I), to give the compound of general formula (9d) which is a particular case of the compounds of formula (I):

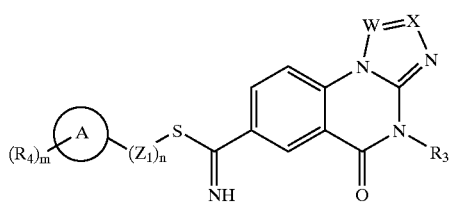
(9d)

in which W, X, $R_3$, $R_4$, n, m, $Z_1$ and A are as defined hereinbefore.

35. Process for manufacturing a compound of general formula (I),

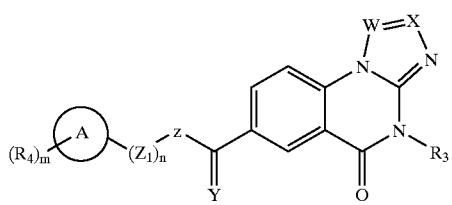
(I)

in which W, X, $R_3$, $R_4$, n, m, $Z_1$ and A are as defined in claim 1, Z is —CHRa in which Ra represents a group selected from hydrogen, $(C_1-C_6)$alkyl, aryl, aryl$(C_1-C_6)$alkyl, aromatic heterocycle, non-aromatic heterocycle, and cycloalkyl, and Y is N—Rb in which Rb is a $(C_1-C_6)$alkyl, the said process being characterized in that it comprises the reaction of compound (7f):

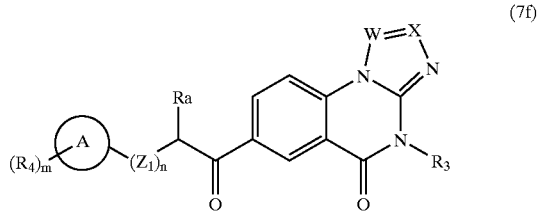
(7f)

in which W, X, $R_3$, $R_4$, n, m, $Z_1$ and A are as defined in the compound of formula (I), and in which Ra is as defined hereinbefore, with Rb—$NH_2$, in which Rb represents a $(C_1-C_6)$alkyl group, in a presence of a dehydrating agent, to give the compound of general formula (10a), which is a particular case of the compounds of formula (I):

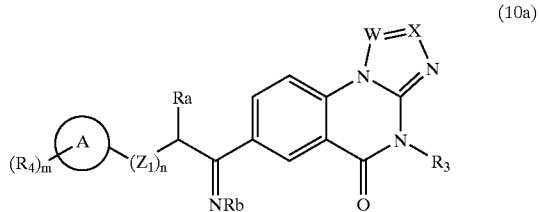
(10a)

in which W, X, $R_3$, $R_4$, n, m, $Z_1$, Ra, Rb and A are as defined hereinbefore.

36. A pharmaceutical composition comprising a compound according to any one of claims 1 to 18 and a pharmaceutically acceptable excipient.

37. A method for treating arthritis, the method comprising the administration of an effective amount of a compound according to any one of claims 1 to 18 to a patient having arthritis.

38. A method for treating osteoarthritis, the method comprising the administration of an effective amount of a compound according to any one of claims 1 to 18 to a patient having osteoarthritis.

39. A method for treating rheumatoid arthritis, the method comprising the administration of an effective amount of a compound according to any one of claims 1 to 18 to a patient having rheumatoid arthritis.

* * * * *